United States Patent
Suh et al.

(10) Patent No.: US 9,717,222 B2
(45) Date of Patent: Aug. 1, 2017

(54) TASTE INDEPENDENT BRAIN NUTRIENT SENSOR THAT MEDIATES HUNGER

(71) Applicant: New York University, New York, NY (US)

(72) Inventors: Greg Seong-Bae Suh, New York, NY (US); Monica Dus, Ann Arbor, MI (US)

(73) Assignee: New York University, New York, NY (US)

( * ) Notice: Subject to any disclaimer, the term of this patent is extended or adjusted under 35 U.S.C. 154(b) by 0 days.

(21) Appl. No.: 14/673,334

(22) Filed: Mar. 30, 2015

(65) Prior Publication Data

US 2015/0272093 A1    Oct. 1, 2015

Related U.S. Application Data

(60) Provisional application No. 61/971,891, filed on Mar. 28, 2014.

(51) Int. Cl.
*G01N 33/00* (2006.01)
*A01K 67/033* (2006.01)
*C07K 14/435* (2006.01)

(52) U.S. Cl.
CPC .... *A01K 67/0339* (2013.01); *C07K 14/43581* (2013.01); *A01K 2207/15* (2013.01); *A01K 2207/25* (2013.01); *A01K 2217/052* (2013.01); *A01K 2227/706* (2013.01); *A01K 2267/03* (2013.01)

(58) Field of Classification Search
CPC .................................................. A01K 67/0339
USPC ............................................................ 800/3
See application file for complete search history.

(56) References Cited

PUBLICATIONS

Dus et al. (e-Pub Mar. 31, 2013, Nature Neuroscience, vol. 16(5), pp. 526-529).*
Xu et al. (2008, Cell Metabolism, vol. 8(4), pp. 289-300).*
Roll et al. (2002, Gene, vol. 285, pp. 141-148).*
Pandey et al. (2011, Pharmacological Reviews, vol. 63, pp. 411-436).*
Lee Y. (2013, PLOS One, vol. 8(12), pp. 1-10).*
Gilbertson et al. (1997, Cell Physiology, vol. 41, pp. C1203-C1210).*
De Araujo et al., Metabolic Regulation of Brain Response to Food Cues, Current Biology 23, pp. 878-883. May 20, 2013.
Dus et al., Nutrient Sensor in the Brain Directs the Action of the Brain-Gut Axis in *Drosophila*, Neuron 87, 139-151. Jul. 1, 2015.
Zukerman et al., Post-oral appetite stimulation by sugars and nonmetabolizable sugar analogs, Am. J. Physiol. Regul. Integr. Comp. Physiol. 305: R840-R853. Aug. 7, 2013.
Domingos et al., Hypothalamic melanin concentrating hormone neurons communicate the nutrient value of sugar, eLife 2013;2:e01462, pp. 1-15. Dec. 31, 2013.
Smith et al., From fat fruit fly to human obesity, Phsiology & Behavior 136 (2014) 15-21. Feb. 6, 2014.
Dus, M., et al., Taste-independent detection of the caloric content of sugar in Drosophila, PNAS, Jul. 12, 2011, vol. 108, No. 28, pp. 11644-11649.
Adrenal gland From Wikipedia, the free encyclopedia pp. 1-15, downloaded Sep. 1, 2016.
Menzies, J.R.W., et al., Neural Substrates Underlying Interactions between Appetite Stress and Reward, Obesity Facts, 2012; vol. 5, pp. 208-220.
Patel, M., et al., Localization of Locusta-DP in Locust CNS and Hemolymph Satisfies Initial Hormonal Criteria, Peptides, 1994, vol. 15, No. 4, pp. 591-602.
Hector, C.E., et al., Functional differences between two CRF-related diuretic hormone receptors in Drosophila, The Journal of Experimental Biology, 2009, vol. 212, pp. 3142-3147.
Johnson, E.C., et al., Drosophila CG8422 encodes a functional diuretic hormone receptor, The Journal of Experimental Biology, 2004, vol. 207, 743-748.
De Araujo, I.E., et al., Food Reward in the Absence of Taste Receptor Signaling, Neuron, Mar. 27, 2008, vol. 57, pp. 930-941.

* cited by examiner

*Primary Examiner* — Thaian N Ton
*Assistant Examiner* — David A Montanari
(74) *Attorney, Agent, or Firm* — Hodgson Russ LLP

(57) ABSTRACT

Provided is a gene in *drosophila* designated as dSLC5A1. This gene is responsible for taste independent nutrient sensing. Activation of neurons expressing this gene results in hunger behavior. Provided are compositions and methods for identifying agents that can interfere with hunger behavior.

11 Claims, 24 Drawing Sheets

TASTE INDEPENDENT BRAIN NUTRIENT SENSOR THAT MEDIATES HUNGER

CROSS-REFERENCE TO RELATED APPLICATIONS

This application claims priority to provisional patent application No. 61/971,891, filed Mar. 28, 2014, the disclosure of which is herein incorporated by reference.

STATEMENT REGARDING FEDERALLY-SPONSORED RESEARCH

This invention was made with government support under Grant Number RO1DC01279-01 from the National Institutes of Health. The government has certain rights in the invention.

FIELD OF THE DISCLOSURE

This disclosure relates to materials and methods for screening of compounds for their ability to interfere with nutrient sensing that is related to sensation of hunger.

BACKGROUND OF THE DISCLOSURE

Traditionally it was thought that palatability, through its action on reward centers in the brain, played a major role in reinforcing feeding. However, it has become increasingly clear that calories/nutrients, not palatability, act as primary post-ingestive reinforces on feeding. Animals can determine the nutritional value of sugar without the influence of taste.

Hunger is a powerful drive that stimulates food intake. The means by which hunger influences the brain to promote feeding behavior is unclear, however. The sensation of hunger is a complex motivational state that promotes multiple facets of feeding behavior. Food deprivation increases subsequent food consumption and other behaviors related to food seeking that results in the selection of nutrient-rich food and enhances sensory sensitivity in both insects and vertebrates. The mechanism by which energy deficits are represented in the brain and incorporated to modulate feeding behaviors is not well understood in any animal system. *Drosophila* provides a model for studying the neural correlates of hunger. Its genetically amenable system affords the unbiased screening of cells or populations of neurons in the adult brain that are crucial for mediating the motivational states induced by hunger.

SUMMARY OF THE DISCLOSURE

The present disclosure identifies a gene in *drosophila*, designated dSLC5A11 (or cupcake) as the gene responsible for taste independent nutrient sensing that mediates the sensation of hunger. This disclosure provides compositions and methods for identifying agents that can affect feeding behavior related to the sensation of hunger.

A *Drosophila* mutant has been identified that is insensitive to the nutritional value of sugars, but responds only to the concentration (i.e. sweetness). The affected gene encodes a sodium/solute cotransporter-like protein, designated dSLC5A11 (or cupcake), which is structurally similar to mammalian sodium/glucose cotransporters (SGLTs) that transport sugar across the intestinal and renal lumen. However, dSLC5A11 is prominently expressed in 10-13 pairs of R4 neurons of the ellipsoid body (EB) in the brain and functions in these neurons for selecting appropriate foods. dSLC5A11 and EB R4 neurons may carry out a critical signaling function in responding to internal glycemic levels.

We further found that dSLC5A11 R4 neuronal excitability increases dramatically in animals subjected to food deprivation and that this increase is abolished in dSLC5A11 mutants. Artificial activation of dSLC5A11 neurons (also referred to herein as dSLC5A11 R4 neurons) was sufficient to promote food intake and hunger-driven behaviors. Conversely, silencing these neurons resulted in opposite phenotypes. Intriguingly, dSLC5A11 transcript levels rose significantly following starvation, specifically when the flies have been deprived of sugar. We observed that dSLC5A11 stimulates neuronal excitability by suppressing the potassium current generated by *Drosophila* KCNQ. Accordingly, starved dKCNQ mutant flies failed to exhibit hunger-drive behaviors. Based on these results, the present disclosure indicates that starvation promotes the production of dSLC5A11, which enhances R4 neuronal excitability by suppressing dKCNQ-mediated currents, thereby conferring a sensation of hunger in fruit flies.

In one aspect, this disclosure provides cDNA sequence corresponding to dSLC5A11. In one aspect, this disclosure provides cells into which have been introduced polynucleotides which encodes for a protein encoded by dSLC5A11. Such cells may be cells in vitro (such as in culture) or cells in vivo (such as in a transgenic fly or another animal). The cells may be *drosophila* cells or may be mammalian cells including human cells.

In one aspect, this disclosure provides a method for identifying human homolog of the *Drosophila* dSLC5A11 gene. For example, human sodium/glucose co-transporters can be cloned into a *Drosophila* expression vector. The vector is then introduced into a *Drosophila* embryo resulting in the generation of transgenic flies. The transgenic flies can then be used in screening assay to identify those which are the functional homolog of dSLC5A11 by evaluating one or more of the characteristics described herein, such as, for example, the ability to preferentially intake D-glucose upon starvation.

In one aspect, this disclosure provides *drosophila* mutants (dSLC5A11) which have lack the ability to preferentially intake metabolizing sugars (such as D-glucose) when starved. In one embodiment, this disclosure provides a method for assessing whether a test agent can restore the ability of dSLC5A11 mutants to preferentially intake metabolizing sugar when starved, or to affect the behavior associated with hunger. In one embodiment, the test can be carried out in *drosophila* carrying a human homolog of dSLC5A1/(e.g., a SGLT)—in its wild type form or a mutated form. Whether a test agent is able to rescue the phenotype in the mutants may be tested in various ways. For example, in one embodiment, the screen may involve determining restoration of normal feeding behavior such as preference for D-glucose in starved flies. In one embodiment, the test may involve evaluation of steps related to the functioning of dSLC5A11. For example, in one embodiment, the amount of dSLC5A11 transcript or dSLC5A11 protein may be measured. In one embodiment, KCNQ current characteristics may be measured.

In one embodiment, the dSLC5A11 R4 neurons are activated and various test agents screened for their effect on the excitability of these neurons or on events downstream of the activation. Activation of neurons can be achieved by introduction of activating stimuli such as, for example, introduction of polynucleotides encoding NaChBac (Bacterial channel) or TrpA1. As described in the examples herein, excitation of dSLC5A11 R4 neurons in wild type flies results in hunger associated behavior and specific electrophysiological events such as a suppression of KCNQ mediated potassium current. Thus, following excitation of R4 neurons, one or more of the following may be evaluated: dSLC5A11 expression (transcript and/or protein), food intake, food choice, food seeking behavior, and KCNQ mediated potassium current. While some of these characteristics can be evaluated in intact files (such as food behavior), while other characteristics (electrical recordings, dSLC5A11 expression) can be evaluated in isolated brains or isolated R4 neurons in culture.

Figure 17:
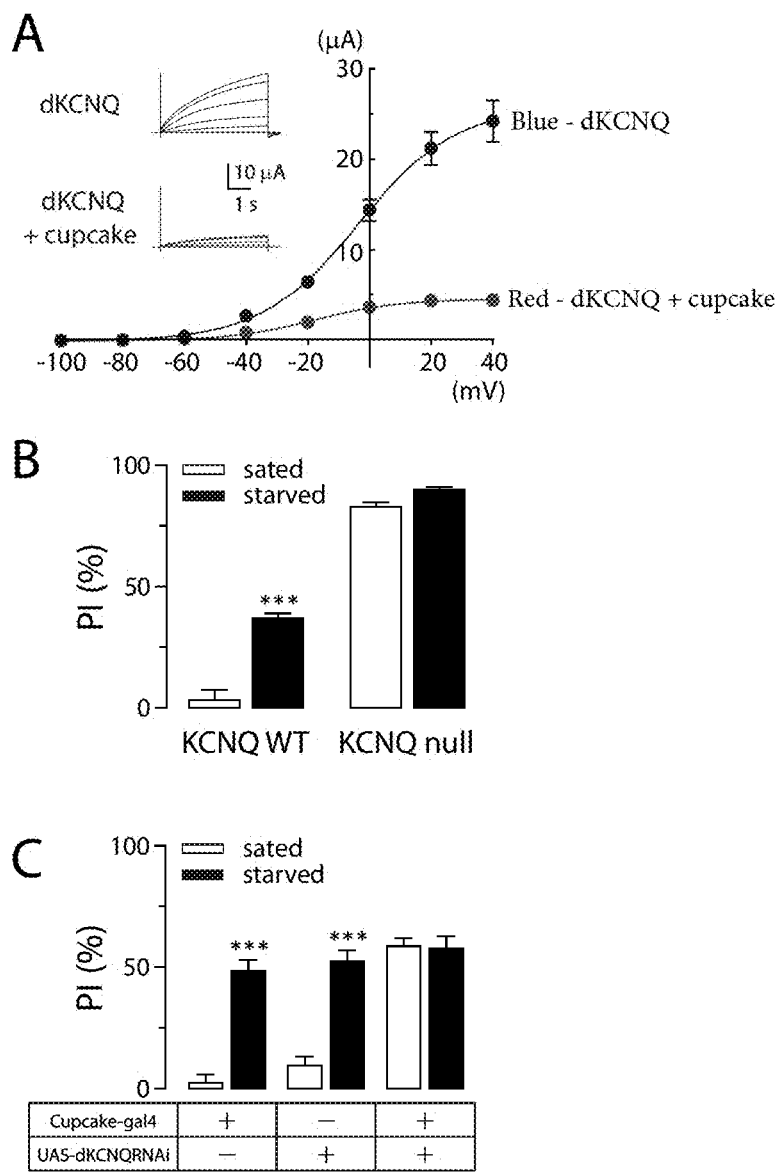

FIG. 17. Down-regulation of dKCNQ channel activity by dSLC5A11 during periods of starvation leads to the stimulation of hunger-driven food choice behavior. (A) Current-voltage relationships in oocytes expressing dKCNQ only (blue trace), or dKCNQ and dSLC5A11 (red trace) (n=17-20). Inset, representative current traces. (B) Behavior responses of dKCNQ mutant and control wild type flies in the two-choice assay. Flies were given a choice between 50 mM D-glucose and 220 mM L-glucose (n=6-7). (C) Two-choice behavior responses of 4-hr (sated) or 22-hr (starved) food deprived flies in which dSLC5A11 was knocked down in dSLC5A11 neurons through RNAi and control flies (n=7-8). ***P<0.001; error bars indicate SEM.

Figure 18:
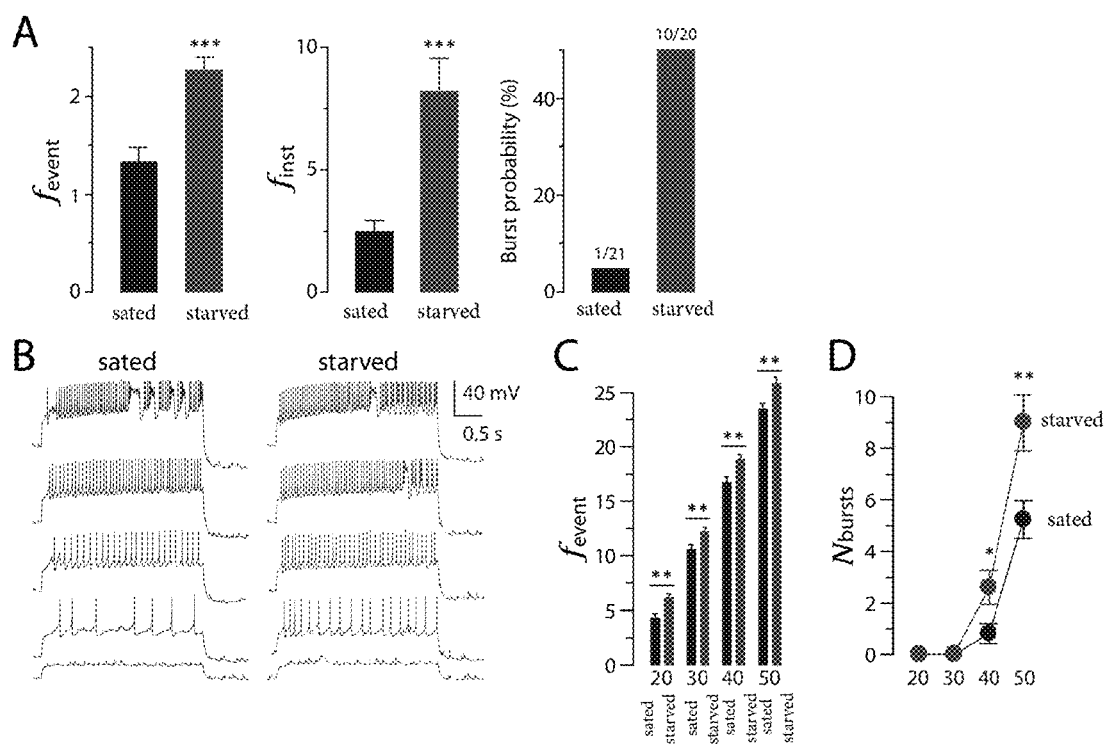

FIG. 18. Starvation enhances excitability of dSLC5A11 neurons. (A) Quantification of action potential firing frequency and bursting probability in dSLC5A11 neurons from isolated brains of sated and starved flies. The number of bursting neurons out of the total number of recorded neurons is indicated above the bars. (B) Responses to step current injections of 10, 20, 30, 40, and 50 pA from a holding potential of −65 mV. (C) Summary of firing frequency and (D) number of bursting events during step depolarization in dSLC5A11 neurons of sated and starved flies (n=25-27). $f_{event}$, event frequency. $f_{inst}$, instantaneous frequency. $N_{burst}$, number of burst firing event. *P<0.05, **P<0.01; error bars indicate SEM.

Figure 19:
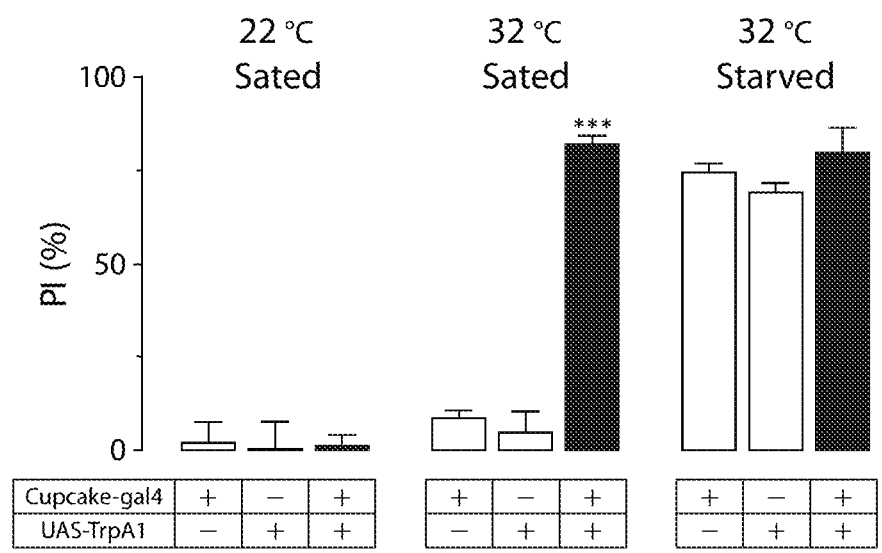

FIG. 19. Acute activation of dSLC5A11 neurons using dTrpA1 directs the flies to select D-glucose over L-glucose even when they are sated. Behavior responses of 4-hr (sated) or 22-hr (starved) food deprived flies in the two-choice assay. Flies were given a choice between 50 mM D-glucose and 270 mM L-glucose (n=6-8). ***P<0.001; error bars indicate SEM.

Figure 20:
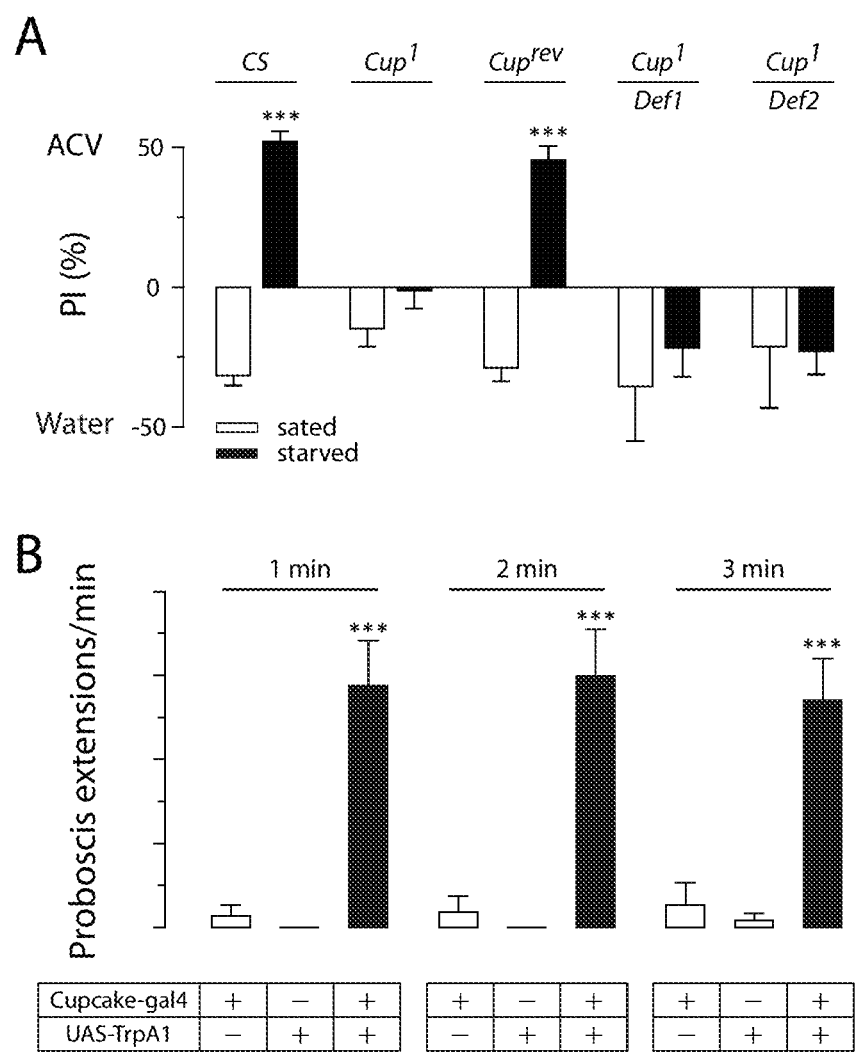

FIG. 20. dSLC5A11 is necessary for hunger-driven odor preference and artificial activation of dSLC5A11 neuron is sufficient for mediating PER responses. (A) Behavior responses of different dSLC5A11 allelic combinations and controls that were 4-hr (sated) or 22-hr (starved) food deprived were given a choice between a tube containing 10 ul of ACV and another containing 10 ul of water in a T-maze (n=6-20). (B) Acute activation of dSLC5A11 neurons by using TrpA1 promotes robust PER responses in the absence of food (n=12-19). ***P<0.001; error bars indicate SEM.

Figure 21:
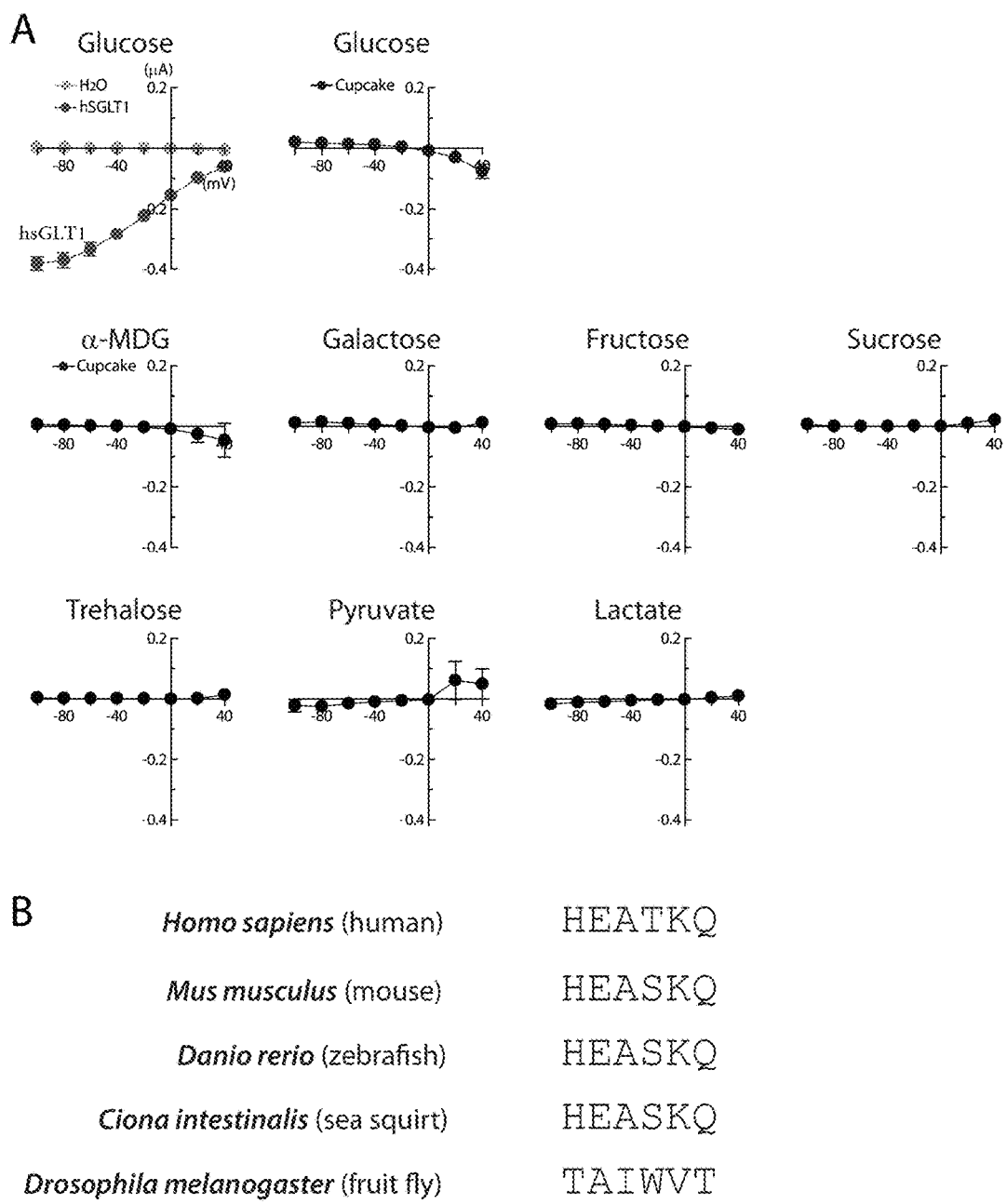

FIG. 21. dSLC5A11 does not gate sugar-dependent co-transport current. (A) (Upper) Glucose-dependent co-transport current and voltage analysis of hSGLT1 (left) or dSLC5A11 (right) expressed in *Xenopus* oocytes (n=12-13). (Middle and lower) Sugar-dependent co-transport current and voltage relationship was measured in oocytes expressing dSLC5A11, which were stimulated by different sugars (n=3-4). Error bars indicate SEM. (B) Sequence alignment of the putative sugar-binding site.

Figure 22:
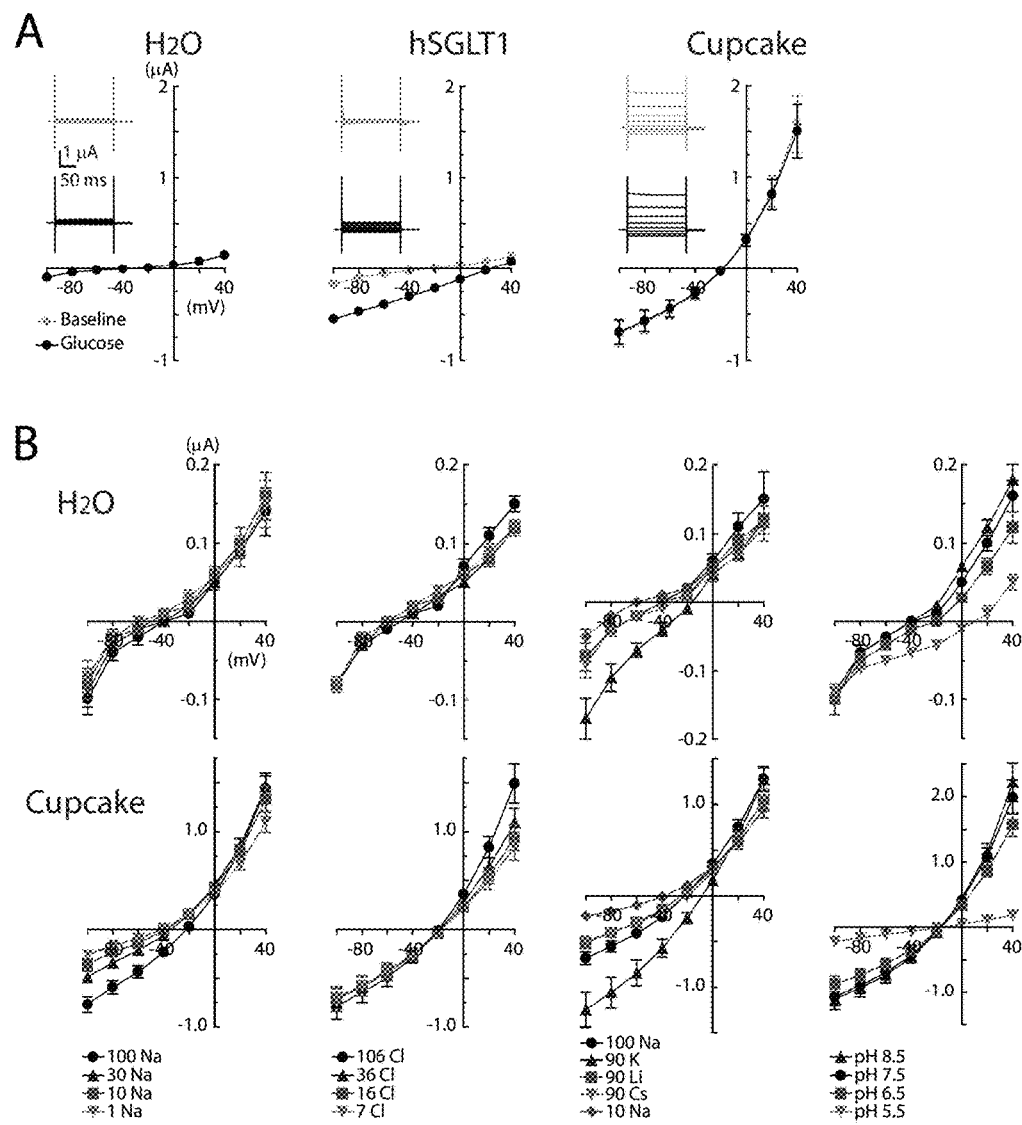

FIG. 22. dSLC5A11 generates leak current. (A) Current-voltage analysis of human SGLT1 and dSLC5A11 expressed in oocytes (n=12-13). Gray, pre-glucose treatment; Black, post-glucose treatment. Inset, representative current traces. (B) Current-voltage analysis of dSLC5A11 expressed in oocytes with bath solutions containing different cation compositions (n=10-11). Error bars indicate SEM.

Figure 23:
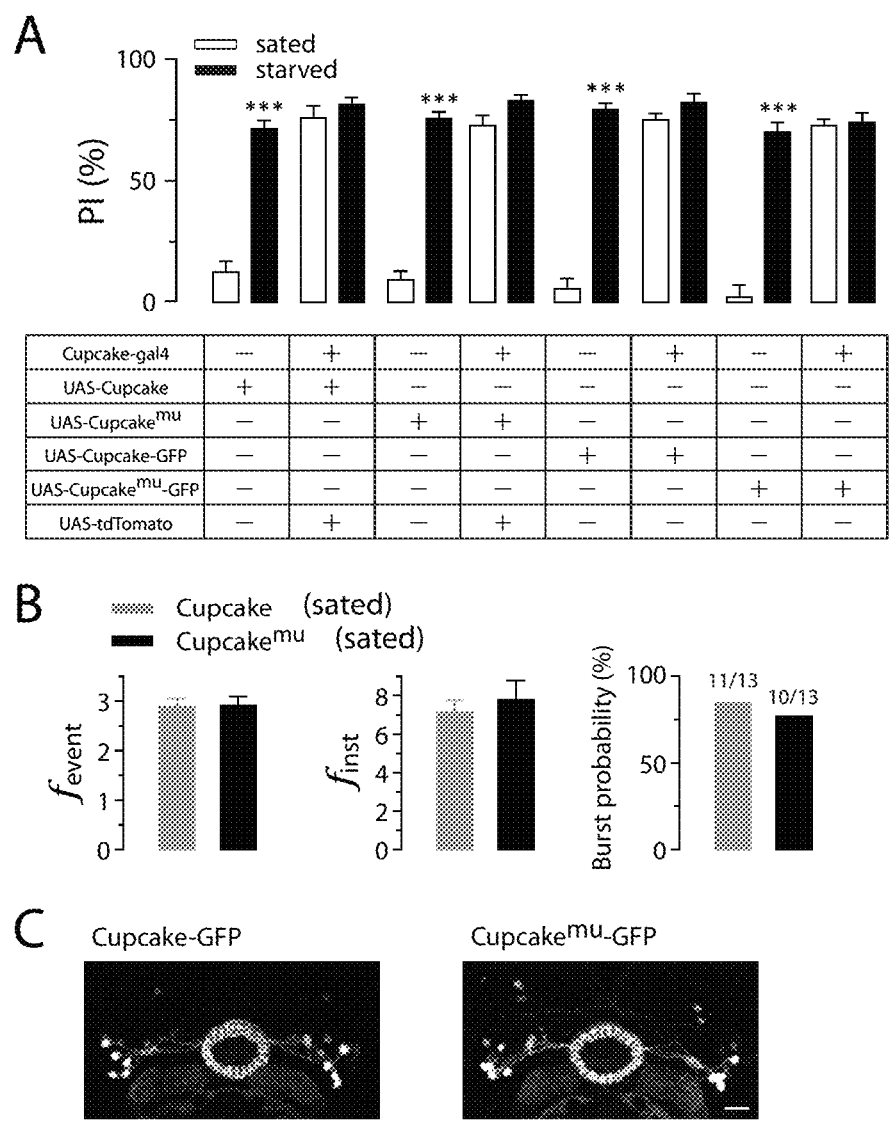

FIG. 23. Leak current generated by dSLC5A11 is not required for hunger-driven food choice behavior and neuronal excitability. (A) Behavior responses of 4-hr (sated) or 22-hr (starved) food deprived flies carrying UAS-cupcake (dSLC5A11) or UAS-cupcake$^{mu}$ (dSLC5A11$^{mu}$), and control flies in the two-choice assay. Flies were given a choice between 50 mM D-glucose and 270 mM L-glucose (n=6-10). (B) Summary plot of action potential firing frequency and bursting probability in dSLC5A11 neurons of sated flies expressing wild type dSLC5A11 or mutant dSLC5A11$^{mu}$. $f_{event}$, event frequency. $f_{inst}$, instantaneous frequency. The numbers of bursting neurons out of the total number of recorded neurons are indicated above the bars. (C) Confocal images from the flies carrying UAS-cupcake-EGFP or UAS-cupcak$^{mu}$-EGFP showing normal morphology. ***P<0.001; error bars indicate SEM.

DETAILED DESCRIPTION OF THE DISCLOSURE

The present disclosure provides compositions and methods for identifying agents that can interfere with a nutrient sensing pathway involving dSLC5A11 (in *Drosophila*), a brain nutrient sensor that mediates hunger behavior, or its human homolog or homologs in other species. The present disclosure also identifies neurons in the brain that express dSLC5A11 and that are involved in mediating behavior associated with hunger.

The present disclosure identifies a gene in *drosophila*, designated dSLC5A11 (or cupcake). This gene encodes a sodium/solute cotransporter-like protein, which is structurally similar to mammalian sodium/glucose cotransporters (SGLTs) that transport sugar across the intestinal and renal lumen. The dSLC5A11 is prominently expressed in 10-13 pairs of R4 neurons of the ellipsoid body (EB) in the brain and functions in these neurons for selecting appropriate foods.

In one aspect, this disclosure provides cDNA sequence (SEQ ID NO:1) corresponding to dSLC5A11. In one embodiment, this disclosure provided deduced amino acid sequence (SEQ ID NO:2) of the polypeptide encoded by dSLC5A11 or the corresponding cDNA. In one embodiment, this disclosure provides all polynucleotides encoding the deduced amino acid sequence. In one embodiment, this disclosure provides RNA sequences corresponding to or complementary to the entire or part of the cDNA sequence or dSLC5A11. The sequence of SLC5A11 gene region is provided in SEQ ID NO:3 and the sequence of SLC5A11 extended gene region is provided in SEQ ID NO:4.

In one aspect, this disclosure provides cells into which have been introduced polynucleotides which encodes for a protein of SEQ ID NO:2. Such cells may be *drosophila* cells, human cells or cells from any other species, cells in vitro (such as in culture) or cells in vivo (such as in a transgenic fly or another animal).

In one aspect, this disclosure provides a method for assessing whether a test agent enhances the capability of *drosophila* mutants (dSLC5A11) to preferentially intake metabolizing sugar (such as D-glucose) when starved. In one embodiment, the assessment is carried out in flies after appropriate periods of starvation (such as from 5 to 24 hours) and all integers therebetween, and administration of the test agent. Their food choice behavior is then assessed as further described herein. For example, flies may be presented with a choice between X mM D-glucose versus 2× to 5×mM L-glucose, the latter being sweeter due to the higher concentration of the sugar. Agents identified from this test can then be tested further to determine effectiveness in humans. In one embodiment, the identification of agents that can affect taste independent nutrient selection can be done by further screening via using mutants that contain a human homolog of dSLC5A11.

In one aspect, this disclosure provides a method for identifying human homolog of the *Drosophila* dSLC5A11 gene. To identify the human homolog, structurally similar SGLTs can be used to create transgenic flies. For example, cDNA sequences of the SGLT1, SGLT2, SGLT3, SGLT4, SGLT5, and SGLT6 can be used. These can be cloned into a *Drosophila* expression vector by routine molecular biology techniques. Such vectors are commercially available. The vector is then introduced into a *Drosophila* embryo resulting in the generation of transgenic flies. The vector can be introduced at random locations or selected locations by homologous recombination.

The transgenic flies are then screened to identify those which are the functional homolog of dSLC5A11. This can be done by evaluating the flies for their preference for metabolizing sugar. For example, a candidate human homolog of the dSLC5A11 can be introduced into fruit flies which are deficient in dSLC5A11. If the insertion results in rescue of the function—such as regained ability to preferentially intake D-glucose upon starvation—the inserted polynucleotide would then be deemed to encode for a potential functional homolog of dSLC5A11. This test is further described in Example 2. Upon identification of the functional homolog of dSLC5A11, the flies with the functional homolog can be used for a screening assay for agents that affect the preference for metabolizing sugars i.e., for agents that can affect taste independent nutrient selection.

In one aspect, this disclosure provides a method for assessing whether a test agent enhances or, alternatively, diminishes the capability of *drosophila* carrying a human homolog of dSLC5A11 to preferentially intake metabolizing sugar (such as D-glucose) when starved. In one embodiment, the assessment is carried out in flies after appropriate periods of starvation (such as from 5 to 24 hours) and all integers therebetween, and administration of the test agent. Their food choice behavior is then assessed as further described herein.

In certain embodiments, the disclosure includes genetically modified fruit flies and methods of making them. In certain embodiments, the endogenous *D. melanogaster* gene dSLC5A11 may be replaced with a mammalian homolog. In certain embodiments, the mammalian homolog is a human homolog. For example, the human homolog may be hSGLT1, hSGLT2, hSGLT3, hSGLT4, hSGLT5, hSGLT6 (hSGLT) and any other human gene encoding a sugar/glucose co-transporter or a sodium solute co-transporter (SLC5A) and the like. Thus, the disclosure includes humanized fruit flies. Details on the SLC5A family of genes can be found in Wright E M. 2004. Eur J Physiol. 447:510-518, the disclosure of which is incorporated herein by reference. The sequences for these genes can be obtained from Genbank. For example, the *Homo sapiens* Na+/glucose cotransporter (SGLT1) gene, complete cds sequence has a GenBank accession no.: AH005284.1. The *Homo sapiens* mRNA for sodium-glucose cotransporter (SGLT2 gene) has a GenBank accession no.: AJ133127.1.

Any suitable method for experimentally modifying a fruit fly genome/chromosome can be adapted to make *Drosophila* flies comprising a replacement of its endogenous dSLC5A11 gene with a mammalian homolog, and many such techniques are known in the art. For example, in an embodiment, the disclosure includes making a targeted replacement of *D. melanogaster* dSLC5A11 using a segment of DNA comprising a human homolog to replace the dSLC5A11 gene. The dSLC5A11 gene can be replaced with a human homolog gene by methods including homologous recombination, P element-induced gap repair, a phiC31 integration system, site-specific integrase-mediated repeated targeting (SIRT) and long range SIRT, 1- or 2-step captured segment exchange approaches, Ends-In Gene Targeting or Ends-Out Gene Targeting approaches, or any other suitable methods.

In one embodiment, this disclosure provides a method of screening one or more test agents for their ability to rescue the impaired functioning of dSLC5A11 mutant or a mutant of a mammalian or human homolog thereof. The term "dSLC5A11 mutant" is used herein to indicate a *drosophila* organism or cell wherein the dSLC5A11 gene has at least one mutation such that mutant does not show normal feeding behavior upon starvation. For example, the mutant may not show the normal behavior of preference for metabolizing sugar when starved. The method comprises providing flies that have a mutation in dSLC5A11 (or a human or mammalian homolog thereof, such as a SGLT) such that the flies do not show a preference for D-glucose when starved. Such flies are exposed to the test agents and then evaluated for food choice behavior, evaluation of biochemical characteristics (such as expression of dSLC5A11—including quantitation of transcript or dSLC5A11 protein), electrophysiological properties (such as electrical activity of dSLC5A11 neurons).

In one embodiment, flies can be evaluated for altered feeding behavior in the presence of test agents. The data presented herein demonstrates that activation of dSLC5A11 neurons stimulates feeding behavior. Thus, test agents may be screened to determine if the presence of any test agent inhibits (or in the alternative stimulates) enhanced feeding behavior upon activation of the dSLC5A11 neurons. In one embodiment, the dSLC5A11 neurons are identified by using tissue specific drivers or dSLC5A11 driver that can be coupled to expression of a detectable marker—such as a fluorescent marker.

In one embodiment, the dSLC5A11 neurons are activated by starvation. In one embodiment, the dSLC5A11 neurons are activated by expressing NaChBac (Bacterial channel) or TrpA1 (which is a heat activated channel). NachBac is a bacteria sodium channel. When Nachbac is expressed in given neurons, it allows the influx of cations and therefore, action potentials. As consequence, the neurons become activated. TrpA1 is a heated-activated trp channel. When TrpA1 is expressed in given neurons, it permits the influx of cations when it is exposed to a range of heat. Similarly, other activators of neuronal activity coupled to dSLC5A11 driver could be used. This generates action potentials and the neurons become activated. Feeding behavior can be evaluated by any one of several known methods. For example, feeding behavior may be evaluated by total consumption of food, food choice assays, food seeking assays (such as four-field arena assays), rate of proboscis response reflex (PER) assays, or neuronal excitability characteristics, including potassium current generated by KCNQ channel. In some instances, the feeding behavior, the biochemical properties or the electrophysiological properties are compared to wild type flies may be compared to a control in the absence of the agent or may be compared to wild type flies.

In one embodiment, the excitability of dSLC5A11 neurons can be evaluated. Excitability of neurons as used herein means one or more of the electrophysiological characteristics of a cell, including, but not limited to, spontaneous activity, action potentials (amplitude, frequency, etc.), burst activity, evaluation of any particular current, single channel recordings and the like. As described further in Example 3 herein, we observed that in wild type flies, spontaneous activity of these neurons is increased under conditions of starvation. However, this increase in spontaneous activity is abolished in dSLC5A11 mutants. Thus, various test agents can be screened to determine their ability to affect (either enhance or reduce, or qualitatively affect) the electrical activity of dSLC5A11 neurons in wild type flies or in dSLC5A11 mutants. For example, agents may be tested to see if spontaneous activity of the neurons upon starvation can be restored in the dSLC5A11 mutants. In one embodiment, burst activity may be evaluated in addition to, or as an alternative to spontaneous activity. In one embodiment, action potentials may be evaluated. The electrical activity of neurons can be recorded by routine patch clamp recordings—including whole cell patch clamp, single channel recording, and the like.

In one embodiment, various agents may be tested to identify agents that inhibit the suppression of potassium current generated by dKCNQ in response to activation of dSLC5A11 neurons (such as by expression of NaChBac or TrpA1). Thus, for example, isolated *D. melanogaster* brains may be used for activating dSLC5A11 neurons and the dKCNQ current may be measured in the presence of various agents. Activation of dSLC5A11 neurons from wild type flies should result in suppression of dKCNQ-mediated current. If such suppression is lacking in the presence of a test agent, then that agent is identified as a candidate for suppressing hunger related behavior.

We have identified agents that can stimulate or suppress the activity of dSLC5A11 neurons. The expression of Nach-Bac, a bacteria sodium channel, in these neurons potentiates neuronal excitability, thereby causing the animals to exhibit hunger-related or food-seeking behavior. Conversely, the expression of Kir2.1, an inwardly rectifying K+ channel, in dSLC5A11 neurons suppress neuronal excitability. This treatment renders the animals to feel satiated. These are illustrative examples that exogenous agents can stimulate and suppress dSLC5A11 neuronal activity, and feeding behavior.

The properties of dSLC5A11 neurons may be evaluated by obtaining these neurons in culture, in *drosophila* brain slices, in isolated *drosophila* brains or in intact flies.

In one embodiment, this disclosure provides a method for identifying agents that interfere with hunger sensation: providing dSLC5A11 neurons of *D. melanogaster* (in as isolated neurons, isolated brains or brain slices, or in intact animals) which are capable of being activated; activating the neurons in the presence or absence of a test agent; c) evaluating feeding behavior of *D. melanogaster* and/or electrophysiological characteristics of the neurons, wherein a change in the feeding behavior or one or more of the characteristics compared to the feeding behavior or characteristics in the absence of the test agent is indicative of the presence of an agent that can interfere with hunger sensation.

In one embodiment, this disclosure provides a method for generating transgenic fruit flies which can be used to identify agents affecting taste independent nutrient selection comprising: introducing a candidate human sequence encoding a sodium solute co-transporter or a sodium glucose co-transporter into a *drosophila* mutant which does not have a functional dSLC5A11, and identifying flies in which the function of preferential nutrient intake upon starvation is restored.

In one embodiment, this disclosure provides a *D. melanogaster* mutant comprising a non-functional dSLC5A11 gene, as measured by a lack of ability to preferentially intake metabolizing sugar upon starvation.

In one embodiment, this disclosure provides a method for generating transgenic fruit flies which can be used to identify agents affecting taste independent nutrient selection comprising: a) introducing into *Drosophila* embryos a polynucleotide comprising a *Drosophila* expression vector and a human sequence encoding a human/sugar co-transporter (hSGLT); b) cross breeding the flies from a) with *Drosophila* mutants carrying a mutation in the dSLC5A11 (such that the mutant does not have a functional dSLC5A11) to generate flies in which the hSGLT is expressed in only those cells which express SLC5A11; c) identifying flies from b) which exhibit feeding behavior in which the flies show a preference for D-glucose when starved. In one embodiment, transgenic flies generated by this method are also provided.

In one embodiment, this disclosure provides a method for identifying agents that affect food choice behavior in fruit fly *D. melanogaster* comprising the steps of subjecting the flies wild type or dSLC5A11 mutant flies to a starved state and then allowing the fly access to metabolizing and non-metabolizing sugars after administration of one or more test agents, and determining if preference for metabolizing sugar is affected.

In one embodiment, this disclosure provides the cDNA for dSLC5A11. In one embodiment, this disclosure provides cells comprising the cDNA. In one embodiment, the present disclosure provides *drosophila* or other organisms comprising cells comprising cDNA for dSLC5A11 or a protein encoded by the cDNA.

The present disclosure includes polynucleotides and amino acid sequences which comprise or consist of any of the sequences described herein. All polynucleotides encoding all of the amino acids sequences are included in the scope of this disclosure. The polynucleotides include their reverse complements and RNA equivalents. The disclosure includes all contiguous segments of the polynucleotides and amino acid sequences described herein, from two amino acids or two nucleotides, up to and including their full lengths. Additional nucleotides or amino acids can be added, and conservative amino acid substitutions, insertions and deletions, can be made and tested to determine whether or no they affect the function of the protein in an undesirable way.

Example 1

Material and Methods

Fly Strains

Flies were reared in standard cornmeal-molasses medium at 25° C. with 12:12 D:L cycles. The standard laboratory line Canton-S(CS) was used as wild-type control. dSLC5A11$^1$ (CG8451, cupcake, stock #22498: $y^1$ $w^{67c23}$; P{EPgy2}CG8451$^{EY21708}$), dSLC5A11$^2$ (stock #6768: y w; P{Mae-UAS.6.11}CG8451$^{UY1824}$), and deficiencies (stock #9705 and #9706) uncovering the dSLC5A11 locus were obtained from the Indiana Bloomington stock center. dSLC5A11$^{1\ revertant}$ flies were generated by mobilizing the P element with Δ2-3 transposase. Precise excision lines were identified by absence of mini-white+eye color and confirmed by PCR genotyping and sequencing.

Transgenic Lines

P$_{dSLC5A11}$-GAL4 was made by cloning a 1.1-kilobase (kb) portion of DNA sequence upstream of dSLC5A11 into pCasper4-AUG-GAL4X. UAS-dSLC5A11 was generated by cloning the cDNA sequence of dSLC5A11 into pUAST. Transgenic flies were generated by Bestgene, Inc.

Two-Choice Assay

Feeding assays were performed as previously described[6] using 50 flies per two-choice arena. Briefly, ~50 4-8 days old male flies were starved in an empty vial with wet Kim wipe for 5 or 18 hours, and then given a choice between two sugars, or a sugar and plain agar for 2 hours. Food preference was determined as percent preference index (PI %) by scoring the abdomen color of each fly:

% PI=(#eaten food1+0.5×#eaten both)−(#eaten food2+0.5×#eaten both)]/(total #flies eaten)

Figure 10:
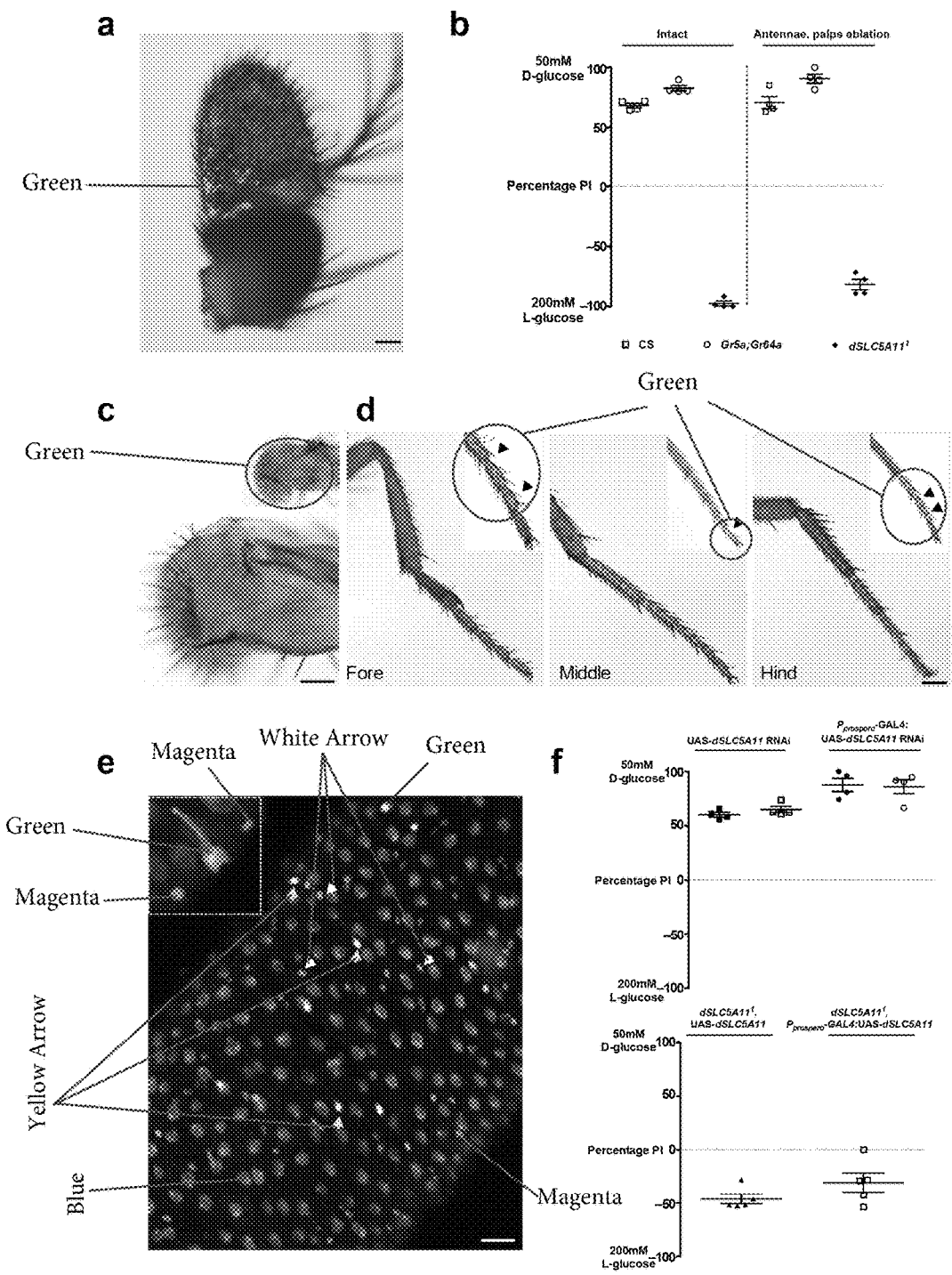
FIG. 10. The expression of dSLC5A11 outside the brain is not required for taste-independent nutrient selection. (a) Z-stack image of the antenna of a fly carrying P$_{dSLC5A11}$-GAL4 and UAS-CD8GFP, visualized by native GFP fluorescence in green. Scale bar: 20 m. (b) The food choice behaviors of CS, Gr5a;Gr64a and dSLC5A11$^1$ flies with or without olfactory appendages (antennae and maxillary palps) were examined in the two-choice assay with 200 mM L-glucose versus 50 mM D-glucose. n=4. Two-way ANOVA with Bonferroni test indicates that there is no significant difference between the indicated genotypes with and without olfactory appendages for food choice behavior. (c-d) The labellum (c) and tarsi (d) of a fly carrying P$_{dSLC5A11}$-GAL4 and UAS-mCD8GFP visualized by TO-PRO (DNA labeling) in gray and native GFP fluorescence in green. These z-stack (c) and single representative (d) images were compared to those of Gr5a-GAL4;UAS-GFP (insets), which labels a subset of gustatory sensory neurons (arrowheads). Scale bar: (c) 50 m and (d) 100 m. (e) The image of a portion of the anterior midgut of a fly carrying $P_{dSLC5A11}$-GAL4 and UAS-GFP, visualized by anti-Prospero in magenta (white arrowheads), anti-GFP in green (yellow arrowheads) and TO-PRO (DNA) in blue. The co-labeling of prospero and GFP in a cell was illustrated in the inset. Thus, $P_{dSLC5A11}$-GAL4 is expressed in a subset of Prospero+enteroendocrine cells in the gut. Scale bar: 20 m. (f) Top, the food choice behaviors of flies in which two independent UAS-dSLC5A11 RNAi lines (filled and unfilled) were expressed in enteroendocrine cells by $P_{prospero}$-GAL4 were determined in the two-choice assay with 200 mM L-glucose versus 50 mM Dglucose after 18 hours of starvation. Flies carrying UAS-dSLC5A11 RNAi lines without a driver were used as controls. n=4. ANOVA with Tukey test indicates that there is no significant difference between flies with knock-down of dSLC5A11 and controls for food choice behavior. Bottom, the food choice behaviors of dSLC5A11$^1$ mutants expressing UAS-dSLC5A11 in enteroendocrine cells by $P_{prospero}$-GAL4 were determined in the two-choice assay after 18 hours of starvation. dSLC5A11 mutants carrying UAS-dSLC5A11 alone were used as controls. n=5. One-way ANOVA with Tukey test showed there is no significant difference between control and dSLC5A11 mutants with UAS-dSLC5A11 expression in the enteroendocrine cells.

All sugars, except for L-glucose (Carbosynth), were from Sigma. For FIG. 1c, 10 mM phlorizin (Sigma) was added to warm agar with or without sugar. For the experiments in the dark, individual plates were wrapped in aluminum foil and then placed in a dark drawer while tested flies were making a choice between the two substrates. For the neural silencing experiments, flies bearing UAS-Kir2.1, $P_{tubulin}$-GAL80$^{ts}$, and a GAL4 driver were treated as described[17]. These flies were raised at 18° C., incubated at 29° C. for 40 hours, starved at 29° C. for next 18 hrs and then tested in the two-choice assay at room temperature. For a negative control, the flies were raised and starved at 18° C., and tested at room temperature. Because metabolism is slower at 18° C. than at 25-29° C., the flies at 18° C. needed to be starved for a longer period. Thus, we determined that the 18 hours of starvation at 25-29° C. is equivalent to the 50-60 hours of starvation at 18° C. Also, see FIG. 11.

Hemolymph Glycemia and Glycogen Measurements

Glycogen and glycemia were measured as previously described[6]. For the prandial rise of hemolymph glycemia, flies were starved for 18 hours, and then fed with 100 mM glucose (with or without 10 mM phlorizin) for 15-20 minutes. Their hemolymph was immediately collected and measured.

Immunohistochemistry

Brains were fixed and stained with addition of a permeabilization step (10 mins with 0.5% Triton-X 100, 0.5% BSA in Phosphate buffered saline, PBS) for better antibody penetration into the central brain. Guts were immunostained as previously described[12,13] The following antibodies were used: mouse anti-bruchpilot at 1:20 (Developmental Studies Hybridoma Bank, NC82), mouse anti-Prospero at 1:10 (Developmental Studies Hybridoma Bank, MR1A) and rabbit anti-GFP IgG at 1:500 (Invitrogen, A-6455). Secondary antibodies were Alexa Fluor 555 goat anti-mouse IgG at 1:500 (Invitrogen, A-21425), Alexa Fluor 488 goat anti-rabbit IgG at 1:500 (Invitrogen, A-11070) and TO-PRO3 at 1:500 (Invitrogen, T3605) used for DNA labeling. Images were acquired using a Zeiss LSM 510, at 1.5 μm intervals with 1024×1024 or 512×512 resolution.

Photoactivatable GFP (PA-GFP)

Brains from <1 day old $P_{dSLC5A11}$-GAL4; UAS-C3PA homozygotes were dissected in the adult hemolymph buffer[11], immobilized onto a silicone gel plate with pins and visualized under a two-photon microscope using a 40× water immersion lens. Prior to photo-conversion, the low intensity fluorescence of the PA-GFP protein was visualized by the two-photon laser at 925 nm to identify the cells of interest. For photoconversion, the two-photon laser at 715 nm was applied repeatedly to their cell bodies for 60 cycles with 30-second intervals between cycles to allow diffusion of the photo-converted GFP protein. The converted PA-GFP protein was then visualized at 925 nm.

qPCR

Thirty brains of starved adult CS flies were dissected in PBS, and RNA was isolated with Trizol reagent (Invitrogen). 1 μg RNA was used to make cDNA using oligo dT primers. The expression of dSLC5A11 and GAPDH transcript was assayed by qPCR with a Biorad C1000 thermal cycler (CFX96 Real-Time System). Primers for dSLC5A11 were TGCTTCAAGATGCAACCAAG (forward) (SEQ ID NO:5) and TTGAAGTGCAAATGCTCAGG (reverse) (SEQ ID NO:6) and for GAPDH GAAATCAAGGCTAG-GTCG (forward) (SEQ ID NO:7) and AATGGGTGTCGCT-GAAGAAGTC (reverse) (SEQ ID NO:8). cDNA dilutions of 1/10, 1/100, and 1/1000 were used for each primer set to calculate the qPCR efficiency.

Dendrogram

We used the dSLC5A11 sequence to blast the Drosophila and human genomes, and identified 14 Drosophila genes and 12 human genes that are homologous to dSLC5A11. We used clustalW (ebi.ac.uk/Tools/msa/clustalw2/) to conduct sequence alignment with the 15 dSLC5A and 12 hSLC5A, and formatted the guide tree file. We then used FigTree (tree.bio.ed.ac.uk/software/figtree/) to plot the dSLC5A/hSLC5A radial tree.

Statistics

Figure 2:
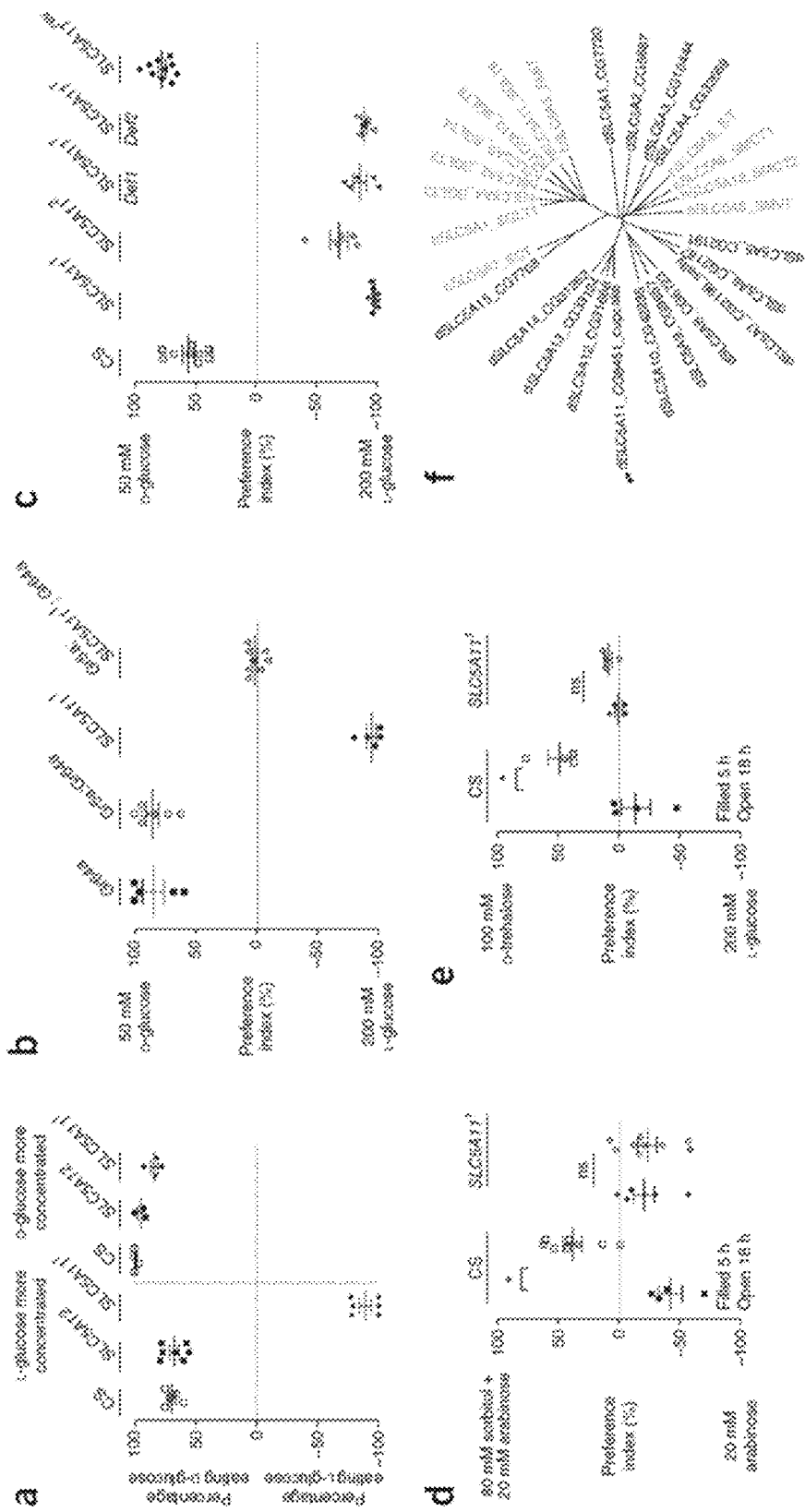
FIG. 2. dSLC5A11, a member of the *Drosophila* sodium/solute cotransporter family, is required for taste-independent nutrient selection. (a) 18-hour starved dSLC5A11$^1$ mutants and controls were given a choice of 200 mM L-glucose v. 50 mM D-glucose (left), or 200 mM D-glucose v. 50 mM L-glucose (right) in the two-choice assay. n=3-7. (b) The food choice behaviors of 18-h starved Gr5a; dSLC5A11$^1$; Gr64a triple mutants and controls were determined n=5-8. (c) The food choice behaviors of different dSLC5A11 allelic combinations and controls were measured after 18 hours of starvation. n=5-10. (d-e) The food choice behaviors of dSLC5A11$^1$ and CS control were measured with (d) sorbitol (tasteless)+arabinose v. arabinose (non-nutritive), n=4, (e) D-trehalose v. L-glucose, n=9. (f) Dendogram of the *Drosophila* and human sodium/solute cotransporter families. Double arrowheads indicate dSLC5A11 (CG8451, cupcake). Asterisk, P<0.001 (one-way ANOVA, Tukey test).
Figure 9:
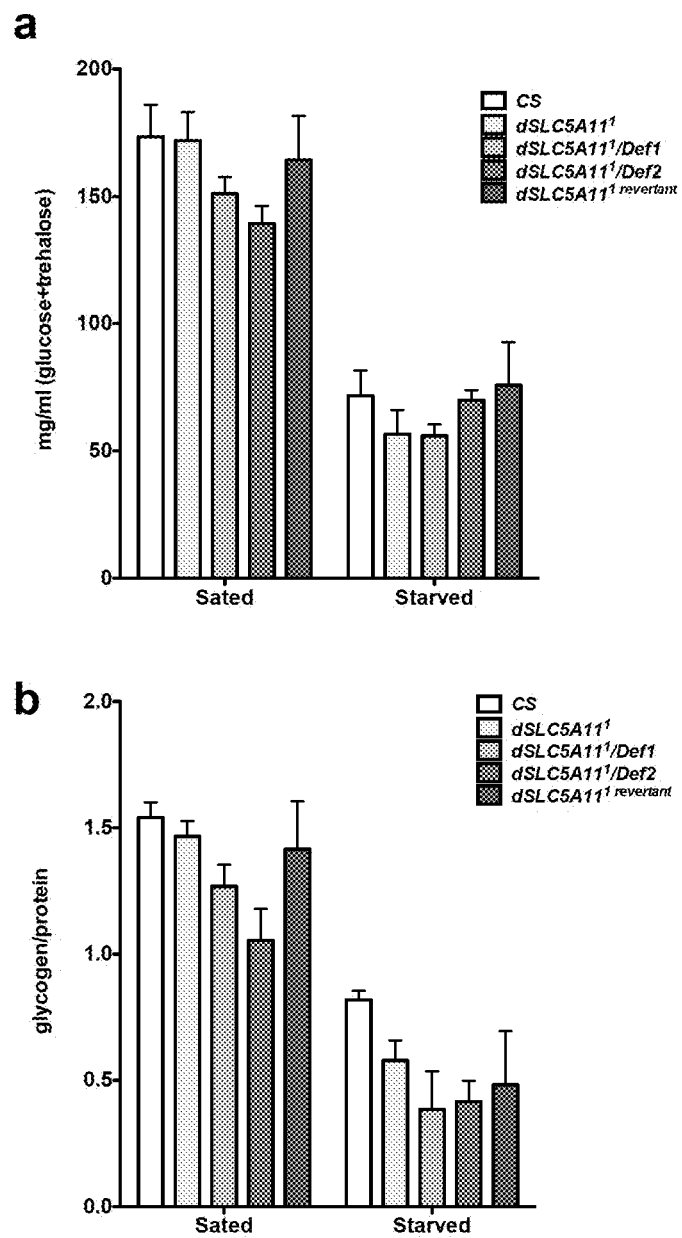
FIG. 9. dSLC5A11 mutants have normal hemolymph glycemia and glycogen stores. (a) Measurements of the hemolymph glycemia and (b) the glycogen stores of sated and starved dSLC5A11 mutants or controls were determined according to standard protocols (see Methods). The sated and starved flies were food-deprived for 5 and 18 hours. n=9-16. Two way ANOVA with Bonferroni test indicates that there is no significant difference in hemolymph glycemia and glycogen levels between dSLC5A11 mutant and control flies in sated or starved state.

GraphPad Prism software was used for all graphs and statistical analysis. All experiments were done with experimental and control genotypes in parallel. Data represent multiple independent experiments. Error bars are SEM. One-way or two-way ANOVA with Tukey or Bonferroni posthoc-test or student t-test (for qPCR) were used according to the number of conditions and genotypes. In FIG. 2a (left), 2b-c, 3c-d the food choice behavior of dSLC5A11 mutant and knock-down flies was significantly different from that of controls, P<0.0001. In FIGS. 9a and b, there is no significant difference in hemolymph glycemia between dSLC5A11 mutant and control flies according to ANOVA.

Results

Figure 1:
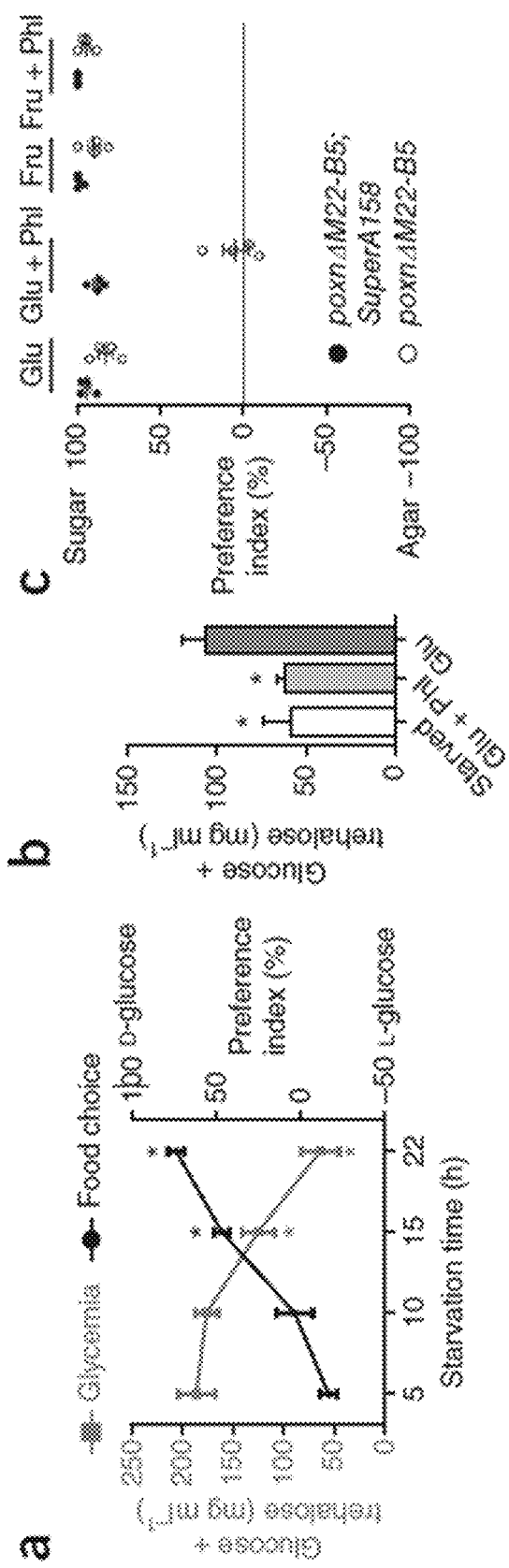
FIG. 1. A prandial rise in hemolymph glycemia is required for appropriate food choice behavior in starved flies. (a) The hemolymph glycemia (grey, n=10-12) and food choice (black, 50 mM D-glucose versus 200 mM L-glucose, n=4-8) of starved wild-type (Canton-S) were measured. (b) The hemolymph glycemia of 18-hour starved flies was measured after feeding 100 mM glucose with or without 10 mM phlorizin for 20 minutes. n=10-12. (c) The food choice behaviors of 18-h food deprived poxnΔM22-B5 (unfilled circles) and poxnΔM22-B5; SuperA158 control (filled circles). These flies were given a choice between agar containing 100 mM sugars with or without 10 mM phlorizin and plain agar (Glu, Glucose; Fru, Fructose; Phl, Phlorizin). n=4. Asterisk, P<0.001 (one-way ANOVA, Tukey test).

Eating behavior is controlled by multiple factors including food palatability and nutritional needs. External chemosensory taste receptors primarily detect palatable food, but animals lacking taste receptors can still develop a preference for sugars based on their nutritional value. Drosophila melanogaster can detect nutritive (i.e. metabolizable) sugars in the absence of peripheral sugar receptors. This taste-independent nutrient selection pathway is activated when the internal energy reservoir is depleted. We found that food choice behavior correlates strongly with a decrease in sugar (glucose and trehalose) levels in the hemolymph (FIG. 1a). Specifically, flies that had been food-deprived for approximately 15 hours (the length of time that leads to a dramatic fall in hemolymph sugar levels) selected the nutritive D-glucose over the non-metabolizable L-glucose. This suggests that the hemolymph sugar might be the postingestive cue that drives feeding behavior independently of gustatory inputs.

Figure 4:
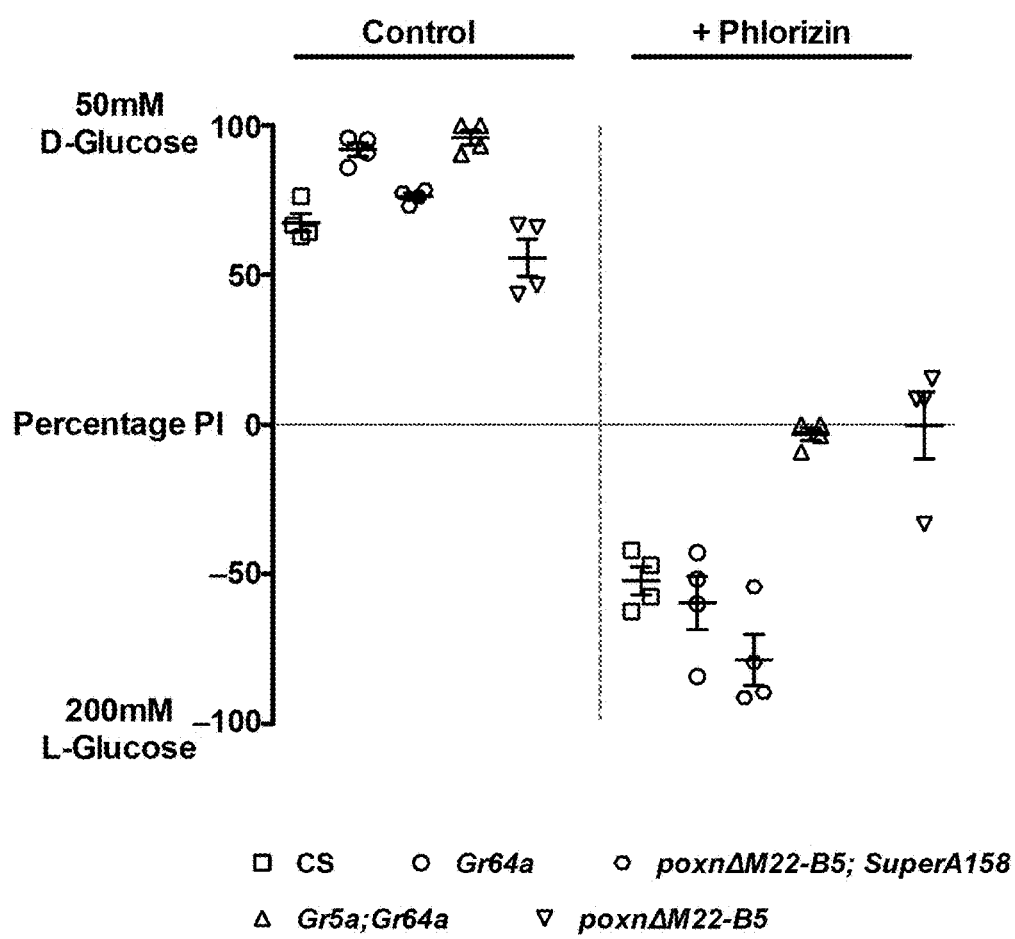
FIG. 4. Preventing the prandial rise in hemolymph glycemia impairs the taste-independent nutrient selection. The food choice behaviors of different mutants were measured in the two-choice assay with 200 mM L-glucose+phlorizin versus 50 mM D-glucose+phlorizin after 18 hours of food deprivation (right). The experiments without the addition of phlorizin to glucose were used as controls (left). Gr5a; Gr64a and poxnΔM22-B5 mutants failed to discriminate between Lglucose+phlorizin and D-glucose+phlorizin, whereas others chose the more concentrated (sweeter) L-glucose. n=4. Two-way ANOVA with Bonferroni test confirmed that the addition of phlorizin to sugars has significant effects on food choice behavior, P<0.0001.

To establish a causal link between hemolymph sugar levels and taste-independent food choice behavior, we investigated the possibility that blocking the entry of glucose into the hemolymph interfered with the induction of this behavior. Phlorizin, a drug that blocks the transport of glucose from the intestinal lumen into the blood in mammals, was used to suppress the entry of glucose into the hemolymph in flies, thereby preventing a prandial rise in glycemia (FIG. 1b). In a two-choice assay, the "taste-blind" pox-neuro mutant (poxnΔM22-B5) that is insensitive to the taste of sugars, developed a preference to glucose over plain agar after 18 hours of food deprivation, but failed to consume glucose mixed with phlorizin (FIG. 1c). This is likely due to a failure of the phlorizin-laced glucose, which is not transported into the hemolymph, to activate the taste-independent nutrient selection pathway. By contrast, because phlorizin does not inhibit fructose transport, the taste-blind mutants were able to detect the nutritional value of fructose mixed with phlorizin (FIG. 1c). The control flies, pox-neuro mutants that carry a rescue transgene (poxnΔM22-B5;SuperA158), can distinguish glucose mixed with phlorizin from agar. Moreover, when given the choice between D-glucose mixed with phlorizin and a more concentrated (sweeter) L-glucose mixed with phlorizin, taste-blind (poxnΔM22-B5) and sugar-blind (GR5a;GR64a) mutants showed equal preference for these two enantiomers (FIG. 4). On the contrary, control flies chose the sweeter L-glucose because blockade of glucose transport promotes food selection based on gustatory information alone. These observations suggest that a prandial rise in hemolymph glucose would trigger the taste-independent nutrient selection pathway.

Figure 5:
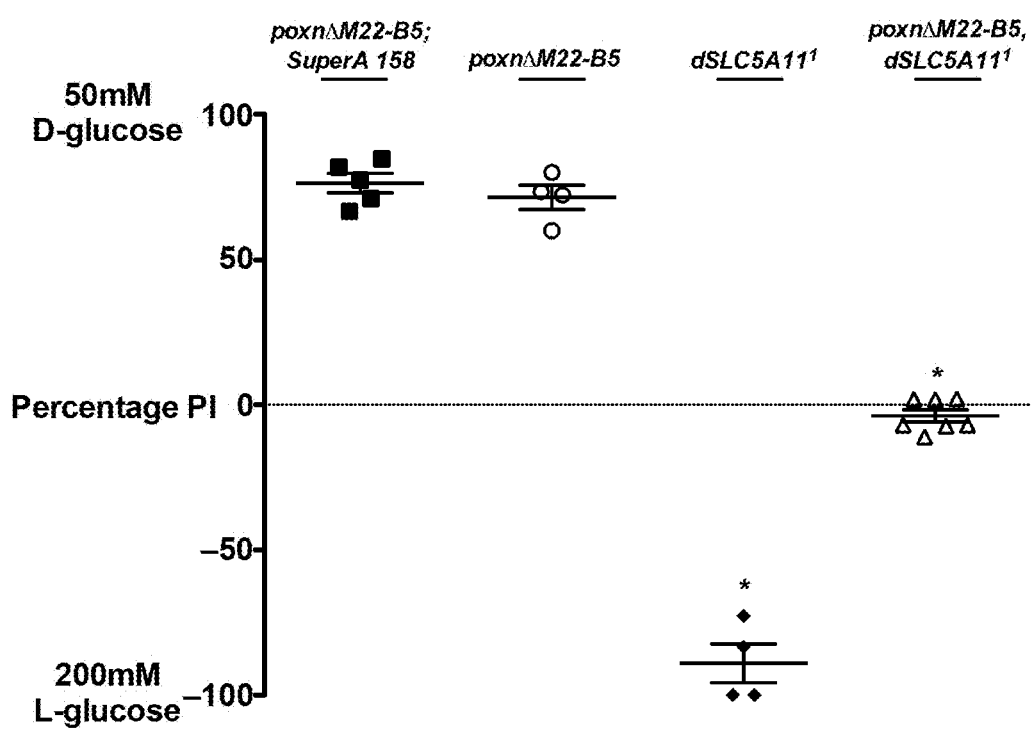
FIG. 5. Food choice defect in poxnM22-B5; dSLC5A11$^1$ mutants. The food choice behaviors of poxnM22-B5; dSLC5A11$^1$ double mutants and controls (poxnM22-B5; SuperA158, poxnM22-B5, and dSLC5A11$^1$) were measured in the two-choice assay with 200 mM L-glucose versus 50 mM D-glucose after 18 hours of starvation. n=4-7. Asterisk, P<0.001 (One-way ANOVA, Tukey test).

To investigate the genetic basis for this behavior, we screened for mutants that failed to exhibit a preference for a nutritive sugar (D-glucose) over a non-metabolizable sugar (L-glucose) when starved. Wild type flies showed no sugar preference when sated, but preferred D-glucose when starved. We identified one mutant that failed to choose D-glucose when starved, and made food choice based on the palatability alone. When D-glucose was more concentrated and presumably sweeter, this mutant preferred D-glucose to L-glucose; conversely, when L-glucose was more concentrated, the mutant chose L-glucose over D-glucose (FIG. 2a). The affected gene encodes a putative sodium/solute cotransporter protein, which we named Drosophila sodium/solute cotransporter-like 5A11 (dSLC5A11 and also cupcake). We speculated that the ability to detect sugar would be completely abolished in GR5a, dSLC5A11[1], and GR64a triple mutants. Indeed, these flies displayed equal preference for D-glucose and L-glucose (FIG. 2b), presumably because they had neither external sugar receptors that detect the palatability nor dSLC5A11 that allows flies to respond to the nutritional value of sugar. Consistent with this result, we found that poxnΔM22-B5; dSLC5A11[1] mutants were unable to develop a postingestive preference for nutritive D-glucose (FIG. 5).

Figure 6:
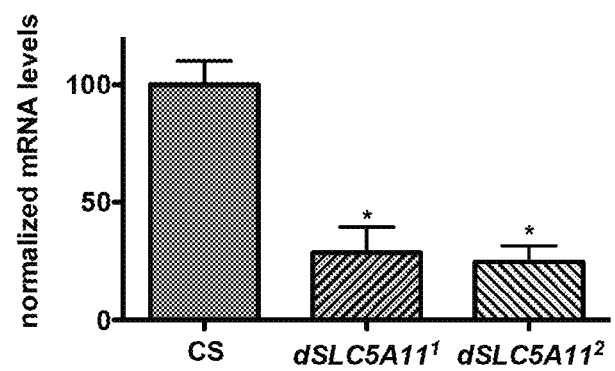
FIG. 6. dSLC5A11 mutants show a decrease in the dSLC5A11 transcript levels. Measurement of the dSLC5A11 mRNA transcripts in the brains of WT (CS), dSLC5A11$^1$ and dSLC5A11$^2$ mutant alleles by qPCR. The dSLC5A11 transcript levels in the mutants were normalized to those in controls and the relative abundance was calculated with respect to GAPDH. n=4. Asterisk, P<0.001 (One-way ANOVA, Tukey test).
Figure 7:
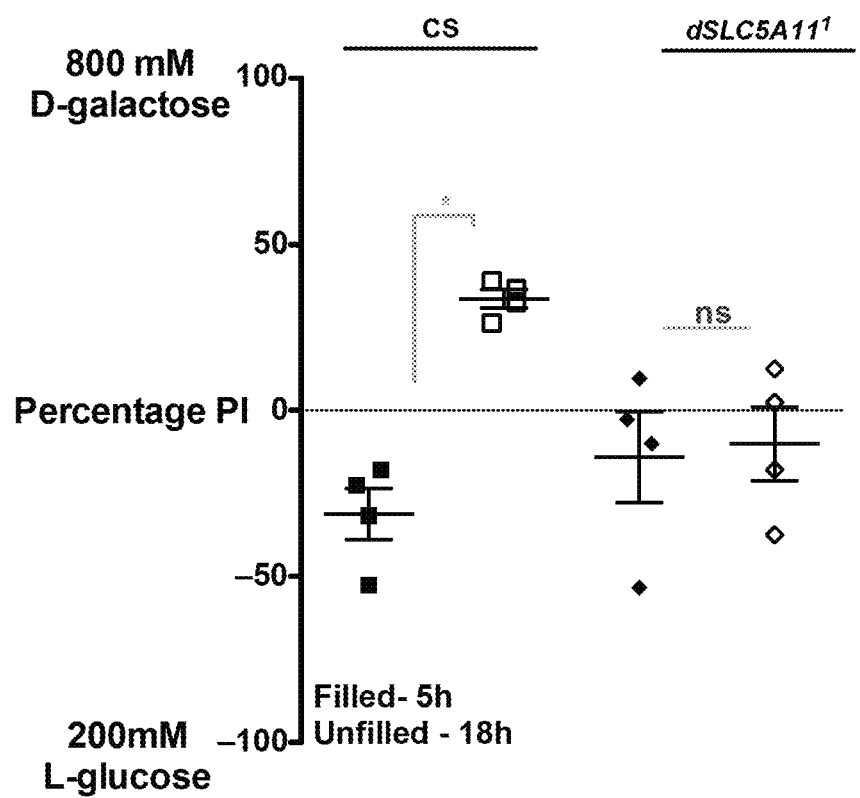
FIG. 7. Failure of dSLC5A11$^1$ to select D-galactose upon starvation. The food choice behaviors of dSLC5A11$^1$ mutant and CS control were measured in the two choice assay with 800 mM D-galactose versus 200 mM L-glucose. n=4. Asterisks, P<0.001 (One-way ANOVA, Tukey test).
Figure 8:
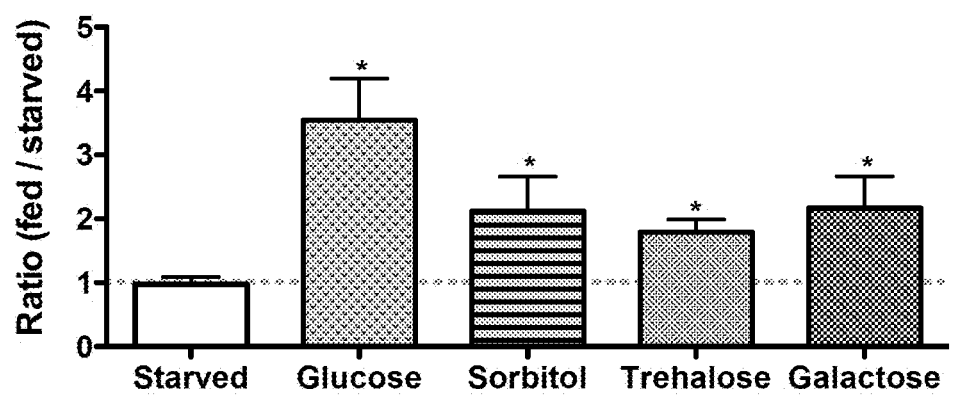
FIG. 8. The prandial rise in hemolymph glycemia upon feeding different sugars. Measurements of the hemolymph sugar levels of flies that were starved for 18 hours and then fed with the indicated sugars were conducted 90 minutes after sugar feeding. n=5-11. Asterisk, P<0.001 (One-way ANOVA, Tukey test with respect to starved flies).

To ensure that this phenotype is caused by the mutation in the dSLC5A11 locus, we generated fly strains carrying the dSLC5A11[1] allele in trans to two independent deficiencies uncovering the locus. These strains were phenotypically indistinguishable from dSLC5A11[1] homozygotes (FIG. 2c). By contrast, flies in which the transposable element was precisely excised from the dSLC5A11 locus exhibited a normal preference to D-glucose when starved. We later identified another mutation, designated dSLC5A11[2] that had a phenotype similar to that of dSLC5A11[1] (FIG. 2c). The quantitative PCR analysis showed that the dSLC5A11 transcript was significantly reduced in the brains of dSLC5A11[1] and dSLC5A11[2] homozygotes (FIG. 6). The food-deprived dSLC5A11 mutant also failed to exhibit the shift in preference for other nutritive sugars including sorbitol, trehalose and galactose, which increase hemolymph glycemia upon ingestion (FIG. 2d, e and FIG. 7, 8).

dSLC5A11 belongs to a large sodium/solute cotransporter (SLC5A) family, members of which are highly homologous to the human SLC5As such as iodide, monocarboxylate and multivitamin cotransporters (FIG. 2f). The human sodium/glucose cotransporters (SGLTs) have a distinct clade, yet hold approximately 24%-30% amino acid identities to the Drosophila SLC5As. Some mammalian SLC5As, including SGLT1, function in the brush-border cells of the small intestine to absorb glucose from the intestinal lumen by using the sodium electrochemical gradient. We therefore hypothesized that dSLC5A11 could have a similar function and that its mutation would disrupt glucose transport; this could adversely affect circulating sugar levels that lead to a defect in taste-independent food preference. However, we found that the hemolymph glycemia as well as glycogen stores in dSLC5A11 mutants were indistinguishable from those in controls (FIG. 9a, b). This suggests that dSLC5A11 regulates feeding behavior by a different mechanism.

Figure 3:
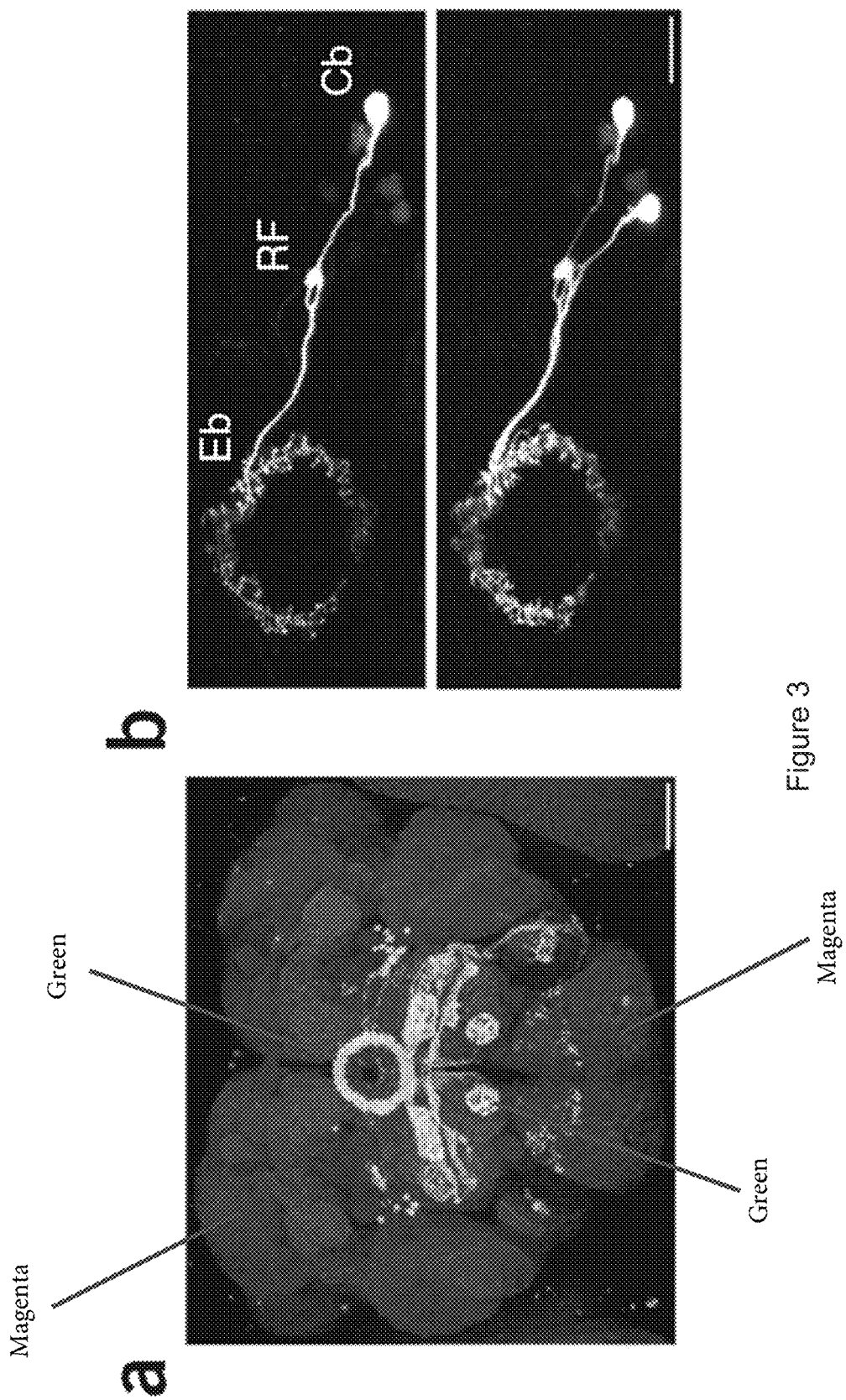
FIG. 3. A subset of EB R4 neurons is required for taste-independent nutrient selection. (a) Z-stack image of the adult brain. P$_{dSLC5A11}$-GAL4::UAS-mCD8GFP stained with anti-GFP antibody in green and the neuropil marker, nc82, in magenta. Scale bar: 50 μm. (b) Single- (top) or two-cell (bottom) labeling of the EB R4 neurons of P$_{dSLC5A11}$-GAL4::UAS-PA-GFP. Cb, cell body; RF, large-cell/fan-shaped body tract. Scale bar: 20 μm. (c) The food choice behaviors of 18-hr starved flies in which dSLC5A11 was knocked-down in different subsets of R-cells by using two independent UAS-dSLC5A11 RNAi lines and R-cell specific drivers. Flies carrying UAS-dSLC5A11 RNAi line alone were used as a control. n=4-7. (d) The food choice behaviors of 18-hr starved dSLC5A11$^1$ mutants carrying UAS-dSLC5A11 in different subsets of EB neurons were measured. dSLC5A11$^1$ mutants bearing UAS-dSLC5A11 alone were used as a control. n=4-9. (e) The food choice behaviors of 18-hr starved flies in which different EB R neurons were silenced by incubating them at 29° C. (filled) or were left active at 18° C. (unfilled) were measured. Flies carrying UAS-Kir2.1; P$_{tubulin}$GAL80$^{ts}$ without a driver were used as a control. n=4-7. Asterisk, P<0.0001 (Two-way ANOVA, Bonferroni test).
Figure 3:
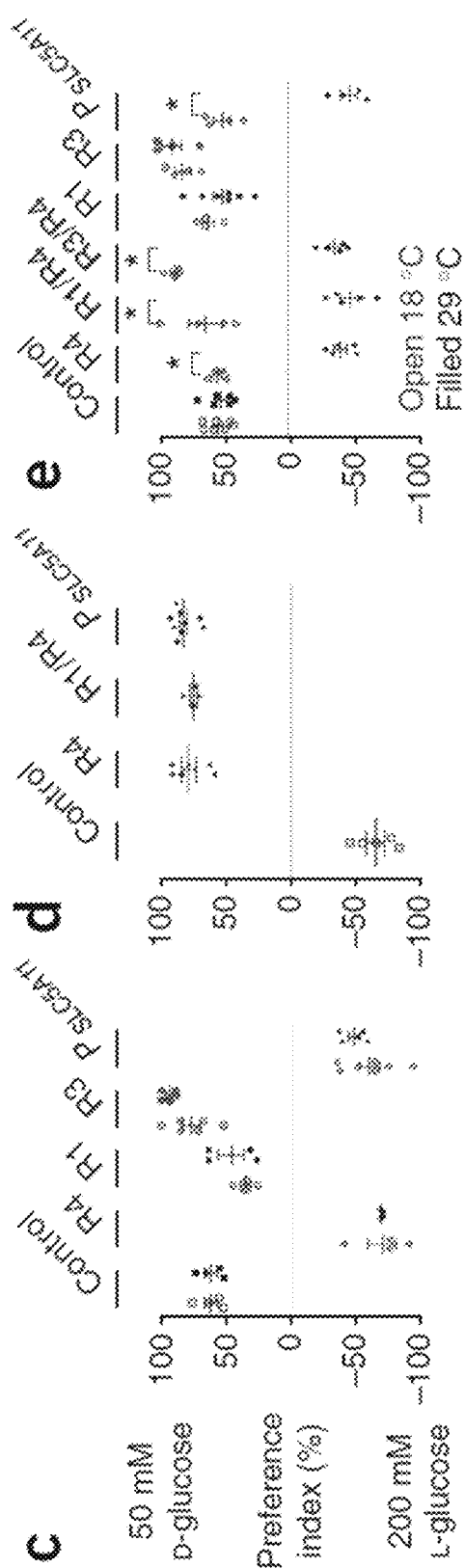

To determine the expression pattern of dSLC5A11, we engineered transgenic flies that carry the dSLC5A11 promoter, $P_{dSLC5A11}$-GAL4, driving UAS-mCD8GFP. Surprisingly, we found few labeled neurons in the brain of a transgenic fly. Notably, approximately 10-13 pairs of R4 neurons of the ellipsoid body (EB) showed prominent GFP expression (FIG. 3a). To further analyze the projection patterns of these EB R4 neurons, we labeled a single R4 neuron in a fly carrying photoactivatable GFP (UAS-C3PA-GFP) under the control of $P_{dSLCA11}$-GAL4 driver. The labeled R4 neuron extended its neurite along the RF tract, formed bleb-like termini and innervated the outer ring of the EB, ramifying its processes over the entire circumference of the ellipsoid body ring (FIG. 3b).

Moreover, the transgene was expressed in a few populations of olfactory sensory neurons (FIG. 3a and FIG. 10a). However, dSLC5A11 in these neurons is unlikely to have a relevant role, as the olfactory organs were dispensable for taste-independent food preference (also FIG. 10b). We also observed the expression in a small number of neuronal fibers in the subesophageal ganglion, but did not find any GFP labeling in the external taste organs (FIG. 10c, d). A subset of Prospero-positive, enteroendocrine cells in the anterior midgut were labeled in $P_{dSLCA11}$-GAL4 (FIG. 10e). However, dSLC5A11 in these cells are not required for taste-independent food preference (FIG. 10f). In contrast, dSLC5A11 is required in EB R4 neurons for this behavior. Flies with dSLC5A11 knock-down in R4 neurons selected more concentrated, non-nutritive L-glucose even after 18 hours of starvation (FIG. 3c). This defect was as strong as the dSLC5A11 mutant phenotype, suggesting that dSLC5A11 functions in R4 neurons to promote this behavior. Consistent with this, we found that expression of UAS-dSLC5A11 only in R4 neurons of dSLC5A11 mutants completely rescued the behavioral defect (FIG. 3d).

Figure 11:
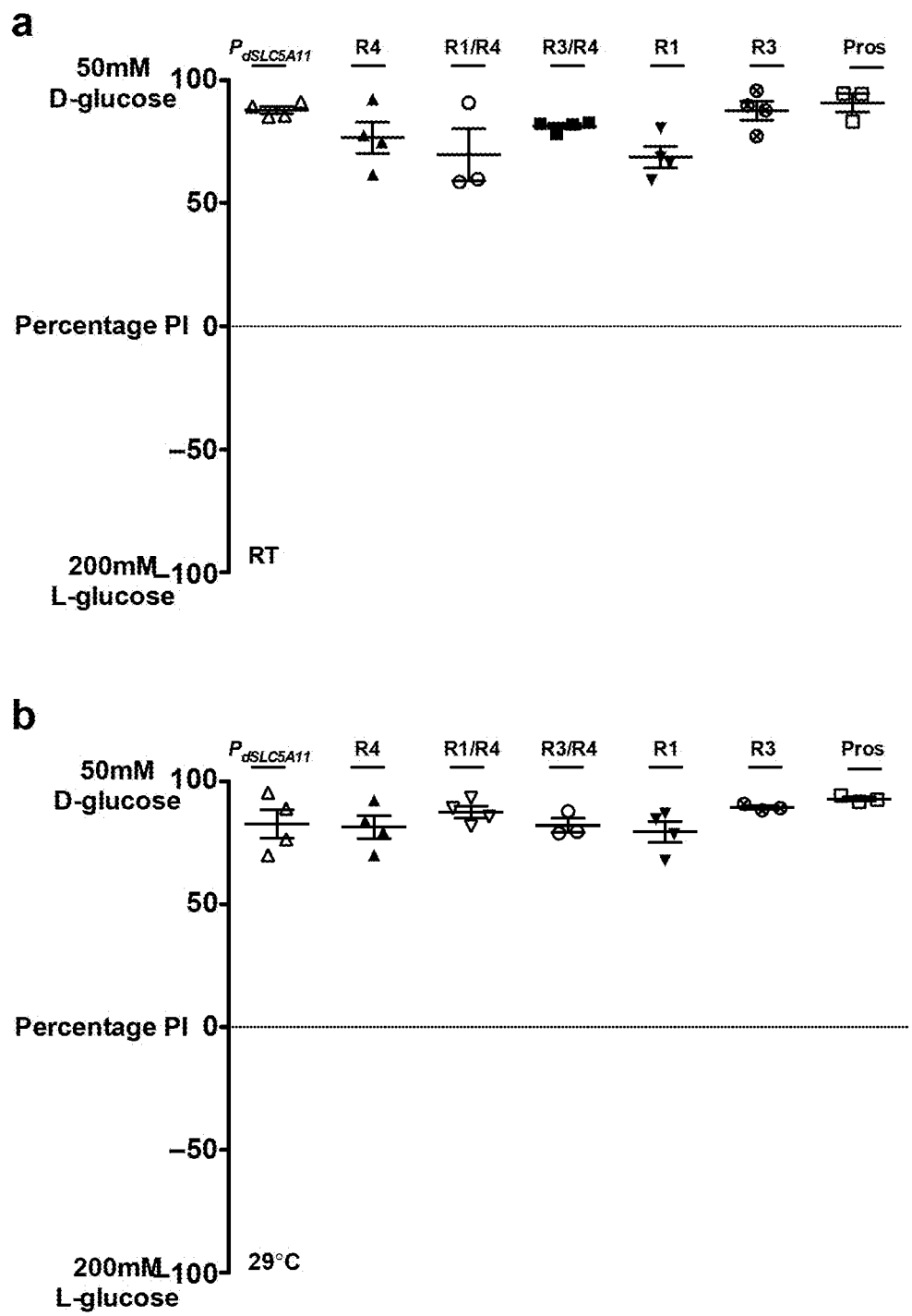
FIG. 11. Transgenic flies carrying GAL4 alone do not have defects in food choice behavior. The food choice behaviors of flies carrying GAL4 transgenes alone at RT (a) or 29° C. (b) were measured in the two-choice assay after 18 hours of starvation. n=3-4.
Figure 12:
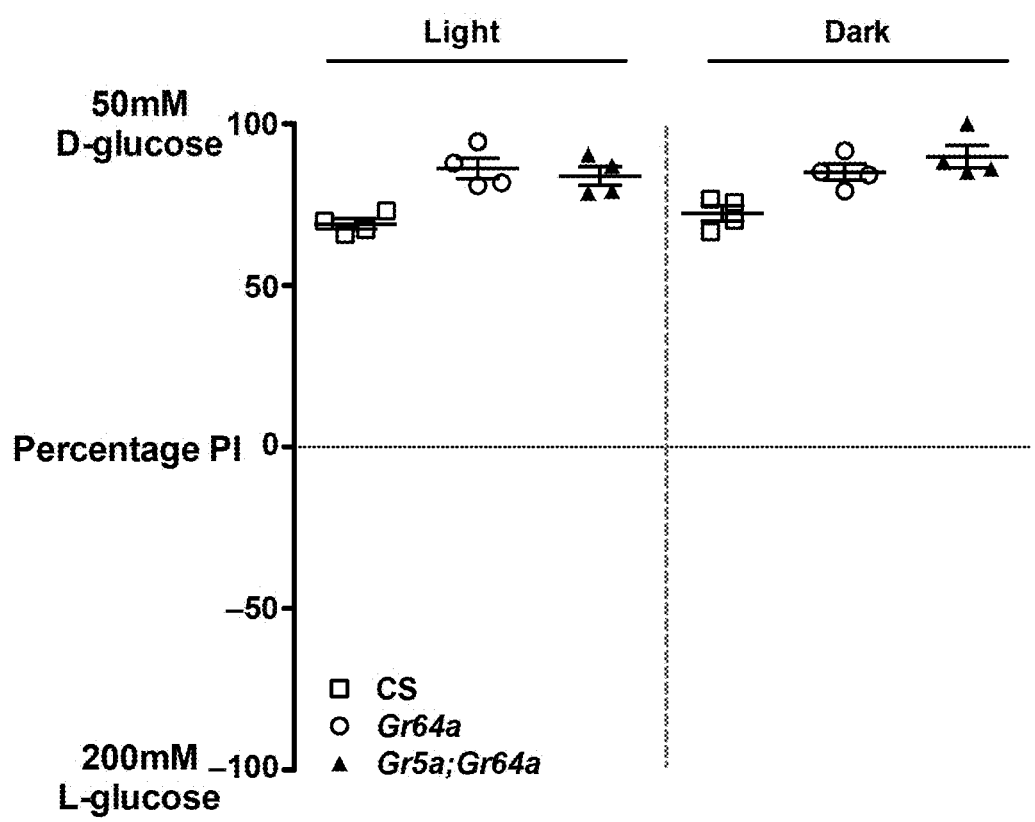
FIG. 12. Vision is not required for taste-independent food selection in WT or sugar-blind flies. The food choice behaviors of sugar-blind Gr5a;Gr64a, Gr64a, and CS flies in the light (left) and in the dark (right) were measured in the two-choice assay with 200 mM L-glucose versus 50 mM D-glucose after 18 hours of starvation. The sugar-blind flies had no defect in the selection of D-glucose in the absence of any visual cues. n=4. Two-way ANOVA with Bonferroni test indicates that there is no significant difference between flies tested in the dark and in the light for appropriate food selection.

To test whether the EB R4 neurons are required for taste-independent food preference, we used a variety of other R4-specific drivers that are not expressed in the antennae, the subesophageal ganglion or the anterior midgut in order to specifically inactivate R4 neurons and tested the flies in the two-choice assay. We found that conditional inactivation of this subset of EB R4 neurons by UAS-Kir2.1, $P_{tub}$-GAL80[ts] under the control of three different R4-GAL4 drivers abolished the selection of nutritive D-glucose, whereas silencing of the neighboring R1 and R3 neurons had no effect on this behavior (FIG. 3e and also FIG. 11). Notably, the R1 and R3 neurons are required for spatial memory, but R4 neurons are dispensable for this associative behavior. These findings suggest that visual place learning unlikely plays a role in the taste-independent food preference. Consistent with this, we found that foraging sugar-blind flies in the 2-choice arena were still able to choose D-glucose over L-glucose in the dark (FIG. 12).

The SLC5A11-expressing EB R4 neurons possibly act as a cellular substrate that detects the nutritional value of food through direct activation by nutritive sugar during the prandial rise in the hemolymph sugar levels. Alternatively, the function of EB R4 neurons may be to monitor the internal energy status of flies and stimulate feeding behavior upon starvation while the nutrient sensing is mediated by other neurons. In the mammalian brain, glucose excited or inhibited currents that are predominantly modulated by SGLTs might play a key role in the detection of nutrients, but their function is unclear due to the lack of functional analyses. Our studies using the genetically amenable *Drosophila* model provide a foundation for understanding interoceptive nutrient sensing in humans.

Example 2

Cloning and Generation of Transgenic Flies Expressing Different Human SGLT Genes The coding sequence (cDNA) of each of the three Sodium Glucose Transporter genes, SGLT1, SGLT2, and SGLT3, can be obtained from Open biosystems and cloned into a *Drosophila* expression vector, pUAST using standard molecular cloning techniques. Each pUAST vector containing the CDNA sequence of SGLT1, SGLT2, and SGLT3, pUAST(SGLT1), pUAST(SGLT2), and pUAST(SGLT3) can be used for injection into *Drosophila* embryos, specifically into the posterior germline cells to create a transgenic fly. Generation of such transgenic flies can be carried out through commercial entities—such as BestGene Inc. The process takes about 6 weeks and results in the production of transgenic flies with the pUAST vector inserted into different genomic locations (or into a selected genomic location by homologous recombination).

Functional Assay to Determine the Human Functional Homologue of SLC5A11/Cupcake pUAST(SGLT1), pUAST(SGLT2), and pUAST(SGLT3) flies can be crossed into flies mutant for the SLC5A11 (also known as cupcake) gene and also carrying the $P_{SLC5A11}$-GAL4 transgene which drives expression of the human CDNA only into the SLC5A11 expressing neurons (R4 cells of the ellipsoid body in the fly brain). Flies with genotypes: cupcake$^{-/-}$; $P_{SLC5A11}$-GAL4>pUAST(SGLT1) and cupcake$^{-/-}$; $P_{SLC5A11}$-GAL4>pUAST(SGLT2) and cupcake$^{-/-}$; $P_{SLC5A11}$-GAL4>pUAST(SGLT3) will be tested in the two-choice assay, a feeding assay developed by Dus et al. 2011, PNAS (108, 11644-11649), where sated or food-deprived flies are given a choice between 50 mM D-glucose (calorie, colored with green food dye) v. 200 mM L-glucose (no calorie, colored with red food dye) and their food choice scored by assessing the abdomen color after 2 h. cupcake$^{-/-}$ flies fail to choose the caloric sugars even when starved, while wild-type flies choose calorie. Because each of three experimental genotypes tested carry the cupcake mutant allele, they will show a phenotype (choose L-glucose when starved) unless one of the human SGLT genes can compensate for the fly gene function. Thus, if for example, cupcake$^{-/-}$; $P_{SLC5A11}$-GAL4>pUAST(SGLT3) flies have a normal feeding behavior, then it can be concluded that the hSGLT3 gene is the functional homologue of the *Drosophila* SLC5A11/cupcake gene. We will use cupcake$^{-/-}$; $P_{SLC5A11}$-GAL4>pUAST(cupcake) flies as a negative controls (where the cupcake mutation is rescued by overexpression of the cDNA for the cupcake gene) and cupcake$^{-/-}$ mutants as a positive control.

Screening of Compounds that Modulate the Action of the Human Cupcake Protein

To identify compounds that alter the function of the human homologue of the fly Cupcake protein (hCupcake), chemical compound libraries can be screened for effect on feeding behavior. Specifically, flies can be fed fly food mixed with each chemical compound for a few days, food-deprive the flies, and then test their food choice when given a choice between 50 mM D-glucose (calorie, colored with green food dye) v. 200 mM L-glucose (no calorie, colored with red food dye). Compounds that interfere with activity of the hCupcake protein will result in a phenotype (choosing L-glucose even when starved). Each compound having an effect on feeding can be tested for its direct activity on the hCupcake and dCupcake in ex vivo experiments using *Xenopus* oocytes. Human and fly cupcake can be cloned into pGEMHE, an expression vector optimized for amphibian expression, and injected into frog oocytes. For example, dCupcake expression results in a robust inward current in oocytes. Each chemical can be perfused into the saline solution and its effect on the human and fly Cupcake protein assessed.

The cDNA and deduced amino acid sequences are provided herein.

Example 3

Whole-cell patch-clamp recordings of neurons were carried out as follows. Then, *drosophila* brains were removed and then immediately immersed in ice-cold ACSF (220 mM sucrose, 2.5 mM KCl, 5.0 mM MgCl2, 1.0 mM CaCl2, 1.0 mM NaH2PO4, 26 mM NaHCO3, and 10 mM glucose), saturated with 95% 02 and 5% CO2. The brains were bathed in (126 mM NaCl, 26 mM NaHCO3, 2.8 mM KCl, 2.5 mM CaCl2, 1.25 mM NaH2PO4, 1.2 mM Mg504, and 5 mM or 2.5 mM glucose). The pipette solution for whole-cell recording was optionally modified to include an intracellular dye (Alexa Fluor 488): 120 mM K-gluconate, 10 mM KCl, 10 mM HEPES, 5 mM EGTA, 1 mM CaCl2, 1 mM MgCl2, and 2 mM MgATP, 0.03 mM Alexa Fluor 488 dye, pH 7.3. Electrophysiological signals were recorded using an Axopatch 700B amplifier (Molecular Devices), low-pass filtered at 2-5 kHz, and analyzed offline on a PC with pCLAMP programs (Molecular Devices). Recording electrodes had resistances of 4.0-6.0 MΩ when filled with K-gluconate pipette solution.

NachBac or TrpA1 were expressed by using the dSCL5A11 promoter. For example, we used dSCL5A11-GAL4 to drive expression of UAS-NachBac or TrpA1. UAS is a cognate promoter of GAL4.

Through a screen, we identified dSLC5A11 neurons that are required for behavioral responsiveness to nutritive D-glucose in the two-choice assay (D-glucose versus L-glucose). We previously proposed two mechanisms by which dSLC5A11 neurons may mediate the selection of nutritive sugars: (1) dSLC5A11 neurons could detect the nutritional value of sugar through direct activation; or (2) they may monitor the internal energy status of flies with the direct nutrient sensor located elsewhere. We proposed that the first mechanism—direct neuronal activation—occurs during the postprandial rise in hemolymph sugar levels. Through calcium imaging using a two-photon microscope and a more sensitive electrophysiological approach, we tested whether dSLC5A11 neurons can respond to solutions containing different nutritive sugars. These studies failed to demonstrate, however, that dSLC5A11 neurons are stimulated or inhibited by glucose or any other nutritive sugars (data not shown).

The alternative proposed mechanism suggests that dSLC5A11 neuronal activity is altered when the energy reservoir in the fly is depleted. To test this hypothesis, we conducted whole-cell patch-clamp recordings from dSLC5A11 neurons in wild-type (WT) flies carrying dSLC5A11-GAL4 and UAS-GFP that were sated or has been starved for 22 hours. While monitoring spontaneous activity of dSLC5A11 neurons in isolated brains, we observed that their neuronal excitability was altered following periods of starvation (FIG. 13A), with the frequency of spontaneous firing and bursting activity increasing considerably in starved animals (FIG. 18A).

Figure 13:
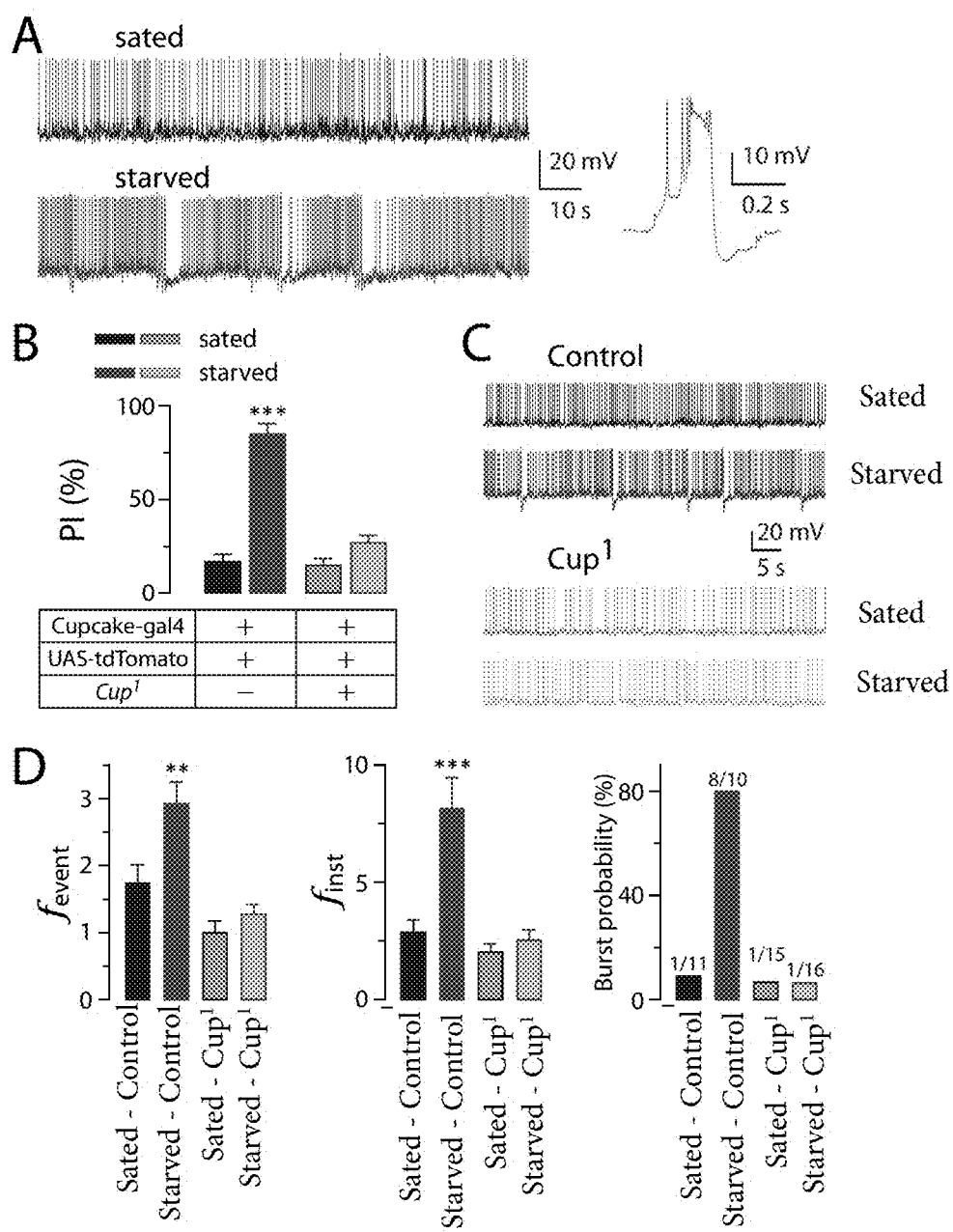
FIG. 13. Starvation enhances the excitability of dSLC5A11+, R4 neurons in the ellipsoid body of the *Drosophila* brain, which is dependent on dSLC5A11. (A) Representative traces of spontaneous activities recorded from the soma of dSLC5A11 neurons in isolated brain preparations obtained from either sated (blue, upper trace) or starved (red, lower trace) adult fly. (Right) Expanded plot of burst firing. (B) Behavior responses of 4-hr (sated) or 22-hr (starved) food deprived SLC5A11 mutant and control in the two-choice preference assay. Flies were given a choice between 50 mM D-glucose and 270 mM L-glucose (n=8-11). (C) Representative traces of spontaneous activities and (D) quantification of firing frequency and bursting probability of SLC5A11 neurons from the cohorts of flies in the same genetic background as those used in the behavioral assay in (B). $f_{event}$, event frequency. $f_{inst}$, instantaneous frequency. The numbers of bursting neurons out of the total number of recorded neurons are indicated above the bars. P<0.01, *P<0.001; error bars indicate SEM. Note that flies used in (A) have a different genetic background from the files used in (B), (C), and (D).

To determine the contribution of dSLC5A11 to neuronal excitability, we measured the activity of dSLC5A11 neurons in the isolated brains of dSLC5A11 mutants carrying dSLC5A11-GAL4 and UAS-tdTomato. We found that the excitability of dSLC5A11 neurons of WT flies carrying another marker, UAS-tdTomato, in a different genetic background was also significantly enhanced by starvation (FIG. 13C). This starvation-induced enhancement was essentially abolished in dSLC5A11 mutants, which failed to develop a preference for D-glucose over L-glucose (FIG. 13C). The frequency of spontaneous firing and burst activity in starved dSLC5A11 homozygotes was similar to that in sated WT flies (FIG. 13D). The similarity in the neuronal activity of starved dSLC5A11 mutant and sated WT flies is consistent with the similarity in their food preferences in the two-choice assay (FIG. 13B).

We also administered somatic step-current injections into dSLC5A11 neurons from a holding potential of −60 mV to examine its effects on the firing rate in starved versus sated flies. An increase in the magnitude of the current injection generated a greater firing rate, and more frequent bursts of action potentials. Consistent with the increase in spontaneous activity in starved animals, action potentials developed and burst activity occurred in a higher rate in dSLC5A11 neurons in starved animals compared to sated animals (FIG. 18B-D). This observation further supports the hypothesis that the threshold to drive action potentials is decreased in the dSLC5A11 neurons of starved animals.

Figure 14:
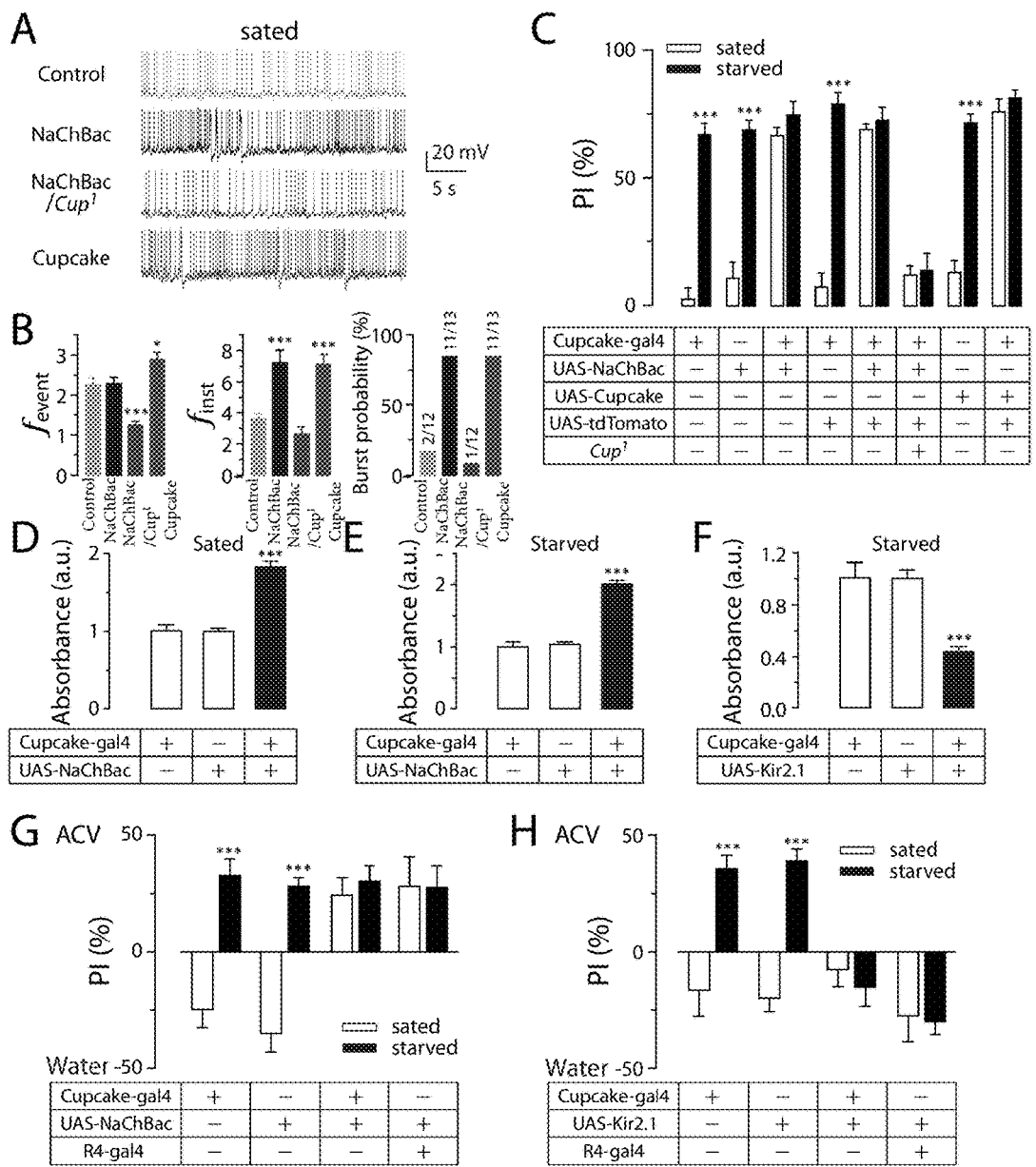
FIG. 14. The activity of dSLC5A11 neurons is both necessary and sufficient for hunger-driven behaviors. (A) Representative traces of spontaneous activities recorded from dSLC5A11 neurons from the brains of sated flies. Flies harboring dSLC5A11-GAL4 alone (control), gray; flies carrying dSLC5A11-GAL4 and UAS-NaChBac, blue; dSLC5A11 mutants bearing dSLC5A11-GAL4 and UAS-NaChBac, red; flies carrying dSLC5A11-GAL4 and UAS-dSLC5A11, purple. (B) Quantification of firing frequency and bursting probability in dSLC5A11 neurons from sated flies. $f_{event}$, event frequency. $f_{inst}$, instantaneous frequency. The numbers of bursting neurons out of the total number of recorded neurons are indicated above the bars. (C) Behavior responses of 4-hr (sated) or 22-hr (starved) food deprived flies in the two-choice assay (n=8-12). (D-F) Relative amounts of food consumed by 4-hr (sated) or 22-hr (starved) food deprived flies carrying dSLC5A11-GAL4, and either UAS-NaChBac (D and E) or UAS-Kir2.1 (F) (n=9-17). Flies carrying either dSLC5A11-GAL4 or UAS-responder alone were used as controls. (G-H) Olfactory responses of 4-hr (sated) or 22-hr (starved) food deprived flies bearing dSLC5A11-GAL4 and either UAS-Kir2.1 (G) or UAS-NaChBac (H) in a T-maze preference assay (n=7-15). Flies carrying either dSLC5A11-GAL4 or UAS-responder alone were used as controls. *P<0.05, P<0.01, *P<0.001; error bars indicate SEM.

Having shown that dSLC5A11 neuronal excitability is enhanced upon starvation, we sought to determine whether manipulating dSLC5A11 neuronal activity alters feeding behaviors. We artificially activated dSLC5A11 neurons by expressing the bacterial sodium channel, NachBac, in these neurons. As a result, neuronal activity increased dramatically, as indicated by the change in the rate of firing frequency and burst activity demonstrated by the whole-cell recordings (FIG. 14A-B). In contrast, NachBac-induced neuronal excitability was blunted in dSLC5A11 mutant flies. Overexpression of dSLC5A11 cDNA also enhanced neuronal excitability (FIG. 14A-B). These findings suggest that the function of dSLC5A1 is to stimulate the spontaneous activity of the neurons in which it is expressed.

The flies with activated dSLC5A11 neurons were evaluated using a number of feeding-related assays. In the two-choice assay, these flies strongly preferred the nutritive D-glucose even when they were sated, whereas control flies demonstrated no preference for either D- or L-glucose (FIG. 14C). We confirmed this finding through acutely activating dSLC5A11 neurons followed by observing the flies' behavior. Flies carrying dSLC5A11-GAL4 and UAS-TrpA1 at 32° C. developed a strong preference for nutritive D-glucose, even when they were sated (FIG. 19). Consistent with the artificial activation of dSLC5A11 neurons, overexpression of dSLC5A11 in these cells led sated flies to select the nutritive D-glucose over the sweeter, yet nonnutritive L-glucose (FIG. 14C). These results suggest that activation of these neurons is sufficient to mediate the selection of a nutritive sugar. However, this would argue against the possibility that dSLC5A11 neurons function as a nutrient sensor that directly monitors glucose levels in the hemolymph. The activation of such a nutrient sensor would cause the flies to perceive both D-glucose and L-glucose nutritious and display an equal preference for these sugars. Flies with activated dSLC5A11 neurons chose the nutritive sugar, however, because an increase in dSLC5A11 neuronal activity causes them to feel hungry and seek nutrient-rich foods.

We investigated the possibility that flies in which dSLC5A11 neurons were activated artificially would behave as if they were hungry, demonstrating alterations in their food intake. Indeed, artificial stimulation of dSLC5A11 neurons resulted in both sated and starved flies consuming twice as much food as control flies (FIG. 14D-E). Conversely, inactivation of dSLC5A11 neurons resulted in a significant decrease in food intake by starved flies (FIG. 14F). While the activity of dSLC5A11 neurons has a significant effect on food intake, the energy balance as measured by the total carbohydrate and fat contents in these flies is indistinguishable between these flies and controls (Dus et al., 2013). This observation suggests that the altered food intake is probably not caused by energy deficits, but rather by an altered sensation of hunger.

To investigate this prospect further, we studied dSLC5A11 neuronal activity in terms of the possibility that it is important for mediating the hunger-driven olfactory attraction to food odor. It is known that flies are attracted to food odor when they are starved in a four-field arena. In a binary choice assay using a T-maze, flies also preferred a side containing food odor or apple cider vinegar (ACV) when they were starved but avoided the same odor when they were sated (FIGS. 14G-H and Data not shown). This assay was used to measure the state of hunger or satiety in these flies. Flies with inactivated dSLC5A11 neurons displayed avoidance responses to a tube containing ACV, even after being starved for prolonged periods of time (FIG. 14G). This suggests that these flies were behaving as if they were satiated. Similarly, dSLC5A11 mutants were repelled by ACV even when they were starved (FIG. 20A). These results are consistent with the view that inactivation of dSLC5A11 neurons reduces the sensation of hunger and thus, caused flies to reduce their food intake and preference for nutritive sugars.

Conversely, flies with activated dSLC5A11 neurons were attracted to a tube containing ACV in a T-maze even when they were sated (FIG. 14H). This supports the expectation that such flies would behave as if they were starved. We also serendipitously observed that this manipulation results in a dramatic increase in the rate of proboscis response reflex (PER) responses, even in the absence of food (FIG. 20B). This natural feeding pattern is characterized by the repeated extension and retraction of the proboscis, which is evoked by contact with food. Starved flies often exhibit an increase in PER responses without appetitive stimuli. These results, together with the consumption of larger meals and the selection of nutritive sugars over nonnutritive sugars support the view that the activation of dSLC5A11 neurons enhances the sensation of hunger.

Figure 15:
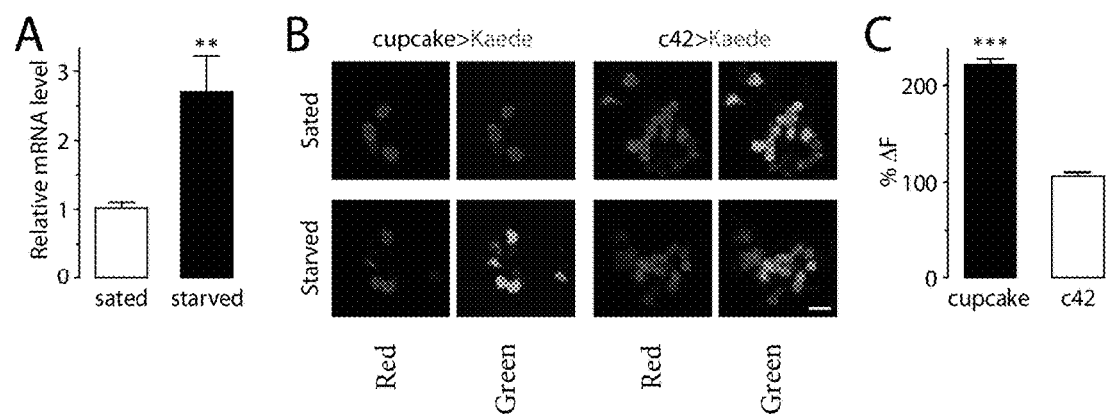
FIG. 15. Starvation increases the expression of dSLC5A11 transcript. (A) Quantitative real-time PCR assay for the dSLC5A11 transcript using the SYBR green method from the brains of sated (open bar) and starved (filled bar) flies. The transcript levels in starved flies were normalized to those in sated flies. GAPDH was used as a reference (n=7). (B) Monitoring de novo transcriptional activities of dSLC5A11 promoter in dSLC5A11 neurons. Flies carrying dSLC5A11-GAL4 and UAS-Kaede were photoactivated in order to convert preexisting KAEDE's green fluorescence to red, and were then reared in either sated or starved conditions prior to fluorescence imaging of the dissected brains. Note that c42-Gal4 labeled neurons comprise a subset of R2 and R4 neurons. (C) Relative amount of KAEDE synthesis within flies was calculated by normalizing to the preexisting red KAEDE (ΔF). To evaluate starvation-dependent KAEDE synthesis in dSLC5A11- or c42-Gal4 labeled neurons, the values from starved condition were normalized to those from sated condition (%ΔF; n=26-42). P<0.01, *P<0.001; error bars indicate SEM.
Figure 16:
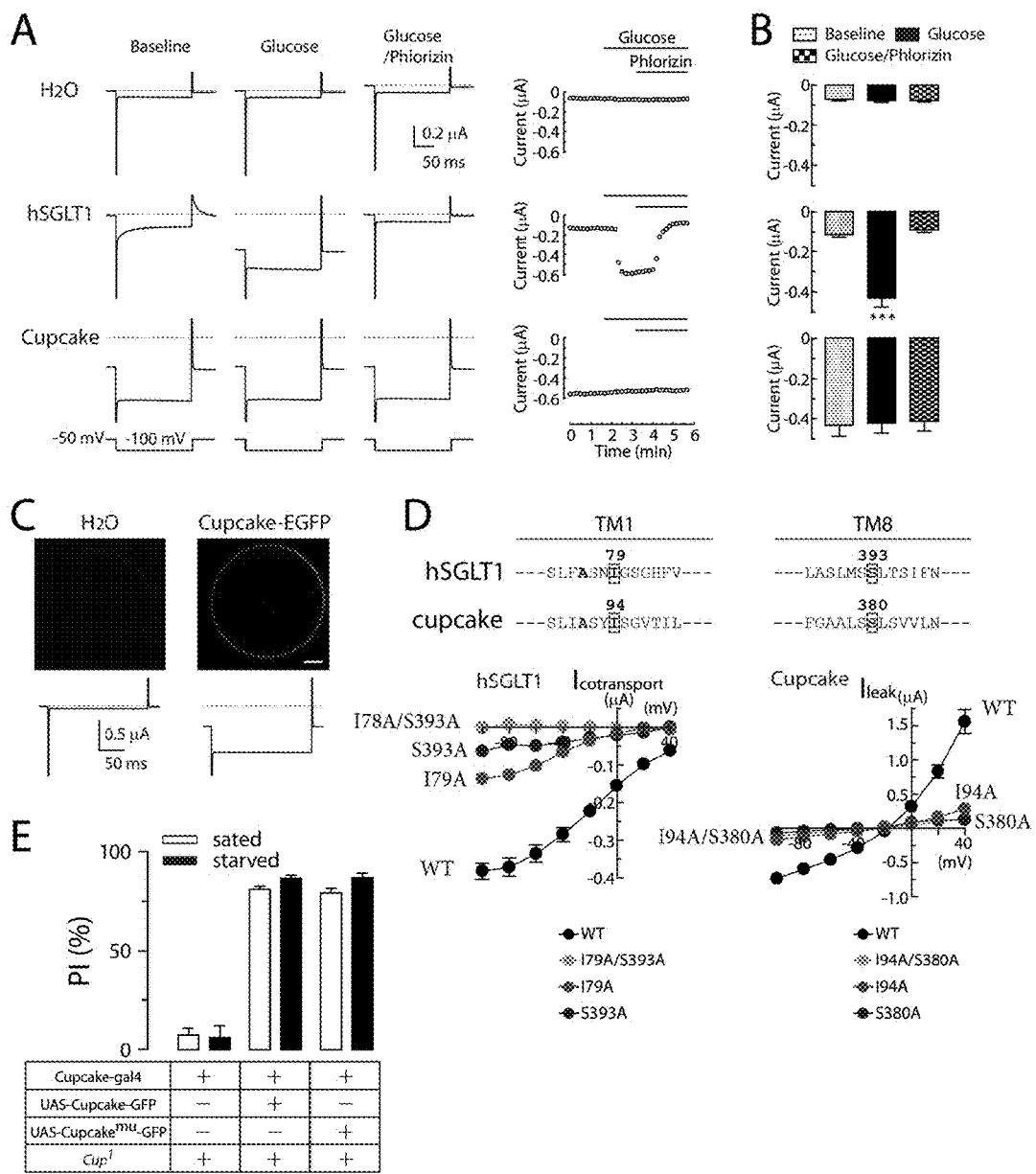
FIG. 16. The function of dSLC5A11 as a cotransporter or leak channel is not important for mediating hunger-driven behaviors. (A) Representative current traces in response to −100 mV test pulse from a holding potential of −50 mV in oocytes injected with $H_2O$, hSGLT1, or dSLC5A11 cRNA. Only hSGLT1 expressing oocytes showed glucose-dependent cotransport currents, which were blocked by the application of Phlorizin, an antagonist of SGLT. Representative traces as the function of time are shown (right). (B) Quantification of current amplitudes recorded during different applications from oocytes injected with $H_2O$, hSGLT1, or dSLC5A11 cRNA (n=9-11). (C) (Upper) Confocal images of oocytes injected with $H_2O$ or EGFP-tagged dSLC5A11 cRNA. (Lower) Current traces recorded from the corresponding oocytes. (D) (Upper) Sequence alignment of hSGLT1 and dSLC5A11 showed conserved sodium-binding sites. (Lower) Current-voltage analysis of oocytes injected with wild type or sodium-binding site mutant: hSGLT1 (left) or dSLC5A11 (right) (n=9-26). (E) Behavior responses of 4-hr (sated) or 22-hr (starved) food deprived dSLC5A11 mutants carrying dSLC5A11-GAL4 and either UAS-cupcake or UAS-cupcake$^{mu}$ in the two-choice assay. dSLC5A11 mutants carrying dSLC5A11-GAL4 alone were used as a control. ***P<0.001; error bars indicate SEM.

Having demonstrated that dSLC5A11 neuronal activity is sufficient to mediate hunger-driven behaviors, we next sought to understand how the dSLC5A11 molecule regulates dSLC5A11-expressing R4 neuronal excitability. dSLC5A11 neuronal excitability is enhanced by the overexpression of dSLC5A11 and is diminished by the dSLC5A11 mutations (FIG. 14A). Real-time polymerase chain reaction (RT-PCR) analysis illustrated that the expression of dSLC5A11 transcripts in the brain is upregulated when flies are starved (FIG. 15A). To determine whether the induction of dSLC5A11 transcripts actually occurs within dSLC5A11-expressing cells, we investigated dSLC5A11 promoter activity in sated versus starved animals. This involved the expression of a photoconvertible fluorescent protein, Kaede, in dSLC5A11 neurons, photoconverting the green fluorescence of Kaede to red, then monitoring the appearance of Kaede's native green fluorescence under the control of the dSLC5A11 promoter. Consistent with our findings in the RT-PCR experiment, the expression of green Kaede by the dSLC5A11 promoter in this experiment was enhanced when flies were maintained in a vial without food compared with flies that were allowed to feed ad libitum (FIG. 15B-C). These results indicate that the dSLC5A11 promoter stimulates the expression of dSLC5A11 transcripts when the internal energy reservoir of the fly is being depleted.

dSLC5A11 encodes a transmembrane protein that is homologous to the sodium/glucose cotransporter. To reconstitute the proposed function of dSLC5A11 in a heterologous system, we expressed dSLC5A11 in *Xenopus* oocytes and measured glucose-dependent cotransport currents using the two-electrode voltage-clamp technique. As a control, we measured the cotransport currents in oocytes expressing human sodium/glucose cotransporter 1 (hSGLT1), which were rapidly abolished by the presence of phlorizin, a SGLT inhibitor (FIG. 16A). However, oocytes injected with dSLC5A11 cRNA did not show any recognizable glucose-dependent cotransport currents (FIG. 16A-B). Nor did we observe co-transport current when other sugars were used to stimulate (FIG. 21A). The abundant amount of dSLC5A11 proteins had been translated and localized properly in the plasma membrane of the oocytes (FIG. 16C); this ruled out the possibility that the dSLC5A11 protein was misfolded or mislocalized. While carrying out the sequence alignment, we unexpectedly found that the putative sugar-binding site of other sodium/glucose cotransporters is not present in dSLC5A11 across all species (FIG. 21B). This finding, however, is consistent with the findings in the functional reconstitution experiment.

A notable feature of dSLC5A11-expressing oocytes is leak current (FIGS. 16A-B and 22A). This leak current could have been caused by damage to the oocytes, which may have occurred when electrodes impaled the oocytes. We investigated this possibility by testing ion selectivity of dSLC5A11-expressing oocytes and found that the replacement of sodium ions with larger impermeant choline ions reduced the amplitudes of leak currents and caused a negative shift in the reversal potential (FIG. 22B). This suggests that the leak current is mediated by sodium cations. To substantiate this, we introduced mutations at the conserved sodium-binding site between dSLC5A11 and other sodium/glucose cotransporters, and found that these mutations abolished the leak current (FIG. 16D). dSLC5A11 likely mediates nonselective cation currents, given that it is permeable to potassium, lithium, and cesium, but not to chloride and protons (FIG. 22C).

Despite this prominent characteristic, the leak current produced by dSLC5A11 is not important for feeding behavior. The expression of dSLC5A11 cDNA transgene containing the sodium-binding site mutation, UAS-cupcake (dSLC5A11)$^{mu}$-GFP, in dSLC5A11 neurons completely rescued the behavior defects of dSLC5A11 mutant (FIG. 16E). In addition to rescuing the mutant phenotype, we observed that expression of the dSLC5A11 mutant cDNA in dSLC5A11 neurons has dominant effects similar to those of WT dSLC5A11 cDNA (FIG. 16E and FIG. 23A). Flies in which either UAS-cupcake$^{mu}$-GFP or UAS-cupcake-GFP is expressed in their dSLC5A11 neurons exhibited a strong preference to the nutritive D-glucose even when they were sated. This strong preference was still observed in dSLC5A11 mutants (FIG. 16E), likely because the dSLC5A11 transcript is overexpressed through the GAL4/UAS system, which amplifies the rate of transcription. The whole-cell recordings showed that dSLC5A11 neurons expressing the mutant dSLC5A11 cDNA indeed potentiated membrane excitability, as robust as dSLC5A11 neurons expressing the WT dSLC5A11 cDNA (FIG. 23B). The electrophysiological characteristics of dSLC5A11 neurons in flies expressing the mutant dSLC5A11 are consistent with their behavior responses in the two-choice assay (FIGS. 16E and 23A-B). The morphology of dSLC5A11 neurons and their processes in flies carrying dSLC5A11-GAL4 and UAS-cupcake$^{mu}$-GFP appeared to be grossly indistinguishable from those of flies bearing dSLC5A11-GAL4 and UAS-cupcake-GFP (FIG. 23C).

To understand how an increase in dSLC5A11 enhances dSLC5A11 neuronal excitability, we investigated the possibility that dSLC5A11 modulates the K$^+$ current generated by the *Drosophila* KCNQ channel. The expression of dKCNQ in *Xenopus* oocytes resulted in the generation of large outward K$^+$ currents (FIG. 17A). Intriguingly, these currents were significantly inhibited by the co-expression of dSLC5A11 (FIG. 17A), whereas hSGLT1 potentiated the K$^+$ currents generated by KCNQ (FIG. 17B).

This unexpected finding suggests that dKNCQ regulates feeding behavior by regulating dSLC5A11 neuronal excitability. Indeed, KCNQ mutant flies strongly preferred the nutritive D-glucose to the nonnutritive L-glucose, even when they were sated (FIG. 17C). This may have been due to the dearth of K+ currents in this mutant, which would have resulted in greater dSLC5A11 neuronal excitability. To determine whether this effect is specific to dSLC5A11 neurons, we knocked down the endogenous dKNCQ transcript by expressing dKNCQ RNAi in dSLC5A11 neurons. We found that dKNCQ is required in these neurons to regulate appropriate nutrient selection (FIG. 17D).

Food deprivation results in the sensation of hunger—a compelling need or desire for food—which leads to a set of behaviors intended to address the nutrient deficiency. Our work shows that dSLC5A11 neurons are both necessary and sufficient for mediating the neural representation of hunger, which in turn leads to a series of behavioral changes involved in diminishing that hunger. Indeed, the activity of dSLC5A11 neurons increased when the animals were starved, and decreased when they were sated. The increase in dSLC5A11 neuronal activity was directly influenced by a starvation-induced increase in dSLC5A11 transcript levels, the translation of which likely resulted in an increase in dSLC5A11 protein levels. We demonstrate that the mechanism by the abundant levels of dSLC5A11 enhance dSLC5A11 neuronal activity involves the antagonism of K$^+$ currents induced by the dKNCQ channel.

The following sequences are provided herein:

```
SLC5A11 cDNA sequence (SEQ ID NO: 1):
ATGGAAGCGGTGGCAAAGAAGGGCATGGAGAACTACAGATTTGGCAGTGT

GGACTATGCCGTTTTCCTGGGCATGATCGTATTATCCACCAGCACGGGCA

TCTATTTCGGGTGCATCAAGAAGAGCAAGGTGAAGCTCGAGGAGGCGGAA

CCCACTCTGCCGACGACCACGCCAAAAAGGCGGAAACACGATTTCGGATC

GGAGAAGATGAGCGAGTATCTGCTAGGGTCACGCAATCTGAAAGTTTTCC

CCGTTGCCATGAGCCTGATAGCCAGCTATATATCGGGCGTTACCATACTG

GGCACAACCTCTGAGATCTACAATTATGGCACGCAATATTGGTTTATAGC

CATAGCAATAATGCTCCAAGGTATTGCCGTCTCCTACGTCTACATACCAG
```

-continued

```
TGTTCTCGGCTCTTCAAGTAGGCTCTTCCTATGAGTACTTGGAGATGCGC
TTTCATTCGGTCGTACGAAGTATTGCATCCTTTATGTTTATTCTGGATGA
GATTCTGTTTCTGCCTTTCATTGTGTATGTACCAGCTATAGCTCTGAATC
AGGTATCGGGCATTAATCTCCATGTGATTGCAGTGGTAATTGTGGTCGTG
TGTGTTTTCTACACCTTTGTCGGAGGAATCAAAGCAGTGGTCCACACAGA
TGCTTGGCAGGTGCTGGTCATGTTCCTTTCCGTTCTTGCTGTGGCTATTT
TGGCCACTGTCTATGCAAATGGCTTGAATGTCCTTTTCGATGATGCTGCC
AAAGGTGGCCGATTGATCTTTAACAATACAAACCCATCGCCTTATGTAAG
GCACACTGTTTGGAGCGTCCTAATCGGGGATTCTCCTACTGGACCTCAT
TCAATGCCGTCAACCAGACCATGGTCCAGCGATACATGTCTCTTCCATCG
CTCAAGAAGGCTCGTGCTTCCATGGCCATTTTTACAATTGGCGTGGCTGC
CTTCGTCTCTGTTTGTTGTTATGTGGGACTGCTAATCTATGAGATGTACA
AGATTGTGATCCTCTGAGTGCGGGACTAATAACACACGACGATCAGCTA
CTGCCGCTCTTTGTCGTTCAGAGTGTGGGTCATATCTATGGTATGTCTGG
TTTGTTTATAGCCGGCATATTTGGAGCTGCCTTGAGCTCCCTTTCTGTGG
TTCTGAACTCAACGTCCTTGGTAATCCTGGAGGATATAGTTCGCGGCTGC
TTCAAGATGCAACCAAGTGAAAGAGCCTCCACCATTCTGGTAAAGTCAAC
TGTTATAGTTCTTGGCTTTGTGGCCCTATCACTGGTATTTGTCCTGGAAC
AACTGAGTGGAATCCTGAGCATTTGCACTTCAATGACGGCCATCGCAGCT
GGAACCACTTTTGGCCTGTTTACCCTGGGAATGCTCGTTCCCTGGGCCAA
TACTGTAGGCACTGCTGTGGGCGGAATTGCAAGTGCTCTGCTCGCCGGGT
GGATATCCTTTGGAACGCAGTTTACCATCGCAGCGGGTGAATTGAATTCT
CAAAAGCTTCCCGTATCCGTGGAGGGATGTGTGGGCAATGTAACGCTTCG
GGAAAATATATGGGTAGATGAGGAGCAAGTTTTTCCACTGTACCGACTGT
CCTACCACTGGATAAATCCCATTGGTGTGGCCACAGTCATTGTGGTAGGT
GCACTAGTCTCCCTTGTGACCAAACCCACAAATATGAAAACACTAGATCC
GGATCTAATATCACCAGTGATTCACAGATTCCTTCCAAAAGAATGCTTTA
GTGGTCGCAATCTCCATGCGCAGGCGCACAAAAACCTCTTAAACGTATCC
TAA
```

SLC5A11 protein sequence (SEQ ID NO: 2):
MEAVAKKGMENYRFGSVDYAVFLGMIVLSTSTGIYFGCIKKSKVKLEEAE
PTLPTTTPKRRKHDFGSEKMSEYLLGSRNLKVFPVAMSLIASYISGVTIL
GTTSEIYNYGTQYWFIAIAIMLQGIAVSYVYIPVFSALQVGSSYEYLEMR
FHSVVRSIASFMFILDEILFLPFIVYVPAIALNQVSGINLHVIAVVIVVV
CVFYTFVGGIKAVVHTDAWQVLVMFLSVLAVAILATVYANGLNVLFDDAA
KGGRLIFNNTNPSPYVRHTVWSVLIGGFSYWTSFNAVNQTMVQRYMSLPS
LKKARASMAIFTIGVAAFVSVCCYVGLLIYEMYKDCDPLSAGLITHDDQL
LPLFVVQSVGHIYGMSGLFIAGIFGAALSSLVVLNSTSLVILEDIVRGC
FKMQPSERASTILVKSTVIVLGFVALSLVFVLEQLSGILSICTSMTAIAA
GTTFGLFTLGMLVPWANTVGTAVGGIASALLAGWISFGTQFTIAAGELNS
QKLPVSVEGCVGNVTLRENIWVDEEQVFPLYRLSYHWINPIGVATVIVVG
ALVSLVTKPTNMKTLDPDLISPVIHRFLPKECFSGRNLHAQAHKNLLNVS SLC5A11 gene region (SEQ ID NO: 3)
```
CATCAGTTGCAGTTCGGAAGCGGAATCGGTTGATGTTGTTGCTCCGATTC
GGACGTGGAATATTTCGCTTTTGTACACTCGTATTTTCGACTTCAAAGAA
TCGGGCAAAAGCGCACAGAACAGACCTGAAAAACTTTTCCGTGCGTTTCC
GAGTTTTGTTTTAATGTGTTCCATGTGATTAACTTTGTACGTTTATAGAA
CCCTTTTTTAAAAACCAATGGAAATACACGGAATCCGTTGACCCTTTTTG
CCACAAGAAAATTTTCATTACGTTTCGCAGAATTTGTTGGTAGTTTGCTC
TTTCTGGCCGTTTATCGTGCGTTGCTTTGCTGTTGATTTTCGTGAGGGAC
GCGCAATTTTCCATTCACCTCCGCTGCTCCAGTTACGGAAGCCACCCCCA
CCATTGTAAAGCCTAGCGTTTGCCGGTCCCCAACAATATGGAAGCGGTAC
GTATTTTGCACATTTCGCCGGTTCCAAACATTAAGAGCTATTTAGGAACT
TTGGAGCGGGGACACGGCATTTGGGTTACAAAGTCCAAGTCCAGGGCGA
TAATGCTGCTGCTCGAGATATTGCGTAAAAGGTTGAAGTCTCTTCTC
TGAGATTCGATCGGCTCCGATTGATCATCCAGTCAATGAACCTAAATGGC
AGACGAAAAATTAGTATTTTATGCTAAACACCGTCTGCATCATTAGATAG
GAACTAAGAAAGTAAAAGAAAATTGGGAGTATTAAAAATATATTAATTTT
GCTAATAACAAAAGATTCATAATCTAGAAAACCAAAGCTGGATAATGTCA
AAGTCACCAGAACGAGTTATCTTGCCAAATATGCATTTGATAATAACGCG
AAATCATATTAATAAAATGTTTTGTAATTTTGAAGCGATTGCTAAACATG
TTAAATAAATAATACATGGGGAAAAGGGTTAAAGTCTCTAGTCCGTAGAG
ATTGATGAATAATAAGCAGGCACCTGCTGATAAGACCTGGTTCCCATAAC
TTCACATGGACATGGACATTGTGGTTGTAGGGACTTAAGTACCACTTTTA
ATAATATGATTAAGCCATGGCATTTTGGACGAGCGAAACAAACTGTTTAA
AAGCAGATAAAAATGTATTGTGGAGTAATACATAAATAAACAAAGCGAGA
TAATTGTAATTAGCATGTATTTGCTAACTTTTTATACCTAGCTTTTAAGA
AAATCTCTTACCGTACACAGTTGGTACTTTAAAAGCAAGAGTCTCATTTT
CATTTTATGACCCATTTAAGACAAACTACAGCAATTACAAGTATATTGGC
CACAGACCCAGACGTGCGATGATTATATGAATTCTGAGTTCATTTCGCAC
ACTTGTTCTTACAAAAGAAACAAATTAAGTTTCTGAACTTTAAAACCACC
TGATAGAGATTGTCACTGCCAAGGAGAATCACAACAAACTTTAAACTAAA
TCATATAAAGATCATAAACTGACCCAAAATTAACTCTTTTTCTTAGGTGG
CAAAGAAGGGCATGGAGAACTACAGATTTGGCAGTGTGGACTATGCCGTT
TTCCTGGGCATGATCGTATTATCCACCAGCACGGGCATCTATTTCGGGTG
CATCAAGTGAGTGACCTTTAAACAAATCCTCGGAATATTGCCAAACAATT
GTTGTAATTACAGGAAGAGCAAGGTGAAGCTCGAGGAGGCGGAACCCACT
CTGCCGACGACCACGCCAAAAAGGCGGAAACACGATTTCGGATCGGAGAA
GATGAGCGAGTATCTGCTAGGGTCACGCAATCTGAAAGTTTTCCCCGTTG
CCATGAGCCTGATAGCCAGGTAGAGTTGGCGATGCGATCCCGCACCTCCA
AATATGCCTGTACAATCTGTTCCCTTTTATTTCCAGCTATATATCGGGCG
```

TTACCATACTGGGCACAACCTCTGAGATCTACAATTATGGCACGCAATAT
TGGTTTATAGCCATAGCAATAATGCTCCAAGGTATTGCCGTCTCCTACGT
CTACATACCAGTGTTCTCGGCTCTTCAAGTAGGCTCTTCCTATGAGGTAC
GATACTCGTAAATTCTATAAACTGATTTATACATTTACAATCTAATGGGT
CAATAAGCTTATGCTAACAGTAAAAGTAATAACGTCCAGAACGCAACCAA
AAATGTAAATTGGGTTTTAACGGAAATATTAATTTAGCTATAAAATACTC
ACCATTTCTTTCAATGACGAGTTAGTTAAAATAAAGATAGACAAGTTCAT
CTGTAGTGGTTGCTGATAAGAATGACAAACTTTCTAAGATGTTTCCGTCT
TCCCCCTTTCGCTCCGTCACTTTTGTCCAATCAATGAACGGAGGACGTAG
TGAACACTTTAATTAACTGGGAATCGGAGACCACCCTCCCCTCAAGTGGA
ATTTCTTGGACTTTGCACTCGCCCACTTGTTGCGACTTTTTCTGGGTTC
CAGCGGTTCGATATGATTAATTGCAATGTGGTTTTCTGCCACTTGACAAT
TGTGTCGAGCAATTAGTTTTCGTTTTCGGTCTTTATGACGTTAGTTTTCG
AATCCTAAACGCAAGTCATTTGAATTATGAAATATAATATTGCTTTCAGT
ACTTGGAGATGCGCTTTCATTCGGTCGTACGAAGTATTGCATCCTTTATG
TTTATTCTGGATGAGGTAAGTCAAAGATAATATTTGGACTGCAATGTTGT
AATAATTGTCGATCCAATTTTAGATTCTGTTTCTGCCTTTCATTGTGTAT
GTACCAGCTATAGCTCTGAATCAGGGTAAGCCGCATTTGTTAATTGTTTG
AAACACAACTTTAATCTTTCGATAATCTTGCAGTATCGGGCATTAATCTC
CATGTGATTGCAGTGGTAATTGTGGTCGTGTGTGTTTTCTACACCTTTGT
CGTAAGTTTTAGAGAGTTTCATACGTATGTTTTTATACTAATGGCGCCTA
TTTTCAGGGAGGAATCAAAGCAGTGGTCCACACAGATGCTTGGCAGGTGC
TGGTCATGTTCCTTTCCGTTCTTGCTGTGGCTATTTTGGCCACTGTCTAT
GCAAATGGCTTGAATGTCCTTTTCGATGATGCTGCCAAAGGTGGCCGATT
GATCTTTAACAATACAAACCCATCGCCTTATGTAAGGCACACTGTTTGGA
GCGTCCTAATCGGGGGATTCTCCTACTGGACCTCATTCAATGCCGTCAAC
CAGACCATGGTCCAGCGATACATGTCTCTTCCATCGCTCAAGAAGGCTCG
TGCTTCCATGGCCATTTTTACAATTGGCGTGGCTGCCTTCGTCTCTGTTT
GTTGTTATGTGGGACTGCTAATCTATGAGATGTACAAAGATTGTGATCCT
CTGAGTGCGGGACTAATAACAGTGAGTAAATAATAAATTGTTTTTGAACT
TTACTTACGTTTATTTCCTTGCAGCACGACGATCAGCTACTGCCGCTCTT
TGTCGTTCAGAGTGTGGGTCATATCTATGGTATGTCTGGTTTGTTTATAG
CCGGCATATTTGGAGCTGCCTTGAGCTCCCTTTCTGTGGTTCTGAACTCA
ACGTCCTTGGTAATCCTGGAGGATATAGTTCGCGGCTGCTTCAAGATGCA
ACCAAGTGAAAGAGCCTCCACCATTCTGGTAAAGTCAACTGTTATAGTTC
TTGGCTTTGTGGCCCTATCACTGGTATTTGTCCTGGAACAACTGAGTGGA
ATCCTGAGCATTTGCACTTCAATGACGGCCATCGCAGCTGGAACCACTTT
TGGCCTGTTTACCCTGGGAATGCTCGTTCCCTGGGCCAATACTGTAGGCA
CTGCTGTGGGCGGAATTGCAAGTGCTCTGCTCGCCGGGTGGATATCCTTT
GGAACGCAGTTTACCATCGCAGCGGGTGAATTGAATTCTCAAAAGCTTCC

CGTATCCGTGGAGGGATGTGTGGGCAATGTAACGCTTCGGGAAAATATAT
GGGTAGATGAGGAGCAAGTTTTTCCACTGTACCGACTGTCCTACCACTGG
ATAAATCCCATTGGTGTGGCCACAGTCATTGTGGTAGGTGCACTAGTCTC
CCTTGTGACCAAACCCACAAATATGAAAACACTAGATCCGGATCTAATAT
CACCAGTGATTCACAGGTAATTTTTGTAACCACATGTTTAACCTCTGTTA
TTAAACCCATTTTTTCTTCTAGATTCCTTCCAAAAGAATGCTTTAGTGGT
CGCAATCTCCATGCGCAGGCGCACAAAAACCTCTTAAACGTATCCTAAAA
TAGACGAACCAGAACTTCCTGTGCCAAACTAATGGAATTGATGGCATTGA
ATTCCACACCCTGTTTTGTTAGCATAGTTTGTAGTTGTAGTTGCTTTGTG
GTAGTTACCTTATAGATAGCCTAGTCTAGTACAATGTGATCCAGATATTG
GAAGACATAAACCGAAGTACAGGAACCTATGAATCTGCATCTCAGAATAC
AGAGTGCACAATCATTAACGTTATATAGTAAATGTATTATAATATAGCTT
TATTTAATTGTTCTGTTTGTATCCGTTCTTTACTTTCCAGCCTTTGTTCA
AGCATTATTTTTTGGCATTTTCGATTTGTAGTCAGCAGACTGTGTCTCA
TTATGTATTCCGTTTGACTTTACAAGCATAATGTCTGTGATAAATTCAAT
AAATAGATCATACATACT

SLC5A11 extended gene region (SEQ ID NO: 4):
GATGGTGACACGGGGGAGAGATTCCGGGAGATCGTGAGGGACTTCTGGT
CAGTGGTGAGGGTGCATCAAAGACCTCTGGTCTTGGAGTCAGTGAAAGCA
GAAGTTGAGTTGGCATCTGGACCTGGGGTTGAGTAGTGTCTGGAGTTGGT
GGAGATACTCTCAGCTCCGGAGAAGCCTTCAAGCTGAGTAGCCTCTTGGG
ATGCAGTTGCTCCTTTGCTTTTATGGGCTGTGCCACCGTAGCATTACTGG
CTTGGCTGCTGCTACTACTTTGTACGGAAACGGAGGAGGCACCGCTGAGT
ATGTTATCCAAAAGGGATTCAGGCGAAGTAGAGCTACCTCCTCCAGCCAA
GCTGCTAGTGGGCTCACTGCCACTGTCCCTATCCTGCACACCGAGTTCGA
CATTGGATAGCCCTGTACCTGATGACCCTGCACCCTGGGCACTATTCGAC
AAACCCAAAGTCCTAGATCTTCGGATGGAGCTCTTTGGTGCCAAACCCGG
TAGCTTTGGCACTGAGGGTAGATGTATTTTCGAAGTCACTTCGCTCTTTG
GGGCAATAGTAAAGGTAAAAAGTTGTGGTGCTGATTTGCGACGCACTGCG
TCTGGTAAGGGAGCGGTCTGCAGATTATTCTGCGAAGTCTGTGCGTTTTT
TCGTAAGGAAATTTTGGCAGAACTCAACTTTATCTTAAGTTTCCCTAAGG
ATGCACTGGGTGGCACAGCTGGAGTAGGAGGTGGGCTCGGAACAACTATT
TCCACATCCCCTCGGATGCGTTCGTAATCCGTTAACTGGCCACTCTTGTT
TCCGTTACTCGTTTTTCGCTTGAAAGCGATTTTCGAGCGATTTTCCCTGC
TCATGCTTCCCGGTTATGCAATCCTGCAGCTCGGACTACGGATTCCAGGC
AATCTGGAGCACCACCGCGTGTTCCCGTTGCAATTGGGACTGAAACTGAG
ACTGGGTCTCGGACTTGGTTGCTGCCTAATCCAATTACATTCCTCATTGG
AAACCCACGGCGCACTGCGAGTGCGAATGGTGGCAAAAGTCTGACACTGA
CAATTGTGCAATTATCTGTTGTGGTTGCTCATTCTAAATAGTTCTTTCAT
GACAACCTGTCACTTGCTATTGATTGACTTTCTGATTTTCTGAATCCAGA
GAGTATTTCGTGGTATGATGGGTGGGAGAAGATCCAACGGAGTAACCAAA

```
GGAACGTCTCAACTTCCGAGTACCCCGCTAAACCCGTGAAGTGAAACTCT
AGATGGACCCGATGTCGGTAGTGAATCAATTATTTTTTCATTTACCACCA
AAAGGGAGTGTTCAAATTACTTCTATTTTTAAATGTGGCAATGGTAAACT
TAGGTGTGTAGTTTACTACACGTTACTTGAGCAATTGATAGTGAATATAT
AATAATTTCAATATTACAGAAAACCCATAATGTCATATTAATACTAATAA
CCTTTTAACATATGTGTTTTTAAAATTGTTCGAATAATAGCGGATAACAA
CAGTTGAGTATTTTTTCATCTGAATGCAACTAGCTGCTCCAAACTTCCGT
TAATAGCTCCATTAGCTGATCGAATGGCCAAGTAACCACTTACATTGACA
TAATACATTGTGAGGATTACAAAAGCAACGAAGCTTTCTCTCCCACCTAA
TCTTGCCAAAGCCCCCACACATTTACAACACTCGCTCTTTTACTCTCTCT
ATACGCAATGGCAAGATAAATGGTTGGGAGAGGGAGCTTTTCGAGCGCAG
TATTAAGGGGTATATTATGTTCATGTTACAAATAATACTTTTATCCAGAA
AATATCAGTTGTATTCCCAATACTTGAGTCATTTATACATTTAGTTTTAT
TTATACATTTTATTTTTATTCTGTTCCGTTGTTCCTATGTTAAATATGAG
GTAATGGGTATACTTTGATCGGTACTCTCCATTCTAGCTGTCCCACTTGT
TTTTGTCGAGCAGCTGGCCTAGTGGCTTTTATTTTCGACCCGCTCGCAGA
CATCAGTTGCAGTTCGGAAGCGGAATCGGTTGATGTTGTTGCTCCGATTC
GGACGTGGAATATTTCGCTTTTGTACACTCGTATTTTCGACTTCAAAGAA
TCGGCAAAAGCGCACAGAACAGACCTGAAAAACTTTTCCGTGCGTTTCC
GAGTTTTGTTTTAATGTGTTCCATGTGATTAACTTTGTACGTTTATAGAA
CCCTTTTTTAAAAACCAATGGAAATACACGGAATCCGTTGACCCTTTTG
CCACAAGAAAATTTTCATTACGTTTCGCAGAATTTGTTGGTAGTTTGCTC
TTTCTGGCCGTTTATCGTGCGTTGCTTTGCTGTTGATTTCGTGAGGGAC
GCGCAATTTTCCATTCACCTCCGCTGCTCCAGTTACGGAAGCCACCCCCA
CCATTGTAAAGCCTAGCGTTTGCCGGTCCCCAACAATATGGAAGCGGTAC
GTATTTTGCACATTTCGCCGGTTCCAAACATTAAGAGCTATTTAGGAACT
TTGGAGCGGGGACACGGCATTTGGGTTACAAAGTCCAAGTCCAGGGCGA
TAATGCTGCTGCTGCTCGAGATATTGCGTAAAAGGTTGAAGTCTCTTCTC
TGAGATTCGATCGGCTCCGATTGATCATCCAGTCAATGAACCTAAATGGC
AGACGAAAAATTAGTATTTTATGCTAAACACCGTCTGCATCATTAGATAG
GAACTAAGAAAGTAAAAGAAAATTGGGAGTATTAAAAATATATTAATTTT
GCTAATAACAAAAGATTCATAATCTAGAAAACCAAAGCTGGATAATGTCA
AAGTCACCAGAACGAGTTATCTTGCCAAATATGCATTTGATAATAACGCG
AAATCATATTAATAAAATGTTTTGTAATTTTGAAGCGATTGCTAAACATG
TTAAATAAATAATACATGGGGAAAAGGGTTAAAGTCTCTAGTCCGTAGAG
ATTGATGAATAATAAGCAGGCACCTGCTGATAAGACCTGGTTCCCATAAC
TTCACATGGACATGGACATTGTGGTTGTAGGGACTTAAGTACCACTTTTA
ATAATATGATTAAGCCATGGCATTTTGGACGAGCGAAACAAACTGTTTAA
AAGCAGATAAAAATGTATTGTGGAGTAATACATAAATAAACAAAGCGAGA
TAATTGTAATTAGCATGTATTTGCTAACTTTTTATACCTAGCTTTTAAGA
AAATCTCTTACCGTACACAGTTGGTACTTTAAAAGCAAGAGTCTCATTTT
CATTTTATGACCCATTTAAGACAAACTACAGCAATTACAAGTATATTGGC
CACAGACCCAGACGTGCGATGATTATATGAATTCTGAGTTCATTTCGCAC
ACTTGTTCTTACAAAAGAAACAAATTAAGTTTCTGAACTTTAAAACCACC
TGATAGAGATTGTCACTGCCAAGGAGAATCACAACAAACTTTAAACTAAA
TCATATAAAGATCATAAACTGACCCAAAATTAACTCTTTTTCTTAGGTGG
CAAAGAAGGGCATGGAGAACTACAGATTTGGCAGTGTGGACTATGCCGTT
TTCCTGGGCATGATCGTATTATCCACCAGCACGGGCATCTATTTCGGGTG
CATCAAGTGAGTGACCTTTAAACAAATCCTCGGAATATTGCCAAACAATT
GTTGTAATTACAGGAAGAGCAAGGTGAAGCTCGAGGAGGCGGAACCCACT
CTGCCGACGACCACGCCAAAAAGGCGGAAACACGATTTCGGATCGGAGAA
GATGAGCGAGTATCTGCTAGGGTCACGCAATCTGAAAGTTTTCCCCGTTG
CCATGAGCCTGATAGCCAGGTAGAGTTGGCGATGCGATCCCGCACCTCCA
AATATGCCTGTACAATCTGTTCCCTTTTATTTCCAGCTATATATCGGGCG
TTACCATACTGGGCACAACCTCTGAGATCTACAATTATGGCACGCAATAT
TGGTTTATAGCCATAGCAATAATGCTCCAAGGTATTGCCGTCTCCTACGT
CTACATACCAGTGTTCTCGGCTCTTCAAGTAGGCTCTTCCTATGAGGTAC
GATACTCGTAAATTCTATAAACTGATTTATACATTTACAATCTAATGGGT
CAATAAGCTTATGCTAACAGTAAAAGTAATAACGTCCAGAACGCAACCAA
AAATGTAAATTGGGTTTTAACGGAAATATTAATTTAGCTATAAAATACTC
ACCATTTCTTTCAATGACGAGTTAGTTAAAATAAAGATAGACAAGTTCAT
CTGTAGTGGTTGCTGATAAGAATGACAAACTTTCTAAGATGTTTCCGTCT
TCCCCCTTTCGCTCCGTCACTTTTGTCCAATCAATGAACGGAGGACGTAG
TGAACACTTTAATTAACTGGGAATCGGAGACCACCCTCCCCTCAAGTGGA
ATTTCTTGGACTTTGCACTCGCCCACTTGTTGCGACTTTTTCTGGGTTC
CAGCGGTTCGATATGATTAATTGCAATGTGGTTTTCTGCCACTTGACAAT
TGTGTCGAGCAATTAGTTTTCGTTTTCGGTCTTTATGACGTTAGTTTTCG
AATCCTAAACGCAAGTCATTTGAATTATGAAATATAATATTGCTTTCAGT
ACTTGGAGATGCGCTTTCATTCGGTCGTACGAAGTATTGCATCCTTTATG
TTTATTCTGGATGAGGTAAGTCAAAGATAATATTTGGACTGCAATGTTGT
AATAATTGTCGATCCAATTTTAGATTCTGTTTCTGCCTTTCATTGTGTAT
GTACCAGCTATAGCTCTGAATCAGGGTAAGCCGCATTTGTTAATTGTTTG
AAACACAACTTTAATCTTTCGATAATCTTGCAGTATCGGGCATTAATCTC
CATGTGATTGCAGTGGTAATTGTGGTCGTGTGTTTTCTACACCTTTGT
CGTAAGTTTTAGAGAGTTTCATACGTATGTTTTTATACTAATGGCGCCTA
TTTTCAGGGAGGAATCAAAGCAGTGGTCCACACAGATGCTTGGCAGGTGC
TGGTCATGTTCCTTTCCGTTCTTGCTGTGGCTATTTTGGCCACTGTCTAT
GCAAATGGCTTGAATGTCCTTTTCGATGATGCTGCCAAAGGTGGCCGATT
GATCTTTAACAATACAAACCCATCGCCTTATGTAAGGCACACTGTTTGGA
GCGTCCTAATCGGGGATTCTCCTACTGGACCTCATTCAATGCCGTCAAC
CAGACCATGGTCCAGCGATACATGTCTCTTCCATCGCTCAAGAAGGCTCG
```

```
TGCTTCCATGGCCATTTTTACAATTGGCGTGGCTGCCTTCGTCTCTGTTT
GTTGTTATGTGGGACTGCTAATCTATGAGATGTACAAAGATTGTGATCCT
CTGAGTGCGGGACTAATAACAGTGAGTAAATAATAAATTGTTTTTGAACT
TTACTTACGTTTATTTCCTTGCAGCACGACGATCAGCTACTGCCGCTCTT
TGTCGTTCAGAGTGTGGGTCATATCTATGGTATGTCTGGTTTGTTTATAG
CCGGCATATTTGGAGCTGCCTTGAGCTCCCTTTCTGTGGTTCTGAACTCA
ACGTCCTTGGTAATCCTGGAGGATATAGTTCGCGGCTGCTTCAAGATGCA
ACCAAGTGAAAGAGCCTCCACCATTCTGGTAAAGTCAACTGTTATAGTTC
TTGGCTTTGTGGCCCTATCACTGGTATTTGTCCTGGAACAACTGAGTGGA
ATCCTGAGCATTTGCACTTCAATGACGGCCATCGCAGCTGGAACCACTTT
TGGCCTGTTTACCCTGGGAATGCTCGTTCCCTGGGCCAATACTGTAGGCA
CTGCTGTGGGCGGAATTGCAAGTGCTCTGCTCGCCGGGTGGATATCCTTT
GGAACGCAGTTTACCATCGCAGCGGGTGAATTGAATTCTCAAAAGCTTCC
CGTATCCGTGGAGGGATGTGTGGGCAATGTAACGCTTCGGGAAAATATAT
GGGTAGATGAGGAGCAAGTTTTTCCACTGTACCGACTGTCCTACCACTGG
ATAAATCCCATTGGTGTGGCCACAGTCATTGTGGTAGGTGCACTAGTCTC
CCTTGTGACCAAACCCACAAATATGAAAACACTAGATCCGGATCTAATAT
CACCAGTGATTCACAGGTAATTTTTGTAACCACATGTTTAACCTCTGTTA
TTAAACCCATTTTTTCTTCTAGATTCCTTCCAAAAGAATGCTTTAGTGGT
CGCAATCTCCATGCGCAGGCGCACAAAAACCTCTTAAACGTATCCTAAAA
TAGACGAACCAGAACTTCCTGTGCCAAACTAATGGAATTGATGGCATTGA
ATTCCACACCCTGTTTTGTTAGCATAGTTTGTAGTTGTAGTTGCTTTGTG
GTAGTTACCTTATAGATAGCCTAGTCTAGTACAATGTGATCCAGATATTG
GAAGACATAAACCGAAGTACAGGAACCTATGAATCTGCATCTCAGAATAC
AGAGTGCACAATCATTAACGTTATATAGTAAATGTATTATAATATAGCTT
TATTTAATTGTTCTGTTTGTATCCGTTCTTTACTTTCCAGCCTTTGTTCA
AGCATTATTTTTTGGCATTTTCGATTTGTAGTCAGCAGACTGTGTCTCA
TTATGTATTCCGTTTGACTTTACAAGCATAATGTCTGTGATAAATTCAAT
AAATAGATCATACATACTATCCGAATTTTGTACACCTAGAATATAGTTAA
GCGGTTGCAAAGCAGCAGGAATGATATGACCTCTGTCTGGATCTGGATCT
GGGATCTGAGTCTGGAATCTGGCGTATCTAGTCTAAACTAAGCCCCAATC
AGGCGTAAATCACAAAAGAGGATATGCCTTGTATAGGCATGCTTATACAT
ACTAATTAACCTTCCGATGATCTACAGCCGACGACTGTCTTCTGCTTTGG
ATGCACTTTCGTAGCTGGAACCCGATGACAATTAGGCAAAGAATGCCAGC
ACTCAGATAGCTATTGAAGACAAACTGCTGTGGCAGCATTTTGCACTTGG
AAACCACATAGTCATCGGGGGTTATAGTGGCCTAAAAGTTATGGCATGTT
AGTACAAGTTCGAAGGGCTAACAATCGTAAGAGCAAATATAATACTCACC
AGCATAAAGCTGGGATTAACTTTGTTTCGCCAGCTGAATGAGGCCACCGT
GTACTCATCGATGCCCAGTCGATTTACACTGTGACAGAAGTGATGTGAAT
GACCGGCGAATGCCAGCCTTGGCTTAAGCAGCTCTCCCAGCATATCCGTG
GCATCCTTGGAGAGCACATGAAACCGCTCTCGGAACGCCTCGATGTACGG
AGCATCGTGCTCCTCGCACATGGTATCCGAAATGCGGTAGGTGGGAAAGT
GCTGCAATAGAATTGGCTGGCTGTACGGGTGCCGCCTGGTGCGAGCGCAC
TCCGCCTCTAGTGGATACTTCATGCAGTACAAAGTCCTCGAAATGTTTTT
CAACTGATCCTCGGCCTGGGTGCAAAACATGCAACCATCACCTTCCATAG
CCATCGAATTTATCACCACAAAATGGATTTGTTTAATGGTGTACAAATTG
ACCGAGGAGTTGTTCAGATAACTCTCAAAACGCGACATAAAGAAGGGATG
CATTCTGGAAAACACACAAGAGCGCGGTTTAACAAATATCAGGGAATACA
CATAGTCTCTTATTGACTTACTTGTAATGGAAGCCCACGTCATGATTTCC
CGCGACACTGATGAGCGGAATTCCCGGTGGTAGGTGGAACATCTTCAGGT
AGCGCCACACATATTCCTGGAACTGCTTGTCGCTGACCATGTCGCCCTCG
TCGAACAAATCGCCCAAGACGAAGACCACGTCGGGCTGGAACAGACGTGA
TGCCGCCTGAAAGGCCCGCGTCATGTGCCACTCCCGGTAGAGCTTGTCCA
GCCAGTGACCACGATGCGGTCCCAGCAGATGCGGATCCGCTAGAATCATT
GCCCTAAGCGGATCGTCCACATACTTCTTTCGCTTTATCTCCGGCCACTT
GCACTTTTGCAGCACCACAAAGTCCGCCACATATTCGCAGAAGATCAGGG
CGCACAGCACGATCACAAAGCAGGCATAAAGAAAGCGCATTTCAGGATTT
CTCACCGGCTAAAAAAATAATAACAAATTTATTCTAGAGCTGAAAAACCA
TCAGCGATAGTATCGTTTTAAACGAGTAAACGGCCCGATATAAATTTAAA
ATATTCGATAAATTAAACAGTGCTGTCAAGCGGCTGTCGGTTGACTAACA
AATTGGCGCCTCATTTCAAAGTTGGTTACTAAAATTGTAAATTGGAAAAA
TTATGAAGCATTATGGCTTATATATAATTTCCTTTATTTGGAATAGGTAT
TGTGCATTGCATGCTGCTTACAGGCTAACTAGAAGAGATCGTAAAAATAG
TTTAGGCCTTGGCCAAGTTCCCAGATTGAAATGCCAGTGCCCAGTTCCTG
GGCGAGCTTTATTCGCTCGTTTATGGAATAGAGAGTGGGATAAAAGACAA
TGTGGCGACCGTCATCGTTTCTGAAAGTAATGATATTCATCATCTTCGCC
TTACACTCTGCATACGCTGCAGTAGAAAACTCACTTGATTTCAAAGAAAT
TTTCCACATCCCGCTCATCGTAAGTTAGGTGCTTCTTCACATGCCTGACT
AGATCCAAGTACTGGGAG
```

While the present invention has been described through specific embodiments, various modifications will be apparent to those skilled in the art and such modifications are intended to be within the scope of this disclosure.

The invention claimed is:

1. A method for identifying a candidate agent that interferes with hunger sensation, comprising:
   (i) providing a *Drosophila melanogaster*, wherein said *D. melanogaster* exhibits a preference for metabolizing sugar when starved,
   (ii) feeding the *D. melanogaster* a candidate agent,
   (iii) starving the *D. melanogaster* for a period of time; and
   (iv) feeding the starved *D. melanogaster*, wherein said feeding comprises a choice between metabolizing sugar and non-metabolizing sugar and wherein a lack of preference for metabolizing sugar indicates a candidate agent that affects sodium/solute cotransporter-like protein SLC5A11 gene function and interferes with hunger sensation.

2. The method of claim 1, wherein the *D. melanogaster* are starved for at least 5 hours.

3. The method of claim 1, wherein the *D. melanogaster* are starved for 24 hours.

4. The method of claim 1, wherein the *D. melanogaster* in step i) comprises a gene encoding for the human sodium/solute cotransporter-like protein SLC5A11.

5. A method for identifying a candidate agent that interferes with hunger sensation, comprising:
   (i) providing *Drosophila melanogaster* neurons ex vivo that express a gene encoding for the sodium/solute cotransporter-like protein SLC5A11;
   (ii) activating the neurons in the presence of a candidate agent; and
   (iii) evaluating excitability of the neurons after exposure to the candidate agent, wherein a decrease in the excitability of the neurons indicates a candidate agent that affects the sodium/solute cotransporter-like protein SLC5A11 gene function and interferes with hunger sensation.

6. A method for identifying a candidate agent that interferes with hunger sensation, comprising:
(i) providing a *Drosophila melanogaster*;
(ii) feeding a candidate agent to the *D. melanogaster*;
(iii) starving the *D. melanogaster* for a period of time; and
(iv) evaluating excitability of neurons from the *D. melanogaster* that express a gene encoding for the sodium/solute cotransporter-like protein SLC5A11 protein, wherein a decrease in the excitability of the neurons indicates a candidate agent that interferes with sodium/solute cotransporter-like protein SLC5A11 gene function and interferes hunger sensation.

7. The method of claim 5, wherein the *D. melanogaster* in step i) comprises a gene encoding for the human sodium/solute cotransporter-like protein SLC5A11.

8. The method of claim 6, wherein the *D. melanogaster* in step i) comprises a gene encoding for the human sodium/solute cotransporter-like protein SLC5A11.

9. The method of claim 1, wherein the SLC5A11 gene in *D. melanogaster* in step i) has been replaced with a gene encoding for the human sodium/solute cotransporter-like protein SLC5A11.

10. The method of claim 5, wherein the SLC5A11 gene in *D. melanogaster* in step i) has been replaced with a gene encoding for the human sodium/solute cotransporter-like protein SLC5A11.

11. The method of claim 6, wherein the SLC5A11 gene in *D. melanogaster* in step i) has been replaced with a gene encoding for the human sodium/solute cotransporter-like protein SLC5A11.

* * * * *

SEQUENCE LISTING

<160> NUMBER OF SEQ ID NOS: 8

<210> SEQ ID NO 1

<211> LENGTH: 1803
<212> TYPE: DNA
<213> ORGANISM: Drosophila melanogaster

<400> SEQUENCE: 1

| | |
|---|---|
| atggaagcgg tggcaaagaa gggcatggag aactacagat ttggcagtgt ggactatgcc | 60 |
| gttttcctgg gcatgatcgt attatccacc agcacgggca tctatttcgg gtgcatcaag | 120 |
| aagagcaagg tgaagctcga ggaggcggaa cccactctgc cgacgaccac gccaaaaagg | 180 |
| cggaaacacg atttcggatc ggagaagatg agcgagtatc tgctagggtc acgcaatctg | 240 |
| aaagttttcc ccgttgccat gagcctgata gccagctata tcgggcgt taccatactg | 300 |
| ggcacaacct ctgagatcta caattatggc acgcaatatt ggtttatagc catagcaata | 360 |
| atgctccaag gtattgccgt ctcctacgtc tacataccag tgttctcggc tcttcaagta | 420 |
| ggctcttcct atgagtactt ggagatgcgc tttcattcgg tcgtacgaag tattgcatcc | 480 |
| tttatgttta ttctggatga gattctgttt ctgccttttca ttgtgtatgt accagctata | 540 |
| gctctgaatc aggtatcggg cattaatctc catgtgattg cagtggtaat gtggtcgtg | 600 |
| tgtgttttct acacctttgt cggaggaatc aaagcagtgg tccacacaga tgcttggcag | 660 |
| gtgctggtca tgttcctttc cgttcttgct gtggctattt tggccactgt ctatgcaaat | 720 |
| ggcttgaatg tccttttcga tgatgctgcc aaaggtggcc gattgatctt aacaataca | 780 |
| aacccatcgc cttatgtaag gcacactgtt tggagcgtcc taatcggggg attctcctac | 840 |
| tggacctcat tcaatgccgt caaccagacc atggtccagc gatacatgtc tcttccatcg | 900 |
| ctcaagaagg ctcgtgcttc catggccatt tttacaattg gcgtggctgc cttcgtctct | 960 |
| gtttgttgtt atgtgggact gctaatctat gagatgtaca agattgtga tcctctgagt | 1020 |
| gcgggactaa taacacacga cgatcagcta ctgccgctct tgtcgttca gagtgtgggt | 1080 |
| catatctatg gtatgtctgg tttgtttata gccggcatat ttggagctgc cttgagctcc | 1140 |
| cttttctgtg gttctgaactc aacgtccttg gtaatcctgg aggatatagt tcgcggctgc | 1200 |
| ttcaagatgc aaccaagtga agagcctcc accattctgg taaagtcaac tgttatagtt | 1260 |
| cttggctttg tggccctatc actggtattt gtcctggaac aactgagtgg aatcctgagc | 1320 |
| atttgcactt caatgacggc catcgcagct ggaaccactt ttggcctgtt taccctggga | 1380 |
| atgctcgttc cctgggccaa tactgtaggc actgctgtgg gcggaattgc aagtgctctg | 1440 |
| ctcgccgggt ggatatcctt tggaacgcag tttaccatcg cagcgggtga attgaattct | 1500 |
| caaaagcttc ccgtatccgt ggagggatgt gtgggcaatg taacgcttcg ggaaaatata | 1560 |
| tgggtagatg aggagcaagt ttttccactg taccgactgt cctaccactg gataaatccc | 1620 |
| attggtgtgg ccacagtcat tgtggtaggt gcactagtct cccttgtgac caaacccaca | 1680 |
| aatatgaaaa cactagatcc ggatctaata tcaccagtga ttcacagatt ccttccaaaa | 1740 |
| gaatgcttta gtggtcgcaa tctccatgcg caggcgcaca aaaacctctt aaacgtatcc | 1800 |
| taa | 1803 |

<210> SEQ ID NO 2
<211> LENGTH: 600
<212> TYPE: PRT
<213> ORGANISM: Drosophila melanogaster

<400> SEQUENCE: 2

Met Glu Ala Val Ala Lys Lys Gly Met Glu Asn Tyr Arg Phe Gly Ser
1               5                   10                  15

-continued

Val Asp Tyr Ala Val Phe Leu Gly Met Ile Val Leu Ser Ser Thr
            20                  25                  30

Gly Ile Tyr Phe Gly Cys Ile Lys Lys Ser Lys Val Lys Leu Glu Glu
            35                  40                  45

Ala Glu Pro Thr Leu Pro Thr Thr Pro Lys Arg Arg Lys His Asp
 50                  55                  60

Phe Gly Ser Glu Lys Met Ser Glu Tyr Leu Leu Gly Ser Arg Asn Leu
 65                  70                  75                  80

Lys Val Phe Pro Val Ala Met Ser Leu Ile Ala Ser Tyr Ile Ser Gly
                85                  90                  95

Val Thr Ile Leu Gly Thr Thr Ser Glu Ile Tyr Asn Tyr Gly Thr Gln
            100                 105                 110

Tyr Trp Phe Ile Ala Ile Ala Ile Met Leu Gln Gly Ile Ala Val Ser
            115                 120                 125

Tyr Val Tyr Ile Pro Val Phe Ser Ala Leu Gln Val Gly Ser Ser Tyr
            130                 135                 140

Glu Tyr Leu Glu Met Arg Phe His Ser Val Val Arg Ser Ile Ala Ser
145                 150                 155                 160

Phe Met Phe Ile Leu Asp Glu Ile Leu Phe Leu Pro Phe Ile Val Tyr
            165                 170                 175

Val Pro Ala Ile Ala Leu Asn Gln Val Ser Gly Ile Asn Leu His Val
            180                 185                 190

Ile Ala Val Val Ile Val Val Cys Val Phe Tyr Thr Phe Val Gly
            195                 200                 205

Gly Ile Lys Ala Val His Thr Asp Ala Trp Gln Val Leu Val Met
            210                 215                 220

Phe Leu Ser Val Leu Ala Val Ala Ile Leu Ala Thr Val Tyr Ala Asn
225                 230                 235                 240

Gly Leu Asn Val Leu Phe Asp Asp Ala Ala Lys Gly Gly Arg Leu Ile
            245                 250                 255

Phe Asn Asn Thr Asn Pro Ser Pro Tyr Val Arg His Thr Val Trp Ser
            260                 265                 270

Val Leu Ile Gly Gly Phe Ser Tyr Trp Thr Ser Phe Asn Ala Val Asn
            275                 280                 285

Gln Thr Met Val Gln Arg Tyr Met Ser Leu Pro Ser Leu Lys Lys Ala
            290                 295                 300

Arg Ala Ser Met Ala Ile Phe Thr Ile Gly Val Ala Ala Phe Val Ser
305                 310                 315                 320

Val Cys Cys Tyr Val Gly Leu Leu Ile Tyr Glu Met Tyr Lys Asp Cys
            325                 330                 335

Asp Pro Leu Ser Ala Gly Leu Ile Thr His Asp Asp Gln Leu Leu Pro
            340                 345                 350

Leu Phe Val Val Gln Ser Val Gly His Ile Tyr Gly Met Ser Gly Leu
            355                 360                 365

Phe Ile Ala Gly Ile Phe Gly Ala Ala Leu Ser Ser Leu Ser Val Val
            370                 375                 380

Leu Asn Ser Thr Ser Leu Val Ile Leu Glu Asp Ile Val Arg Gly Cys
385                 390                 395                 400

Phe Lys Met Gln Pro Ser Glu Arg Ala Ser Thr Ile Leu Val Lys Ser
            405                 410                 415

Thr Val Ile Val Leu Gly Phe Val Ala Leu Ser Leu Val Phe Val Leu
            420                 425                 430

Glu Gln Leu Ser Gly Ile Leu Ser Ile Cys Thr Ser Met Thr Ala Ile

```
                    435                 440                 445
Ala Ala Gly Thr Thr Phe Gly Leu Phe Thr Leu Gly Met Leu Val Pro
    450                 455                 460

Trp Ala Asn Thr Val Gly Thr Ala Val Gly Gly Ile Ala Ser Ala Leu
465                 470                 475                 480

Leu Ala Gly Trp Ile Ser Phe Gly Thr Gln Phe Thr Ile Ala Ala Gly
                485                 490                 495

Glu Leu Asn Ser Gln Lys Leu Pro Val Ser Val Glu Gly Cys Val Gly
                500                 505                 510

Asn Val Thr Leu Arg Glu Asn Ile Trp Val Asp Glu Gln Val Phe
    515                 520                 525

Pro Leu Tyr Arg Leu Ser Tyr His Trp Ile Asn Pro Ile Gly Val Ala
    530                 535                 540

Thr Val Ile Val Val Gly Ala Leu Val Ser Leu Val Thr Lys Pro Thr
545                 550                 555                 560

Asn Met Lys Thr Leu Asp Pro Asp Leu Ile Ser Pro Val Ile His Arg
                565                 570                 575

Phe Leu Pro Lys Glu Cys Phe Ser Gly Arg Asn Leu His Ala Gln Ala
                580                 585                 590

His Lys Asn Leu Leu Asn Val Ser
            595                 600

<210> SEQ ID NO 3
<211> LENGTH: 4668
<212> TYPE: DNA
<213> ORGANISM: Drosophila melanogaster

<400> SEQUENCE: 3
catcagttgc agttcggaag cggaatcggt tgatgttgtt gctccgattc ggacgtggaa    60
tatttcgctt ttgtacactc gtattttcga cttcaaagaa tcgggcaaaa gcgcacagaa   120
cagacctgaa aaacttttcc gtgcgtttcc gagttttgtt ttaatgtgtt ccatgtgatt   180
aactttgtac gtttatagaa cccttttta aaaaccaatg gaaatacacg gaatccgttg    240
accctttttg ccacaagaaa attttcatta cgtttcgcag aatttgttgg tagttttgctc  300
tttctggccg tttatcgtgc gttgctttgc tgttgatttt cgtgagggac gcgcaatttt   360
ccattcacct ccgctgctcc agttacggaa gccaccccca ccattgtaaa gcctagcgtt   420
tgccggtccc caacaatatg gaagcggtac gtattttgca catttcgccg gttccaaaca   480
ttaagagcta tttaggaact ttggagcggg ggacacggca tttgggttac aaagtccaag   540
tccagggcga taatgctgct gctgctcgag atattgcgta aaaggttgaa gtctcttctc   600
tgagattcga tcggctccga ttgatcatcc agtcaatgaa cctaaatggc agacgaaaaa   660
ttagtatttt atgctaaaca ccgtctgcat cattagatag gaactaagaa agtaaaagaa   720
aattgggagt attaaaaata tattaatttt gctaataaca aaagattcat aatctagaaa   780
accaaagctg gataatgtca aagtcaccag aacgagttat cttgccaaat atgcatttga   840
taataacgcg aaatcatatt aataaaatgt tttgtaattt tgaagcgatt gctaaacatg   900
ttaaataaat aatacatggg gaaaagggtt aaagtctcta gtccgtagag attgatgaat   960
aataagcagg cacctgctga taagacctgg ttcccataac ttcacatgga catggacatt  1020
gtggttgtag ggacttaagt accactttta ataatatgat taagccatgg cattttggac  1080
gagcgaaaca aactgtttaa aagcagataa aaatgtattg tggagtaata cataaataaa  1140
caaagcgaga taattgtaat tagcatgtat ttgctaactt tttataccta gcttttaaga  1200
```

```
aaatctctta ccgtacacag ttggtacttt aaaagcaaga gtctcatttt cattttatga    1260
cccatttaag acaaactaca gcaattacaa gtatattggc cacagaccca gacgtgcgat    1320
gattatatga attctgagtt catttcgcac acttgttctt acaaaagaaa caaattaagt    1380
ttctgaactt taaaaccacc tgatagagat tgtcactgcc aaggagaatc acaacaaact    1440
ttaaactaaa tcatataaag atcataaact gacccaaaat taactctttt tcttaggtgg    1500
caaagaaggg catggagaac tacagatttg gcagtgtgga ctatgccgtt ttcctgggca    1560
tgatcgtatt atccaccagc acgggcatct atttcgggtg catcaagtga gtgaccttta    1620
aacaaatcct cggaatattg ccaaacaatt gttgtaatta caggaagagc aaggtgaagc    1680
tcgaggaggc ggaacccact ctgccgacga ccacgccaaa aaggcggaaa cacgatttcg    1740
gatcggagaa gatgagcgag tatctgctag ggtcacgcaa tctgaaagtt ttccccgttg    1800
ccatgagcct gatagccagg tagagttggc gatgcgatcc cgcacctcca aatatgcctg    1860
tacaatctgt tccctttat ttccagctat atatcgggcg ttaccatact gggcacaacc    1920
tctgagatct acaattatgg cacgcaatat tggtttatag ccatagcaat aatgctccaa    1980
ggtattgccg tctcctacgt ctacatacca gtgttctcgg ctcttcaagt aggctcttcc    2040
tatgaggtac gatactcgta aattctataa actgatttat acatttacaa tctaatgggt    2100
caataagctt atgctaacag taaaagtaat aacgtccaga acgcaaccaa aaatgtaaat    2160
tgggttttaa cggaaatatt aatttagcta taaaatactc accatttctt tcaatgacga    2220
gttagttaaa ataagatag acaagttcat ctgtagtggt tgctgataag aatgacaaac    2280
tttctaagat gtttccgtct tcccccttc gctccgtcac ttttgtccaa tcaatgaacg    2340
gaggacgtag tgaacacttt aattaactgg gaatcggaga ccaccctccc ctcaagtgga    2400
atttcttgga ctttgcactc gcccacttgt tgcgactttt ttctgggttc cagcggttcg    2460
atatgattaa ttgcaatgtg gttttctgcc acttgacaat tgtgtcgagc aattagtttt    2520
cgttttcggt ctttatgacg ttagttttcg aatcctaaac gcaagtcatt tgaattatga    2580
aatataatat tgctttcagt acttggagat gcgctttcat tcggtcgtac gaagtattgc    2640
atcctttatg tttattctgg atgaggtaag tcaaagataa tatttggact gcaatgttgt    2700
aataattgtc gatccaattt tagattctgt ttctgccttt cattgtgtat gtaccagcta    2760
tagctctgaa tcagggtaag ccgcatttgt taattgtttg aaacacaact ttaatctttc    2820
gataatcttg cagtatcggg cattaatctc catgtgattg cagtggtaat tgtggtcgtg    2880
tgtgttttct acacctttgt cgtaagtttt agagagtttc atacgtatgt ttttatacta    2940
atggcgccta ttttcaggga ggaatcaaag cagtggtcca cacagatgct tggcaggtgc    3000
tggtcatgtt cctttccgtt cttgctgtgg ctattttggc cactgtctat gcaaatggct    3060
tgaatgtcct tttcgatgat gctgccaaag gtggccgatt gatctttaac aatacaaacc    3120
catcgcctta tgtaaggcac actgtttgga gcgtcctaat cggggattc tcctactgga    3180 cctcattcaa tgccgtcaac cagaccatgg tccagcgata catgtctctt ccatcgctca    3240
agaaggctcg tgcttccatg gccattttta caattggcgt ggctgccttc gtctctgttt    3300
gttgttatgt gggactgcta atctatgaga tgtacaaaga ttgtgatcct ctgagtgcgg    3360
gactaataac agtgagtaaa taataaattg ttttgaact ttacttacgt ttatttcctt    3420
gcagcacgac gatcagctac tgccgctctt tgtcgttcag agtgtgggtc atatctatgg    3480
tatgtctggt ttgtttatag ccggcatatt tggagctgcc ttgagctccc tttctgtggt    3540
```

```
tctgaactca acgtccttgg taatcctgga ggatatagtt cgcggctgct tcaagatgca    3600
accaagtgaa agagcctcca ccattctggt aaagtcaact gttatagttc ttggctttgt    3660
ggccctatca ctggtatttg tcctggaaca actgagtgga atcctgagca tttgcacttc    3720
aatgacggcc atcgcagctg aaccactttt ggcctgtttt accctgggaa tgctcgttcc    3780
ctgggccaat actgtaggca ctgctgtggg cggaattgca agtgctctgc tcgccgggtg    3840
gatatccttt ggaacgcagt ttaccatcgc agcgggtgaa ttgaattctc aaaagcttcc    3900
cgtatccgtg gagggatgtg tgggcaatgt aacgcttcgg gaaaatatat gggtagatga    3960
ggagcaagtt tttccactgt accgactgtc ctaccactgg ataaatccca ttggtgtggc    4020
cacagtcatt gtggtaggtg cactagtctc ccttgtgacc aaacccacaa atatgaaaac    4080
actagatccg gatctaatat caccagtgat tcacaggtaa ttttgtaac cacatgttta    4140
acctctgtta ttaaacccat ttttcttct agattccttc caaaagaatg ctttagtggt    4200
cgcaatctcc atgcgcaggc gcacaaaaac ctcttaaacg tatcctaaaa tagacgaacc    4260
agaacttcct gtgccaaact aatggaattg atggcattga attccacacc ctgttttgtt    4320
agcatagttt gtagttgtag ttgctttgtg gtagttacct tatagatagc ctagtctagt    4380
acaatgtgat ccagatattg gaagacataa accgaagtac aggaacctat gaatctgcat    4440
ctcagaatac agagtgcaca atcattaacg ttatatagta aatgtattat aatatagctt    4500
tatttaattg ttctgtttgt atccgttctt tactttccag cctttgttca agcattattt    4560
ttttggcatt ttcgatttgt agtcagcaga ctgtgtctca ttatgtattc cgtttgactt    4620
tacaagcata atgtctgtga taaattcaat aaatagatca tacatact              4668

<210> SEQ ID NO 4
<211> LENGTH: 8668
<212> TYPE: DNA
<213> ORGANISM: Drosophila melanogaster

<400> SEQUENCE: 4
gatggtgaca cgggggggaga gattccggga gatcgtgagg gacttctggt cagtggtgag     60
ggtgcatcaa agacctctgg tcttggagtc agtgaaagca gaagttgagt tggcatctgg    120
acctggggtt gagtagtgtc tggagttggt ggagatactc tcagctccgg agaagccttc    180
aagctgagta gcctcttggg atgcagttgc tcctttgctt ttatgggctg tgccaccgta    240
gcattactgg cttggctgct gctactactt tgtacggaaa cggaggaggc accgctgagt    300
atgttatcca aaagggattc aggcgaagta gagctacctc ctccagccaa gctgctagtg    360
ggctcactgc cactgtccct atcctgcaca ccgagttcga cattggatag ccctgtacct    420
gatgaccctg cacccgggc actattcgac aaacccaaag tcctagatct tcggatggag    480
ctctttggtg ccaaacccgg tagctttggc actgagggta gatgtatttt cgaagtcact    540
tcgctctttg gggcaatagt aaaggtaaaa agttgtggtg ctgatttgcg acgcactgcg    600
tctggtaagg gagcggtctg cagattattc tgcgaagtct gtgcgttttt tcgtaaggaa    660
attttggcag aactcaactt tatcttaagt ttccctaagg atgcactggg tggcacagct    720
ggagtaggag gtgggctcgg aacaactatt tccacatccc ctcggatgcg ttcgtaatcc    780
gttaactggc cactcttgtt tccgttactc gttttttcgct tgaaagcgat tttcgagcga    840
ttttccctgc tcatgcttcc cggttatgca atcctgcagc tcggactacg gattccaggc    900
aatctggagc accaccgcgt gttcccgttg caattgggac tgaaactgag actgggtctc    960
ggacttggtt gctgcctaat ccaattacat tcctcattgg aaacccacgg cgcactgcga   1020
```

```
gtgcgaatgg tggcaaaagt ctgacactga caattgtgca attatctgtt gtggttgctc    1080
attctaaata gttctttcat gacaacctgt cacttgctat tgattgactt tctgattttc    1140
tgaatccaga gagtatttcg tggtatgatg ggtgggagaa gatccaacgg agtaaccaaa    1200
ggaacgtctc aacttccgag tacccgcta aacccgtgaa gtgaaactct agatggaccc    1260
gatgtcggta gtgaatcaat tatttttca tttaccacca aaagggagtg ttcaaattac    1320 ttctatttt aaatgtggca atggtaaact taggtgtgta gtttactaca cgttacttga    1380
gcaattgata gtgaatatat aataatttca atattacaga aaacccataa tgtcatatta    1440
atactaataa cctttaaca tatgtgtttt taaaattgtt cgaataatag cggataacaa    1500
cagttgagta ttttttcatc tgaatgcaac tagctgctcc aaacttccgt taatagctcc    1560
attagctgat cgaatggcca agtaaccact tacattgaca taatacattg tgaggattac    1620
aaaagcaacg aagctttctc tcccacctaa tcttgccaaa gcccccacac atttacaaca    1680
ctcgctcttt tactctctct atacgcaatg caagataaa tggttgggag agggagcttt    1740
tcgagcgcag tattaagggg tatattatgt tcatgttaca aataatactt ttatccagaa    1800
aatatcagtt gtattcccaa tacttgagtc atttatacat ttagttttat ttatacattt    1860
tatttttatt ctgttccgtt gttcctatgt taaatatgag gtaatgggta tactttgatc    1920
ggtactctcc attctagctg tcccacttgt ttttgtcgag cagctggcct agtggctttt    1980
attttcgacc cgctcgcaga catcagttgc agttcggaag cggaatcggt tgatgttgtt    2040
gctccgattc ggacgtggaa tatttcgctt ttgtacactc gtattttcga cttcaaagaa    2100
tcgggcaaaa gcgcacagaa cagacctgaa aaacttttcc gtgcgtttcc gagttttgtt    2160
ttaatgtgtt ccatgtgatt aactttgtac gtttatagaa ccctttttta aaaaccaatg    2220
gaaatacacg gaatccgttg acccttttg ccacaagaaa attttcatta cgtttcgcag    2280
aatttgttgg tagtttgctc tttctggccg tttatcgtgc gttgctttgc tgttgattt     2340 cgtgagggac gcgcaatttt ccattcacct ccgctgctcc agttacggaa gccaccccca    2400
ccattgtaaa gcctagcgtt tgccggtccc aacaatatg gaagcggtac gtattttgca     2460
catttcgccg gttccaaaca ttaagagcta tttaggaact ttggagcggg ggacacggca    2520
tttgggttac aaagtccaag tccagggcga taatgctgct gctgctcgag atattgcgta    2580
aaaggttgaa gtctcttctc tgagattcga tcggctccga ttgatcatcc agtcaatgaa    2640
cctaaatggc agacgaaaaa ttagtatttt atgctaaaca ccgtctgcat cattagatag    2700
gaactaagaa agtaaagaa aattgggagt attaaaaata tattaatttt gctaataaca    2760
aaagattcat aatctagaaa accaaagctg gataatgtca agtcaccag aacgagttat     2820 cttgccaaat atgcatttga taataacgcg aaatcatatt aataaaatgt tttgtaatt     2880 tgaagcgatt gctaaacatg ttaaataaat aatacatggg gaaaagggtt aaagtctcta    2940
gtccgtagag attgatgaat aataagcagg cacctgctga taagacctgg ttcccataac    3000
ttcacatgga catggacatt gtggttgtag ggacttaagt accactttta ataatatgat    3060
taagccatgg cattttggac gagcgaaaca aactgtttaa aagcagataa aaatgtattg    3120
tggagtaata cataaataaa caaagcgaga taattgtaat tagcatgtat ttgctaactt    3180
tttataccta gcttttaaga aaatctctta ccgtacacag ttggtacttt aaaagcaaga    3240
gtctcatttt catttatga cccatttaag acaaactaca gcaattacaa gtatattggc    3300
cacagaccca gacgtgcgat gattatatga attctgagtt catttcgcac acttgttctt    3360
```

```
acaaaagaaa caaattaagt ttctgaactt taaaaccacc tgatagagat tgtcactgcc    3420
aaggagaatc acaacaaact ttaaactaaa tcatataaag atcataaact gacccaaaat    3480
taactctttt tcttaggtgg caaagaaggg catggagaac tacagatttg cagtgtgga     3540 ctatgccgtt ttcctgggca tgatcgtatt atccaccagc acgggcatct atttcgggtg    3600
catcaagtga gtgacccttta aacaaatcct cggaatattg ccaaacaatt gttgtaatta   3660
caggaagagc aaggtgaagc tcgaggaggc ggaacccact ctgccgacga ccacgccaaa    3720
aaggcggaaa cacgatttcg gatcggagaa gatgagcgag tatctgctag ggtcacgcaa    3780
tctgaaagtt ttccccgttg ccatgagcct gatagccagg tagagttggc gatgcgatcc    3840
cgcacctcca aatatgcctg tacaatctgt tcccttttat ttccagctat atatcgggcg    3900
ttaccatact gggcacaacc tctgagatct acaattatgg cacgcaatat tggtttatag    3960
ccatagcaat aatgctccaa ggtattgccg tctcctacgt ctacatacca gtgttctcgg    4020
ctcttcaagt aggctcttcc tatgaggtac gatactcgta aattctataa actgatttat    4080
acatttacaa tctaatgggt caataagctt atgctaacag taaagtaat aacgtccaga    4140 acgcaaccaa aaatgtaaat tgggttttaa cggaaatatt aatttagcta taaaatactc    4200
accatttctt tcaatgacga gttagttaaa ataaagatag acaagttcat ctgtagtggt    4260
tgctgataag aatgacaaac tttctaagat gtttccgtct tccccctttc gctccgtcac    4320
ttttgtccaa tcaatgaacg gaggacgtag tgaaacttt aattaactgg gaatcggaga    4380
ccaccctccc ctcaagtgga atttcttgga ctttgcactc gcccacttgt tgcgacttt     4440 ttctgggttc cagcggttcg atatgattaa ttgcaatgtg gttttctgcc acttgacaat    4500
tgtgtcgagc aattagtttt cgttttcggt ctttatgacg ttagttttcg aatcctaaac    4560
gcaagtcatt tgaattatga aatataatat tgctttcagt acttggagat gcgctttcat    4620
tcggtcgtac gaagtattgc atcctttatg tttattctgg atgaggtaag tcaaagataa    4680
tatttggact gcaatgttgt aataattgtc gatccaattt tagattctgt ttctgccttt    4740
cattgtgtat gtaccagcta tagctctgaa tcagggtaag ccgcatttgt taattgtttg    4800
aaacacaact ttaatctttc gataatcttg cagtatcggg cattaatctc catgtgattg    4860
cagtggtaat tgtggtcgtg tgtgttttct acacctttgt cgtaagtttt agagagtttc    4920
atacgtatgt ttttatacta atggcgccta ttttcaggga ggaatcaaag cagtggtcca    4980
cacagatgct tggcaggtgc tggtcatgtt cctttccgtt cttgctgtgg ctattttggc    5040
cactgtctat gcaaatggct tgaatgtcct tttcgatgat gctgccaaag gtggccgatt    5100
gatctttaac aatacaaacc catcgcctta tgtaaggcac actgtttgga gcgtcctaat    5160
cgggggattc tcctactgga cctcattcaa tgccgtcaac cagaccatgg tccagcgata    5220
catgtctctt ccatcgctca agaaggctcg tgcttccatg gccatttta caattggcgt    5280 ggctgccttc gtctctgttt gttgttatgt gggactgcta atctatgaga tgtacaaaga    5340
ttgtgatcct ctgagtgcgg gactaataac agtgagtaaa taataaattg ttttgaact    5400 ttacttacgt ttatttcctt gcagcacgac gatcagctac tgccgctctt tgtcgttcag    5460
agtgtgggtc atatctatgg tatgtctggt ttgtttatag ccggcatatt tggagctgcc    5520
ttgagctccc tttctgtggt tctgaactca acgtccttgg taatcctgga ggatatagtt    5580
cgcggctgct tcaagatgca accaagtgaa agagcctcca ccattctggt aaagtcaact    5640
gttatagttc ttggctttgt ggccctatca ctggtatttg tcctgaaaca actgagtgga    5700
atcctgagca tttgcacttc aatgacggcc atcgcagctg gaaccacttt tggcctgttt    5760
```

```
accctgggaa tgctcgttcc ctgggccaat actgtaggca ctgctgtggg cggaattgca   5820
agtgctctgc tcgccgggtg gatatccttt ggaacgcagt ttaccatcgc agcgggtgaa   5880
ttgaattctc aaaagcttcc cgtatccgtg gagggatgtg tgggcaatgt aacgcttcgg   5940
gaaaatatat gggtagatga ggagcaagtt tttccactgt accgactgtc ctaccactgg   6000
ataaatccca ttggtgtggc cacagtcatt gtggtaggtg cactagtctc ccttgtgacc   6060
aaacccacaa atatgaaaac actagatccg gatctaatat caccagtgat tcacaggtaa   6120
tttttgtaac cacatgttta acctctgtta ttaaacccat tttttcttct agattccttc   6180
caaaagaatg ctttagtggt cgcaatctcc atgcgcaggc gcacaaaaac ctcttaaacg   6240
tatcctaaaa tagacgaacc agaacttcct gtgccaaact aatggaattg atggcattga   6300
attccacacc ctgttttgtt agcatagttt gtagttgtag ttgctttgtg gtagttacct   6360
tatagatagc ctagtctagt acaatgtgat ccagatattg gaagacataa accgaagtac   6420
aggaacctat gaatctgcat ctcagaatac agagtgcaca atcattaacg ttatatagta   6480
aatgtattat aatatagctt tatttaattg ttctgtttgt atccgttctt tactttccag   6540
cctttgttca agcattattt ttttggcatt ttcgatttgt agtcagcaga ctgtgtctca   6600
ttatgtattc cgtttgactt tacaagcata atgtctgtga taaattcaat aaatagatca   6660
tacatactat ccgaattttg tacacctaga atatagttaa gcggttgcaa agcagcagga   6720
atgatatgac ctctgtctgg atctggatct gggatctgag tctggaatct ggcgtatcta   6780
gtctaaacta agccccaatc aggcgtaaat cacaaaagag gatatgcctt gtataggcat   6840
gcttatacat actaattaac cttccgatga tctacagccg acgactgtct tctgctttgg   6900
atgcactttc gtagctggaa cccgatgaca attaggcaaa gaatgccagc actcagatag   6960
ctattgaaga caaactgctg tggcagcatt ttgcacttgg aaaccacata gtcatcgggg   7020
gttatagtgg cctaaaagtt atggcatgtt agtacaagtt cgaagggcta acaatcgtaa   7080
gagcaaatat aatactcacc agcataaagc tgggattaac tttgtttcgc cagctgaatg   7140
aggccaccgt gtactcatcg atgcccagtc gatttacact gtgacagaag tgatgtgaat   7200
gaccggcgaa tgccagcctt ggcttaagca gctctcccag catatccgtg gcatccttgg   7260
agagcacatg aaaccgctct cggaacgcct cgatgtacgg agcatcgtgc tcctcgcaca   7320
tggtatccga aatgcggtag gtgggaaagt gctgcaatag aattggctgg ctgtacgggt   7380
gccgcctggt gcgagcgcac tccgcctcta gtggatactt catgcagtac aaagtcctcg   7440
aaatgttttt caactgatcc tcggcctggg tgcaaaacat gcaaccatca ccttccatag   7500
ccatcgaatt tatcaccaca aaatggattt gtttaatggt gtacaaattg accgaggagt   7560
tgttcagata actctcaaaa cgcgacataa agaagggatg cattctggaa acacacaag   7620 agcgcggttt aacaaatatc agggaataca catagtctct tattgactta cttgtaatgg   7680
aagcccacgt catgatttcc cgcgacactg atgagcggaa ttcccggtgg taggtggaac   7740
atcttcaggt agcgccacac atattcctgg aactgcttgt cgctgaccat gtcgccctcg   7800
tcgaacaaat cgcccaagac gaagaccacg tcgggctgga acagacgtga tgccgcctga   7860
aaggcccgcg tcatgtgcca ctcccggtag agcttgtcca gccagtgacc acgatgcggt   7920
cccagcagat gcggatccgc tagaatcatt gccctaagcg gatcgtccac atacttcttt   7980
cgctttatct ccggccactt gcacttttgc agcaccacaa agtccgccac atattcgcag   8040
aagatcaggg cgcacagcac gatcacaaag caggcataaa gaaagcgcat ttcaggattt   8100
```

```
ctcaccggct aaaaaaataa taacaaattt attctagagc tgaaaaacca tcagcgatag      8160
tatcgtttta aacgagtaaa cggcccgata taaatttaaa atattcgata aattaaacag      8220
tgctgtcaag cggctgtcgg ttgactaaca aattggcgcc tcatttcaaa gttggttact      8280
aaaattgtaa attggaaaaa ttatgaagca ttatggctta tatataattt cctttatttg      8340
gaataggtat tgtgcattgc atgctgctta caggctaact agaagagatc gtaaaaatag      8400
tttaggcctt ggccaagttc ccagattgaa atgccagtgc ccagttcctg ggcgagcttt      8460
attcgctcgt ttatggaata gagagtggga taaaagacaa tgtggcgacc gtcatcgttt      8520
ctgaaagtaa tgatattcat catcttcgcc ttacactctg catacgctgc agtagaaaac      8580
tcacttgatt tcaaagaaat tttccacatc ccgctcatcg taagttaggt gcttcttcac      8640
atgcctgact agatccaagt actgggag                                         8668

<210> SEQ ID NO 5
<211> LENGTH: 20
<212> TYPE: DNA
<213> ORGANISM: Drosophila melanogaster

<400> SEQUENCE: 5
tgcttcaaga tgcaaccaag                                                    20

<210> SEQ ID NO 6
<211> LENGTH: 20
<212> TYPE: DNA
<213> ORGANISM: Drosophila melanogaster

<400> SEQUENCE: 6
ttgaagtgca aatgctcagg                                                    20

<210> SEQ ID NO 7
<211> LENGTH: 18
<212> TYPE: DNA
<213> ORGANISM: Drosophila melanogaster

<400> SEQUENCE: 7
gaaatcaagg ctaggtcg                                                      18

<210> SEQ ID NO 8
<211> LENGTH: 22
<212> TYPE: DNA
<213> ORGANISM: Drosophila melanogaster

<400> SEQUENCE: 8
aatgggtgtc gctgaagaag tc                                                 22
```